US008288438B2

(12) United States Patent
Sanders et al.

(10) Patent No.: US 8,288,438 B2
(45) Date of Patent: Oct. 16, 2012

(54) METHODS FOR AVOIDING EDEMA IN THE TREATMENT OR PREVENTION OF PPARγ-RESPONSIVE DISEASES, INCLUDING CANCER

(75) Inventors: Martin E. Sanders, Hillsborough, CA (US); David B. Karpf, Monte Sereno, CA (US)

(73) Assignees: Metabolex, Inc., Hayward, CA (US); Dia Tex, Inc., San Antonio, TX (US)

( * ) Notice: Subject to any disclaimer, the term of this patent is extended or adjusted under 35 U.S.C. 154(b) by 1110 days.

(21) Appl. No.: 11/908,952

(22) PCT Filed: Mar. 21, 2006

(86) PCT No.: PCT/US2006/010331
§ 371 (c)(1),
(2), (4) Date: Apr. 7, 2008

(87) PCT Pub. No.: WO2006/102375
PCT Pub. Date: Sep. 28, 2006

(65) Prior Publication Data
US 2008/0269189 A1 Oct. 30, 2008

Related U.S. Application Data

(60) Provisional application No. 60/663,977, filed on Mar. 21, 2005, provisional application No. 60/664,515, filed on Mar. 22, 2005.

(51) Int. Cl.
*A61K 31/20* (2006.01)
(52) U.S. Cl. ........................................................ 514/559
(58) Field of Classification Search ........................ None
See application file for complete search history.

(56) References Cited

U.S. PATENT DOCUMENTS

| | | | |
|---|---|---|---|
| 6,242,196 B1 | 6/2001 | Spiegelman et al. | |
| 6,262,118 B1 | 7/2001 | Luskey et al. | |
| 6,294,559 B1 | 9/2001 | Smith | |
| 6,579,893 B1 | 6/2003 | Urban et al. | |
| 6,599,899 B2 | 7/2003 | Burris et al. | |
| 6,613,802 B1 | 9/2003 | Luskey et al. | |
| 6,624,194 B1 * | 9/2003 | Luskey et al. | 514/559 |
| 6,646,004 B1 | 11/2003 | Luskey et al. | |
| 6,653,332 B2 * | 11/2003 | Jaen et al. | 514/347 |
| 6,696,474 B2 * | 2/2004 | Bigge et al. | 514/374 |
| 6,966,967 B2 | 11/2005 | Curry et al. | |
| 2003/0032581 A1 | 2/2003 | Berger et al. | |
| 2003/0220399 A1 | 11/2003 | Luskey et al. | |
| 2004/0029933 A1 | 2/2004 | Zhao et al. | |
| 2004/0077659 A1 | 4/2004 | Oliver Jr | |
| 2004/0162354 A1 | 8/2004 | Evans et al. | |
| 2004/0266834 A1 | 12/2004 | Copland, III et al. | |
| 2007/0059762 A1 | 3/2007 | Araki et al. | |

FOREIGN PATENT DOCUMENTS

| | | |
|---|---|---|
| WO | WO 97/28149 A1 | 8/1997 |
| WO | WO 98/25598 A2 | 6/1998 |
| WO | WO 99/04815 A1 | 2/1999 |
| WO | WO 03/080545 A2 | 10/2003 |
| WO | WO 2004014308 A2 | 2/2004 |
| WO | WO 2004/112774 A1 | 12/2004 |
| WO | WO 2004106542 A1 | 12/2004 |
| WO | WO 2006/102426 A2 | 9/2006 |

OTHER PUBLICATIONS

Cabrero et al., Peroxisome Proliferator-Activated Receptors and the Control of Inflammation, Current Drug Targets-Inflammation & Allergy, 2002, I 242-248.*
Berger, Joel, et al. "The Mechanisms of Action PPARs," Annu. Rev. Med. 2002, vol. 53, pp. 409-435.
Cabrero, A, et al. Peroxisome Proliferator-Activated Receptors and the Control of Inflammation, Current Drug Targets—Inflammation and Allergy, 2002, vol. 1, No. 3, pp. 243-248.
Eucker, et al., "Ligands of peroxisome proliferator-activated receptor γ induce apoptosis in multiple myeloma," Anti-Cancer Drugs, 2004, vol. 15, No. 10, pp. 955-960.
Fujii, et al., "The Ligands of Peroxisome Proliferator-activated Receptor (PPAR) Gamma Inhibit Growth of Human Esophageal Carcinoma Cells through Induction of Apoptosis and Cell Cycle Arrest," Anticancer Research, 2004, vol. 24 pp. 1409-1416.
Keshamouni, Venkateshwar, et al., "Peroxisome proliferator-activated receptor-γ activation inhibits tumor progression in non-small-cell lung cancer," Oncogene, 2004, vol. 23, No. 1, pp. 100-108.
Mitsiades, Constantine S. et al., "Novel Biologically Based Therapies for Waldenstrom's Macroglobulinemia," Seminars in Oncology, vol. 30, No. 2 (2003) pp. 309-312.
Muller, et al., "Terminal Differentiation of Human Breast Cancer through PPARγ" Molecular Cell, 1998, vol. 1, pp. 465-470.
Ricote, M., et al. "The Peroxisome Proliferator Activated Receptor-gamma is a negative regulator of macrophage activation," Nature, 1998, vol. 391, pp. 79-82.
Rosenstock, J., et al. "MBX-102: A Novel Non-TZD Insulin Sensitizer that Improves Glycemic Control without Causing with Causing Edema or Weight Gain in Patients with Type 2 Diabetes (T2DM) on Concomitant Insulin Therapy," Edema Diabetes, 2005, p. A11.
Schoonjans, Kristina et al., "Peroxisome proliferator-activated receptors, orphans, with ligands and functions," Curr. Opin. Lipidol. 8, 159-166 (1997).
Spiegelman, B.M., "PPAR$_γ$: Adipogenic Regulator and Thiazolidinedione Receptor." Diabetes, 1998, vol. 47, pp. 507-514.
Tsujie, masanori, et al. "Thiazolidinediones inhibit growth of gastrointestinal, biliary, and pancreatic adenocarcinoma cells through activation of the peroxisome proliferator-activated receptor$_γ$/retinoid X receptor α pathway," Experimental Cell Research, 2003, vol. 289 No. 1 pp. 143-151.
Willson, Timothy et al., "The PPARs: From Orphan Receptors to Drug Discovery," Journal of Medicinal Chemistry, 2000, vol. 43, No. 4, pp. 527-550.

(Continued)

*Primary Examiner* — Sreeni Padmanabhan
*Assistant Examiner* — Svetlana M Ivanova
(74) *Attorney, Agent, or Firm* — Hamilton DeSanctis & Cha, LLP

(57) ABSTRACT

Compounds, compositions, and methods of avoiding edema while treating or preventing PPARγ-mediated diseases, including cancer, using derivatives and prodrugs are provided.

16 Claims, 24 Drawing Sheets

OTHER PUBLICATIONS

Yoshimura, et al. "The effect of peroxisome proliferator-activated receptor-γ ligand on urological cancer cells," International Journal of Molecular Medicine, 2003 vol. 12, No. 6, pp. 861-865.

Yoshizumi, et al., "Thiazolidinedione, a peroxisome proliferator-activated receptor-γ ligand, inhibits growth and metastasis of HT-29 human colon cancer cells through differentiation-promoting effects," International Journal of Oncology, 2004, vol. 25, No. 3, pp. 631-639.

Taylor et al., "Peroxisome Proliferator-Activated Receptor Agonists Inhibit Inflammatory Edema and Hyperalgesia", Inflammation, 26(3):121-127 (2002).

* cited by examiner

Figure 4B
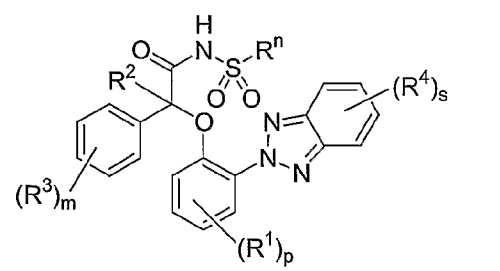
IIan
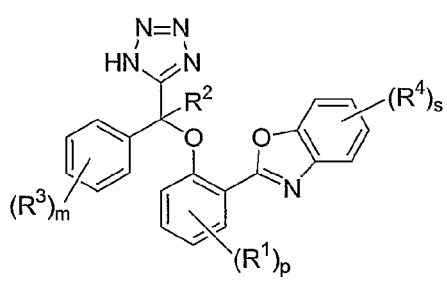
IIao
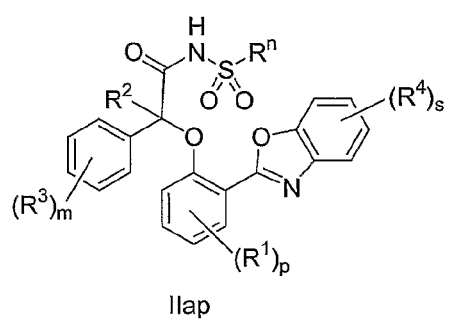
IIap
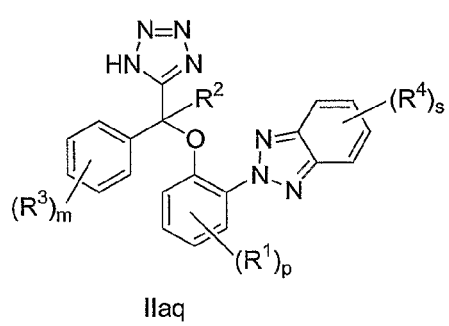
IIaq
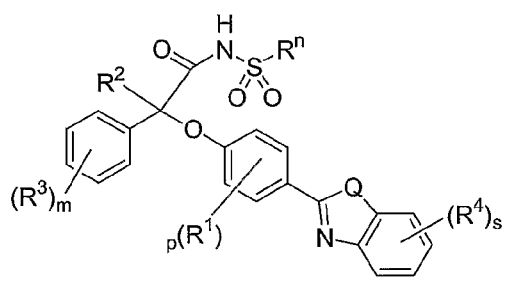
IIar Q = O
IIas Q = S
IIat Q = NH or NR
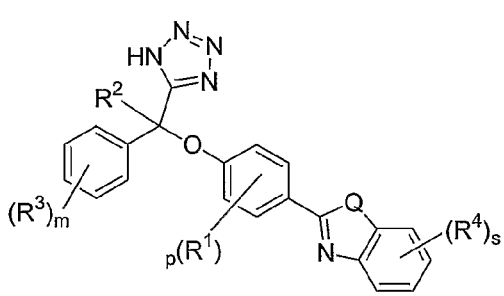
IIax Q = O
IIay Q = S
IIaz Q = NH or NR Figure 7  FPG – Absolute Change from Baseline in the First study Figure 8   HbA1c – Absolute Change from Baseline in the First Study Figure 9  Incidence of Edema in the First Study Figure 11  FPG – Absolute Change from Baseline in the Second Study Figure 12  HbA1c – Absolute Change from Baseline in the Second Study Figure 13  HbA1c – Absolute Change from Baseline in the Second Study (Minus Sites 60 and 70)

Figure 14  FPG – Absolute Change from Baseline in the Second Study (Minus Sites 60 and 70)

Figure 15   HbA1c – Absolute Change from Baseline in the First Study (Minus Sites 60 and 70)

Figure 16  FPG – Absolute Change from Baseline in the First study (Minus Sites 60 & 70)

Figure 17  Combined Incidence of Edema in First and Second Phase 2 Studies

A = combined placebo groups
B = all dose groups combined
C = 200 mg dose group
D = 400 + 600 mg dose groups combined
E = 600 mg dose group Figure 18 Change from Baseline in Weight Second Study Dose-dependent Decrease in hsCRP
(14 Day Treatment vs 3-6 months for Actos)

* Goldberg RB, et al. A comparison of lipid and glycemic effects of pioglitazone and rosiglitazone in patients with type 2 diabetes and dyslipidemia. Diabetes Care 28(7):1547-54, 2005

Actos data is from the above cited literature.

METHODS FOR AVOIDING EDEMA IN THE TREATMENT OR PREVENTION OF PPARγ-RESPONSIVE DISEASES, INCLUDING CANCER

RELATED APPLICATIONS

This application claims benefit under 35 U.S.C. §112(e) of U.S. Provisional Application Ser. No. 60/663,977, filed Mar. 21, 2005, and of U.S. Provisional Application Ser. No. 60/664,515 filed Mar. 22, 2005, the disclosure of each of which is incorporated herein in its entirety for all purposes to the extent not inconsistent with the present disclosure. This application is related in subject matter to a PCT application of the same inventorship and assignment as the present application, entitled "Methods for Avoiding Edema in the Treatment of Metabolic, Inflammatory, and Cardiovascular Disorders," filed Mar. 21, 2006 PCT/US06/10331, which is incorporated herein by reference in its entirety.

STATEMENT AS TO RIGHTS TO INVENTIONS MADE UNDER FEDERALLY SPONSORED RESEARCH AND DEVELOPMENT

Not Applicable

REFERENCE TO A "SEQUENCE LISTING," A TABLE, OR A COMPUTER PROGRAM LISTING APPENDIX SUBMITTED ON A COMPACT DISK

Not Applicable

BACKGROUND OF THE INVENTION

Peroxisome proliferator-activated receptors (PPARs) are members of the nuclear receptor superfamily of transcription factors, a large and diverse group of proteins that mediate ligand-dependent transcriptional activation and repression. They play a role in controlling expression of proteins that regulate lipid metabolism. Furthermore, the PPARs are activated by fatty acids and fatty acid metabolites. Three PPAR subtypes have been isolated: PPARα, PPARβ (also referred to as δ or NUC1), and PPARγ. Each receptor shows a different pattern of gene expression by binding to DNA sequence elements, termed PPAR response elements (PPRE). In addition, each receptor show a difference in activation by structurally diverse compounds. To date, PPREs have been identified in the enhancers of a number of genes encoding proteins that regulate lipid metabolism suggesting that PPARs play a pivotal role in the adipogenic signaling cascade and lipid homeostasis (Keller, H. and Wahli, W. *Trends Endoodn. Met.* 4:291-296 (1993).

PPARα is found in the liver, heart, kidney, muscle, brown adipose tissue and gut and is involved in stimulating β-oxidation of fatty acids. PPARα is also involved in the control of cholesterol levels in rodents and in humans. Fibrates are weak PPARα agonists that are effective in the treatment of lipid disorders. In humans, they have been shown to lower plasma triglycerides and LDL cholesterol. In addition, PPARα agonists have also been reported to prevent diabetes and to improve insulin sensitivity and reduce adiposity in obese and diabetic rodents (see Koh, E. H. et al. *Diabetes* 52:2331-2337 (2003); and Guerre-Millo, M. et al. *J. Biol. Chem.* 275: 16638-16642 (2000)).

PPARβ is ubiquitously expressed. Activation of PPARβ increases HDL levels in rodents and monkeys (see Oliver, W. R. et al. *PNAS* 98:5306-5311 (2001); and Leibowitz, M. D. et al. *FEBS Letters* 473:333-336 (2000)). Moreover, PPARβ has been recently shown to be a key regulator of lipid catabolism and energy uncoupling in skeletal muscle cells (Dressel, U. et al. *Mol Endocrinol.* 17: 2477-2493 (2003)). In rodents, activation of PPARβ induces fatty β-oxidation in skeletal muscle and adipose tissue, leading to protection against diet-induced obesity and diabetes (see Wang, Y. X. et al. *Cell* 113:159-170 (2003); and Tanaka et al. *PNAS* 100:15924-15929 (2003)). In human macrophages, PPARβ activation also increases the reverse cholesterol transporter ATP-binding cassette A1 and induces apolipoprotein A1-specific cholesterol efflux (see Oliver, W. R. et al. *PNAS* 98:5306-5311 (2001)).

PPARγ is expressed most abundantly in adipose tissue and induces adipocyte differentiation. Drugs of the thiazolidinedione (TZD) class namely troglitazone, pioglitazone, and rosiglitazone are potent and selective activators of PPARγ. In humans, these drugs increase insulin action, reduce serum glucose, induce the differentiation of preadipocytes to adipocytes, and have small but significant effects on reducing serum triglyceride levels in patients with type 2 diabetes. These agents have also been implicated in the regulation of triglyceride and cholesterol levels in humans or animal models (See, e.g., U.S. Pat. No. 5,859,501, and PCT publications WO 97/28149 and 99/04815). The role of PPARs in the regulation of metabolism has been the subject of a number of reviews (see, Spiegelman, *Diabetes*, Vol. 47, pp. 507-514 (1998); Schoonjans, et al., *Curr. Opin. Lipidol.* 8, 159-166 (1997); Brun, et al., *Curr. Opin. Lipidol.* 8: 212-218 (1997). More recently, the (−) isomers of halofenic acid which are particularly useful in the treatment of insulin resistance, Type II diabetes, obesity, and hyperuricemia (See, U.S. Pat. Nos. 6,646,004; 6,624,194; 6,613,802; and 6,262,118, each to Luskey et al.) have also been recently reported to be selective, partial PPARγ agonists.

The PPARγ receptor is found in many other tissues than adipose tissue. PPARγ modulators can have beneficial effects in many other diseases including cardiovascular disease, inflammation, and cancer. (Schoonjans et al, *Curr. Opin. Lipidol.* 8, 159-166 (1997); Ricote, et al., *Nature* 391: 79-82 (1998); Mueller, et al., Mol. *Cell* 1: 465-470 (1998)).

PPARγ activation induces growth arrest by terminal differentiation of actively proliferating PPARγ-expressing cells, including transformed adipose precursor cells. PPARγ is consistently and selectively expressed in each of the major histologic types of human liposarcoma compared to other soft tissue sarcomas and is also selectively expressed in human breast adenocarcinomas and advanced metastatic breast tumors (see WO 98/25598). PPARγ activators have been shown to induce differentiation of malignant liposarcoma cell lines to adopt a morphology characteristic of mature cultured adipocytes. PPARγ activators also have been shown to induce cell-cycle withdrawal in NIH3T3 cells transfected with PPARγ, in transformed brown adipocyte cell line HIB 1B, and in NIH-3T3-F442A preadipocytes. PPARγ modulators have also been found to reduce the size of adipose cell tumors (HIB 1B) in nude mice.

PPARγ is expressed in many human cancer cell lines and have been shown to inhibit the proliferation of leukemic cells, prostate cancer cells, and breast cancer cells (see PCT Patent Publication, WO 98/25598 and also U.S. Pat. No. 6,242,196 to Spiegelman). The activation of PPARγ by its natural and synthetic ligands has been reported to induce apoptosis in several tumor cell lines, including malignant B-lineage cells (Eucker et al., *Anticancer Drugs* 15(10):955-60 (2004)) and Waldenstrom's macroglobulinemia (Mitsiades et al., *Semin Oncol.* 30(2):309-12 (2003)). PPARγ agonists have also been reported to suppress liver carcinogenesis induced by diethylnitrosamine in rats (Guo et al., *World J Gastroenterol.* 0(23):3419-23 (2004)) and inhibit growth and metastasis of HT-29 human colon cancer cells through differentiation-promoting effects (Yoshizumi et al., *Int J Oncol.* 25(3):631-9 (2004)). The ligands of PPARγ also been reported inhibit growth of human esophageal carcinoma cells through induction of apoptosis and cell cycle arrest (Fujii et al., *Anticancer Res.* 24(3a): 1409-16 (2004)). PPARγ activation has also been reported to inhibit tumor progression in non-small-cell lung cancer. (Keshamouni et al., *Oncogene* 23(1):100-8 (2004)). In many instances, PPARγ therapy does not merely induce differentiation it induces apoptosis. Activation of PPARγ has such an effect on urological cancer cells (Yoshimura et al., *Int J Mol Med.* 12(6):861-5 (2003). PPARγ activators have also been reported to inhibit the growth of gastrointestinal, biliary, and pancreatic adenocarcinoma cells through activation of the peroxisome proliferator-activated receptor gamma/retinoid X receptor alpha pathway (Tsujie et al., *Exp Cell Res.* 289(1):143-51 (2003)). The use of PPARγ activators in the treatment of cancer is also disclosed in U.S. Pat. No. 6,294,559 to Smith et al. and U.S. Pat. No. 6,579,893 to Urban et al. and U.S. Patent Application Publication No. 20040162354 published on Aug. 19, 2004). The effects of PPARγ modulators on cell proliferation and cancer have also been observed for partial agonists such as troglitazone (see, U.S. Pat. No. 6,242,196) and U.S. Patent Application Publications Nos. 20040266834 and 20030032581.

More recently, the (−) isomers of halofenic acid and derivatives thereof which are particularly useful in the treatment of insulin resistance, Type II diabetes, obesity, and hyperuricemia (See, U.S. Pat. Nos. 6,646,004; 6,624,194; 6,613,802; and 6,262,118, each to Luskey et al. and also U.S. Patent Application Publication No. 20040029933 to Zhao et al.) have also been reported to be selective, partial PPARγ agonists with unexpectedly advantageous properties over their (+) isomers with respect to COX-1 inhibition, glucose lowering, and inhibition of Cytochrome P450 2C9. It has now been surprisingly found that these compounds are also useful in treating and preventing edema and the adverse health effects of edema.

PPARγ thus remains an important target for treating many hyperplastic and neoplastic disorders. However, what is needed in the art are new compounds and methods useful for modulating PPARγ in the treatment of hyperplastic and neoplastic disorders, including cancer, which avoid any such side effects of the PPARγ modulators while providing the benefits of PPARγ modulation in the treatment of these disorders. The present invention fulfills this and other needs by providing a selective, partial agonists of PPARγ with an improved side effect profile for use in treating these disorders.

BRIEF SUMMARY OF THE INVENTION

In one aspect, the invention relates to the finding that 3-trihalomethylphenoxy 4-halophenyl acetic acids (e.g., (−) halofenic acid or (−) (3-trifluoromethylphenoxy) (4-chlorophenyl)acetic acid (e.g., (−) halofenic acid)), their derivatives, analogs, and prodrugs thereof, while useful as partial agonists of PPARγ do not cause edema. In particular, the invention provides compounds of formula I, II, III, IVa, IVb, V, VI, and VII for use as edema-sparing PPARγ modulators. These compounds are particularly useful in treating conditions or subjects for which other PPARγ modulators are contra-indicated due to their potential to cause edema. Accordingly, the invention provides pharmaceutical compositions and methods of treatment based upon the use of these edema-sparing PPARγ modulators (i.e, the compounds of formula I, II, III, IVa, IVb, V, VI, and VII) in treating subjects or conditions whose conditions are rendered unsuitable for treatment with other PPARγ modulators due to the ability of these other PPARγ modulators to cause edema.

Accordingly, in one embodiment, the invention provides a method of treating a PPARγ-responsive condition or disease in a subject having edema, or is at increased risk of edema, comprising administering to a subject having the condition a compound of Formula I, II, III, IVa, IVb, V, VI, or VII in a therapeutically effective amount. In an exemplary embodiment, the condition is a neoplasia, and the edema-sparing PPARγ modulator is administered in an amount effective to inhibit growth of the neoplasia. In other embodiments, the invention further provides methods of treating a neoplasia by administering to the subject an agent selected from the group consisting of mitotic inhibitors, alkylating agents, antimetabolites, nucleic acid intercalating agents, topoisomerase inhibitors, agents which promote apoptosis, and agents which increase immune responses to tumors. The administering in any of the above embodiments, may be systemic or local, topical, intravenous, oral, or rectal. The neoplasia may be derived from an adipose cell or an adipose precursor cell or a liposarcoma. The neoplasia may be of a hemopoietic cell type or an hemopoietic precursor cell type, or of lymphoid or myeloid lineage. The neoplasia may be a lipoma, fibrolipoma, lipoblastoma, lipomatosis, hibernoma, hemangioma and liposarcoma. The neoplasia may be malignant. The neoplasia may be a sarcoma, carcinoma or leukemia.

In some embodiments, the neoplasia is a fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma, or a prostate, kidney, bladder or colon carcinoma.

In some embodiments, the condition may be osteoporosis, inflammation or allergy, eczema, acne vulgaris, or psoriasis. In other embodiments, the condition is cachexia, irritable bowel syndrome, inflammatory bowel disease, including Crohn's disease and ulcerative colitis, pancreatitis, abdominal obesity, neurodegenerative disease, or retinopathy.

In any of the above embodiments, the subject can be human. In other embodiments, the administered modulator is a compound of formula III, V, or VII. In some embodiments, the modulator is administered as the racemate or as a stereoisomer which is substantially free of other stereoisomers. The modulator is administered in therapeutically effective doses or amounts.

In other aspects, the invention provides a pharmaceutical composition comprising: (i) a compound of any one of Formula I, II, III, IVa, IVb, V, VI, or VII in a therapeutically effective amount to induce terminal differentiation of a PPARγ-responsive hyperproliferative cell in a human; and (ii) at least one agent selected from the group consisting of mitotic inhibitors, alkylating agents, antimetabolites, nucleic acid intercalating agents, topoisomerase inhibitors, agents which promote apoptosis, agents which increase immune responses to tumors; a MAP kinase inhibitor; and an RXR agonist wherein the agent is in a therapeutically effective amount, and (iii) a pharmaceutically acceptable carrier. The composition may be formulated as unit dose and contain from 100 to 800 mg of the compound.

The invention also relates to the surprising finding that 3-trihalomethylphenoxy 4-halophenyl acetic acids (e.g., (−) (3-trifluoromethylphenoxy) (4-chlorophenyl)acetic acid or (−) halofenic acid), their derivatives and prodrugs thereof, are useful as partial agonists of PPARγ with an improved side-effect profile with respect to adipogenesis or body fat changes, and weight gain.

Accordingly, the invention provides methods of treating a PPARγ-mediated condition by administering to a subject in need thereof a compound or a prodrug thereof. In one embodiment, the compound is a (−) isomer of a compound of Formula I:

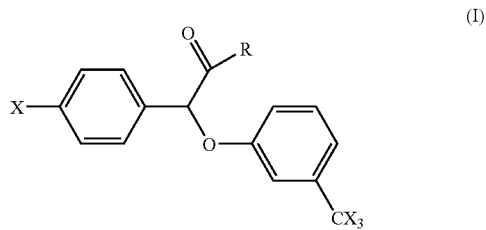

(I)

wherein R is a member selected from the group consisting of a hydroxy, alkoxy (e.g., $OCH_2CH_3$), heteroalkoxy (e.g., $OCH_2CH_2OCH_2CH_3$), aryloxy (e.g., $OC_6H_5$), heteroaryloxy (e.g., $OC_5H_4N$), lower aralkoxy, di-lower alkylamino-lower alkoxy, lower alkanamido lower alkoxy, benzamido-lower alkoxy, ureido-lower alkoxy, N'-lower alkyl-ureido-lower alkoxy, carbamoyl-lower alkoxy, halophenoxy substituted lower alkoxy, carbamoyl substituted phenoxy, carbonyl-lower alkylamino, N,N-di-lower alkylamino-lower alkylamino, halo substituted lower alkylamino, hydroxy substituted lower alkylamino, lower alkanolyloxy substituted lower alkylamino, ureido, arylsulfonamido (e.g., NHTs), alkylsulfonamido (e.g., NHMs) and lower alkoxycarbonylamino; and each X is independently a halogen; or a pharmaceutically acceptable salt thereof. Particularly preferred compounds of the above formula are set forth in U.S. Pat. Nos. 6,646,004; 6,624,194; 6,613,802; and 6,262,118 which are incorporated by reference herein with respect to such compound subject matter. Particularly preferred are prodrugs of (−) halofenic acid which therefore release (−) halofenic acid when administered to a subject.

In another embodiment, the compound is the (−) isomer of a compound of Formula II:

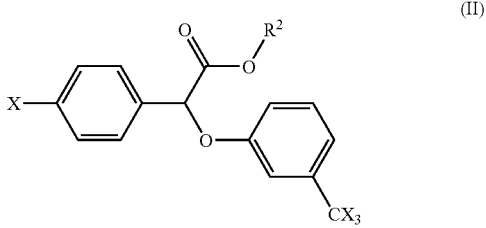

(II)

wherein $R^2$ is a member selected from the group consisting of alkyl, heteroalkyl, aryl, heteroaryl, phenyl-lower alkyl, lower alkanamido-lower alkyl, benzamido-lower alkyl, di-lower alkylamino-lower alkyl, ureido-lower alkyl, N'-lower alkyl-ureido-lower alkyl, carbamoyl-lower alkyl, halophenoxy substituted lower alkyl and carbamoyl substituted phenyl. Particularly preferred $R^2$ are those which readily undergo hydrolysis in vivo or when administered to a subject.

$R^2$ groups can also include, without limitation, the following: $C_1$-$C_5$ alkyl, $C_1$-$C_8$-cyclic alkyl, $C_2$-$C_5$ alkenyl, and $C_2$-$C_5$ alkynyl, wherein the groups are optionally substituted with one or more halogen atoms; phenyl, naphthyl and pyridyl, wherein the groups are optionally substituted with one or more substituents selected from the group consisting of halo, $C_1$-$C_4$ alkyl, $C_1$-$C_4$ alkoxy, $-NO_2$, $-S(O)_m(C_1$-$C_5$alkyl), $-OH$, $-NR^3R^4$, $-CO_2R^5$, $-CONR^3R^4$, $-NR^3COR^4$, $-NR^3CONR^3R^4$ and $-C_vF_w$; $-(CHR^3)R^4$; $-R^7OR^3$; $-R^7O_2CR^8NR^3R^4$, $-(CH_2)_oCH(R^3)(CH_2)_qO_2CR^9$; $-(CH_2)_oCH(R^3)(CH_2)_qNR^4COR9$; $-(CH_2)_oCH(R^3)(CH_2)_qNR^4CONR^3R^4$; $-(CH_2)_oCH(R^3)(CH_2)_qNR^4COOR^{10}$; $-(CH_2)_oCH(R^3)(CH_2)_qNR^4SO_2R^{11}$; $-(CHR^3)_sCO_2R^{12}$; $-(CHR^3)_pNR^3R^4$; $-(CHR^3)_sCONR^{13}R^{14}$

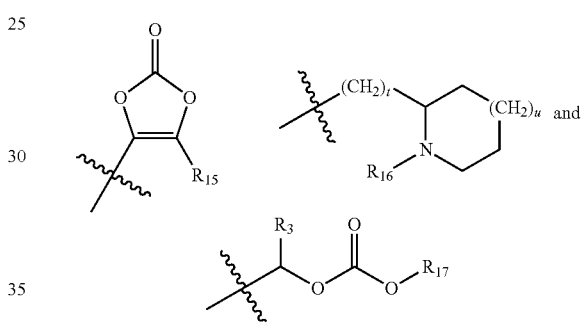

Subscripts m, o, q, s, t, u, v and w are integers as follows: m is 0 to 2; o and q are 0 to 5; p is 1 to 5; s is 1 to 3; t is 1 to 5; u is 0 to 1; v is 1 to 3; and w is 1 to (2v+1). $R^3$ and $R^4$ are independently H, $C_1$-$C_5$ alkyl, phenyl or benzyl. $R^5$ is H, $C_1$-$C_5$ alkyl or $NR^3R^4$. $R^6$ is phenyl, naphthyl, pyridyl, imidazolyl, indoxyl, indolizinyl, oxazolyl, thiazolyl, pyrimidyl, or 1-pyrazolyl optionally substituted with one or more substituents selected from the group consisting of halo, $C_1$-$C_4$ alkyl, $C_1$-$C_4$ alkoxy, $-NO_2$, $-S(O)_m(C_1$-$C_5$alkyl), $-OH$, $-NR^3R^4$, $-CO_2R^5$, $-CONR^3R^4$, $-NR^3COR^4$, $-NR^3CONR^3R^4$ and $-C_vF_w$. $R^7$ is a $C_1$-$C_8$ saturated or unsaturated, straight-chain, branched or cyclic alkylene or alkylidene group optionally substituted with one or more groups selected from halo, hydroxyl, thiol, amino, monoalkyl amino, dialkyl amino, acylamino, carboxyl, alkylcarboxyl, acyl, aryl, aroyl, aralkyl, cyano, nitro, alkoxy, alkenyloxy, alkylcarbonyloxy and arylcarbonyloxy. $R^8$ is a $C_1$-$C_8$ straight-chain or branched alkylene or alkylidene optionally substituted with one or more groups selected from amino, monoalkyl amino, dialkyl amino, acylamino, hydroxyl, thiol, methylthiol, carboxyl and phenyl. $R^9$ and $R^{10}$ are independently H, $C_1$-$C_5$ alkyl, optionally substituted with one or more groups consisting of $C_1$-$C_5$ alkoxy aryl and heteroaryl, wherein the aryl is phenyl or naphthyl optionally substituted with one or more substituents selected from the group consisting of halo, $C_1$-$C_4$ alkyl, $C_1$-$C_4$ alkoxy, $-NO_2$, $-S(O)_m(C_1$-$C_5$alkyl), $-OH$, $-NR^3R^4$, $-CO_2R^5$, $-CONR^3R^4$, $-NR^3COR^4$, $-NR^3CONR^3R^4$ and $-C_vF_w$, and wherein the heteroaryl is pyridyl optionally substituted with one or more substituents selected from the group consisting of halo, $C_1$-$C_4$ alkyl, $C_1$-$C_4$ alkoxy, $-NO_2$, $-S(O)_m(C_1$-$C_5$alkyl), —OH, —NR³R⁴, —CO₂R⁵, —CONR³R⁴, —NR³COR⁴, —NR³CONR³R⁴ and —C_vF_w. R¹¹ is methyl or phenyl, wherein the phenyl is optionally substituted with methyl and/or —NO₂. R¹² is H, C₁-C₅ alkyl, phenyl, benzyl, naphthyl or pyridyl, wherein the C₁-C₅ alkyl, phenyl, naphthyl, benzyl and pyridyl are optionally substituted with one or more substituents selected from the group consisting of halo, C₁-C₄ alkyl, C₁-C₄ alkoxy, —NO₂, —S(O)_m(C₁-C₅alkyl), —OH, —NR³R⁴, —CO₂R₅, —CONR³R⁴, —NR³COR⁴, —NR³CONR³R⁴ and —C_vF_w. R¹³ and R¹⁴ are independently the following: alkyl, alkenyl, aryl, aralkyl or cycloalkyl, wherein the groups are optionally substituted with one or more substituents selected from the group consisting of halo, C₁-C₄ alkyl, C₁-C₄ alkoxy, —NO₂, —S(O)_m(C₁-C₅alkyl), —OH, —NR³R⁴, —CO₂R⁵, —CONR³R⁴, —NR³COR⁴, —NR³CONR³R⁴, —CH₂NR³R⁴, OOCR¹⁸ and —C_vF_w; and wherein R¹³ and R¹⁴ are included as —(CHR₃)CONR¹³R¹⁴, NR¹³R¹⁴ is

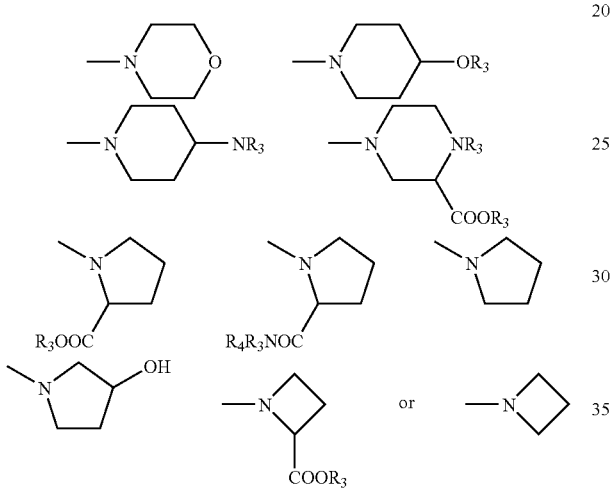

R¹⁵ is C_vF_w or C₁-C₅ alkyl, wherein C₁-C₅ alkyl is optionally substituted with the following substituents: C₁-C₅ alkoxy; phenyl, optionally substituted with one or more substituents selected from the group consisting of halo, C₁-C₄ alkyl, C₁-C₄ alkoxy, —NO₂, —S(O)_m(C₁-C₅alkyl), —OH, —NR³R⁴, —CO₂R⁵, —CONR³R⁴, —NR³COR⁴, —NR³CONR³R⁴ and —C_vF_w; benzyl, optionally substituted with one or more substituents selected from the group consisting of halo, C₁-C₄ alkyl, C₁-C₄ alkoxy, —NO₂, —S(O)_m (C₁-C₅alkyl), —OH, —NR³R⁴, —CO₂R⁵, —CONR³R⁴, —NR³COR⁴, —NR³CONR³R⁴ and —C_vF_w. R¹⁶ is H, C₁-C₅ alkyl or benzyl. R¹⁷ is C₁-C₅ alkyl, C₃-C₈ cyclic alkyl, phenyl or benzyl. R¹⁸ is H, alkyl, aryl, aralkyl or cycloalkyl, where the group is optionally substituted with one or more substituents selected from the group consisting of halo, C₁-C₄ alkyl, C₁-C₄ alkoxy, —NO₂, —S(O)_m(C₁-C₅alkyl), —OH, —NR³R⁴, —CO₂R⁵, —CONR³R⁴, —NR³COR⁴, —NR³CONR³R⁴ and —C_vF_w. Particularly preferred compounds of the above formula and methods for making such compounds are taught in U.S. Patent Application Publication No. 20030220399 which is incorporated herein by reference and in particularity with respect to such subject matter.

In an exemplary embodiment, the compound to be administered according to the invention is (–) 2-acetamidoethyl 4-chlorophenyl-(3-trifluoromethylphenoxy)acetate (i.e., (–) halofenate)), a compound of Formula III:

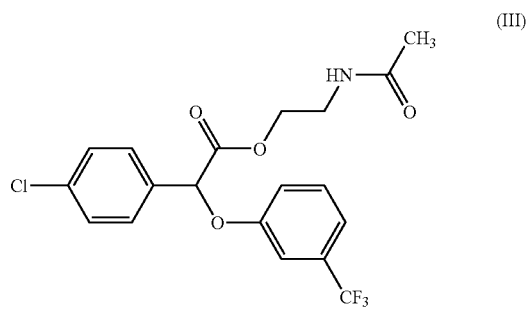

In some embodiments, the compound of Formula III is administered in the form of a composition which contains the (–) stereoisomer of halofenate and which is substantially free of its (+) stereoisomer.

In yet other embodiments, the compound is a compound of formula IV:

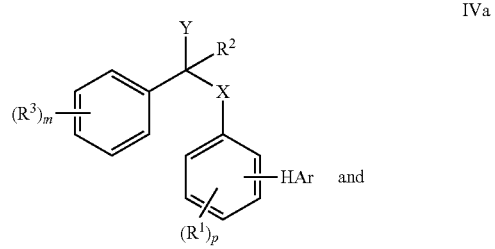

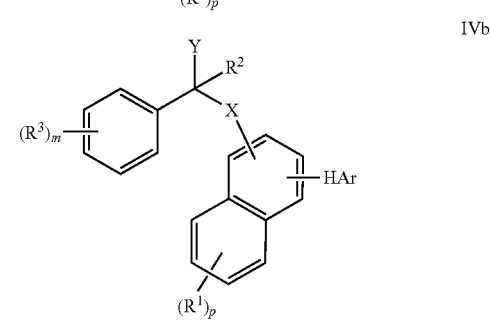

in which the letter X is selected from O, S, SO, SO₂ and NR, wherein R is H, (C₁-C₈)alkyl, COR^a, COOR^a and CONR^aR^b wherein R^a and R^b are each independently selected from H and (C₁-C₈)alkyl; the letter Y represents CH₂OR^c, CO₂R^c, CHO, CONR^cR^m, CH(=NR^c), CH(=NOR^c) or a carboxylic acid surrogate, wherein R^c is selected from H, (C₁-C₈)alkyl, (C₃-C₈)alkenyl, (C₃-C₈)alkynyl, (C₃-C₇)cycloalkyl, (C₄-C₈) cycloalkyl-alkyl, aryl, aryl(C₁-C₈)alkyl and (C₁-C₈)alkylene-Z, wherein Z is selected from COR^d, COOR^d, NR^dR^e, NR^dCONR^eR^f, NR^dCOR^e, NR^dCOOR^e and CONR^dR^e wherein R^d, R^e and R^f are each independently selected from H, (C₁-C₈)alkyl and phenyl, or optionally two of R^d, R^e and R^f when attached to the same nitrogen atom are combined to form a five- or six-membered ring; and wherein R^m is selected from H, (C₁-C₈)alkyl, aryl, OH and SO₂R^n, wherein R^n is selected from (C₁-C₈)alkyl, (C₁-C₈)haloalkyl, (C₁-C₈) aralkyl, (C₂-C₈)heteroalkyl, aryl, heteroaryl, (C₁-C₈)alkoxy, aryloxy, alkylamino, dialkylamino, arylamino, diarylamino, haloalkylamino and di(haloalkyl)amino, and R^m and R^c are optionally combined with the nitrogen atom to which each is attached to form a five- or six-membered ring.

HAr represents a heteroaryl moiety, optionally substituted with from one to three substituents independently selected from halogen, hydroxy, (C₁-C₈)alkyl, aryl(C₁-C₈)alkyl, (C₁-

$C_8$)alkoxy, $(C_2-C_8)$alkenyl, $(C_2-C_8)$alkynyl, $(C_3-C_7)$cycloalkyl, $(C_4-C_8)$cycloalkyl-alkyl, $(C_1-C_8)$heteroalkyl, $(C_2-C_5)$heterocyclyl, aryl, aryloxy, heterosubstituted $(C_3-C_7)$cycloalkyl, heteroalkyl substituted $(C_3-C_7)$cycloalkyl, $(C_1-C_8)$haloalkyl, $O(C_1-C_8)$haloalkyl, nitro, cyano, $CO_2R^g$, $COR^g$, $NR^gR^h$, $S(O)_qR^g$, $SO_2NR^gR^h$, $NR^gCONR^hR^i$, $NR^g$-$COR^h$, $NR^gCOOR^h$ and $CONR^gR^h$, wherein $R^g$, $R^h$ and $R^i$ are each independently selected from H and $(C_1-C_8)$alkyl, or optionally two of $R^g$, $R^h$ and $R^i$ when attached to the same nitrogen atom are combined to form a five- or six-membered ring, and the subscript q is an integer of from 0 to 2.

A variety of heteroaryl groups provide compounds having the desired activity. In particular, the heteroaryl groups can be monocyclic or fused bicyclic heteroaryl groups. More particularly, one group of suitable monocyclic heteroaryl groups are provided in FIG. 1A. In this Figure, the line extending from the ring indicates the point of attachment to the remainder of the compound and can be made through any available valence on the ring. Other examples of heteroaryl groups are provided in FIG. 1B, which illustrates preferred fused-bicyclic heteroaryl groups, wherein attachment to the remainder of the compound can take place through an available valence on either ring.

Returning to formulae IVa and IVb, the subscripts m and p indicate the presence of substituents on their respective rings, wherein each substituent present can be the same or different from any other substituent. More particularly, the subscript m is an integer of from 0 to 4, and the subscript p is an integer of from 0 to 3. More preferably the subscript m is an integer of from 0 to 3, and the subscript p is an integer of from 0 to 3. Still more preferably, the subscript m is an integer of from 0 to 2, and the subscript p is an integer of from 0 to 2. Most preferably, the subscript m is 0, 1 or 2 and the subscript p is 1 or 2.

Each $R^1$ and $R^3$ represents a substituent independently selected from halogen, hydroxy, $(C_1-C_8)$alkyl, $(C_2-C_8)$alkenyl, $(C_2-C_8)$alkynyl, $(C_1-C_8)$alkoxy, $(C_3-C_7)$cycloalkyl, $(C_4-C_8)$cycloalkyl-alkyl, $(C_1-C_8)$haloalkyl, $(C_1-C_8)$heteroalkyl, $(C_2-C_5)$heterocyclyl, heterosubstituted $(C_3-C_7)$cycloalkyl, heteroalkyl substituted $(C_3-C_7)$cycloalkyl, $O(C_1-C_8)$haloalkyl, nitro, cyano, phenyl, O-phenyl, $NR^j$-phenyl, $S(O)_r$-phenyl, $COR^j$, $COOR^j$, $NR^jR^k$, $S(O)_rR^j$, $SO_2NR^jR^k$, $NR^jCONR^kR^l$, $NR^jCOR^k$, $NR^jCOOR^k$ and $CONR^jR^k$ wherein the phenyl ring is optionally substituted and $R^j$, $R^k$ and $R^l$ are each independently selected from H, $(C_1-C_8)$alkyl and $(C_1-C_8)$haloalkyl, or optionally two of $R^j$, $R^k$ and $R^l$ when attached to the same nitrogen atom are combined to form a five- or six-membered ring, and the subscript r is an integer of from 0 to 2. The subscript m is an integer of from 0 to 4 and the subscript p is an integer of from 0 to 3.

The symbol $R^2$ represents a member selected from H, $(C_1-C_8)$alkyl, $(C_1-C_8)$haloalkyl, $(C_1-C_8)$aralkyl and $(C_1-C_4)$alkylene-Z, wherein Z is as defined above.

In one embodiment, the compound is a compound of formula V:

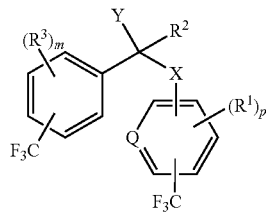

Formula V which includes the racemate or a substantially purified composition of either isomer thereof:

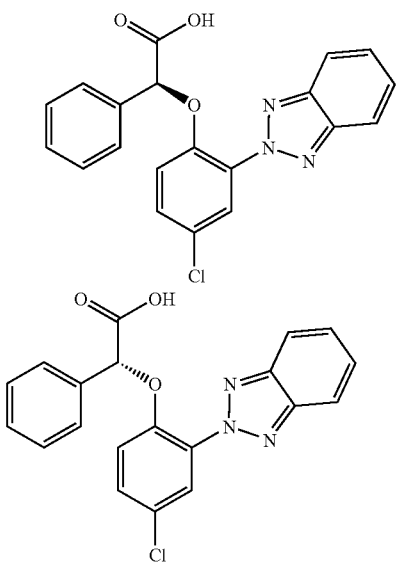

In another set of embodiments, the edema-sparing PPARγ modulator for use according to the invention is a compound of formula VI:

Formula VI or a pharmaceutically acceptable salt thereof, wherein the letter X represents a member selected from the group consisting of O, S, SO, $SO_2$, CHR and NR, wherein R is H, $(C_1-C_8)$alkyl, $COR^a$, $COOR^a$ and $CONR^aR^b$ wherein $R^a$ and $R^b$ are each independently selected from the group consisting of H and $(C_1-C_8)$alkyl; the letter Y represents a member selected from the group consisting of $CH_2OR^c$, $CO_2R^c$, tetrazole, CHO, $CONR^cR^m$, $CH(=NR^c)$ and $CH(=NOR^c)$, wherein $R^c$ is a member selected from the group consisting of H, $(C_1-C_8)$alkyl, $(C_3-C_8)$alkenyl, $(C_3-C_8)$alkynyl, $(C_3-C_7)$cycloalkyl, $(C_4-C_8)$cycloalkyl-alkyl, aryl, aryl$(C_1-C_8)$alkyl and $(C_1-C_8)$alkylene-Z, wherein Z is selected from the group consisting of $COR^d$, $COOR^d$, $NR^dR^e$, $NR^dCONR^eR^f$, $NR^d$-$COR^e$, $NR^dCOOR^e$ and $CONR^dR^e$ wherein $R^d$, $R^e$ and $R^f$ are each independently selected from the group consisting of H, $(C_1-C_8)$alkyl and phenyl, or optionally two of $R^d$, $R^e$ and $R^f$ when attached to the same nitrogen atom are combined to form a five- or six-membered ring; and wherein $R^m$ is selected from the group consisting of H, $(C_1-C_8)$alkyl, aryl and OH, and $R^m$ and $R^c$ are optionally combined with the nitrogen atom to which each is attached to form a five or six membered ring; each of the symbols $R^1$ and $R^3$ represents a member independently selected from the group consisting of halogen, hydroxy, $(C_1-C_8)$alkyl, $(C_2-C_8)$alkenyl, $(C_2-C_8)$alkynyl, $(C_1-C_8)$alkoxy, $(C_3-C_7)$cycloalkyl, $(C_4-C_8)$cycloalkyl-alkyl, $(C_1-$ $C_8$)haloalkyl, ($C_1$-$C_8$)heteroalkyl, ($C_2$-$C_5$)heterocyclyl, heterosubstituted ($C_3$-$C_7$)cycloalkyl, heteroalkyl substituted ($C_3$-$C_7$)cycloalkyl, O($C_1$-$C_8$)haloalkyl, nitro, cyano, phenyl, O-phenyl, $NR^j$-phenyl, S(O)$_r$-phenyl, $COR^j$, $COOR^j$, $NR^jR^k$, S(O)$_rR^j$, $SO_2NR^jR^k$, $NR^jCONR^kR^l$, $NR^jCOR^k$, $NR^jCOOR^k$ and $CONR^jR^k$ wherein the phenyl ring is optionally substituted and $R^j$, $R^k$ and $R^l$ are each independently selected from the group consisting of H and ($C_1$-$C_8$)alkyl, including ($C_1$-$C_8$)haloalkyl, or optionally two of $R^j$, $R^k$ and $R^l$ when attached to the same nitrogen atom are combined to form a five- or six-membered ring, and the subscript r is an integer of from 0 to 2; the symbol $R^2$ represents a member selected from the group consisting of H and ($C_1$-$C_8$)alkyl; the letter Q represents CH or N; the subscript m is an integer of from 0 to 3; and the subscript p is an integer of from 0 to 2.

Turning first to the linkage provided in formula 1 as X, preferred groups are O, S and NR. In one group of embodiments, X is O. In another group of embodiments, X is NR, preferably wherein R is H or ($C_1$-$C_4$)alkyl.

Preferred groups for Y include $CH_2OR^c$, $CO_2R^c$, tetrazole, CHO and $CONR^cR^m$; with $CH_2OR^c$, $CO_2R^c$ and tetrazole being further preferred. The most preferred embodiments are those in which Y is $CH_2OR^c$ or $CO_2R^c$.

Preferred groups for $R^1$ and $R^3$ are halogen, ($C_1$-$C_8$)alkyl, ($C_1$-$C_8$)alkoxy, ($C_3$-$C_7$)cycloalkyl, ($C_4$-$C_8$)cycloalkyl-alkyl, ($C_1$-$C_8$)haloalkyl, O($C_1$-$C_8$)haloalkyl, nitro, phenyl, O-phenyl, $NR^j$-phenyl, $NR^jCOR^k$, S(O)$_r$-phenyl and S(O)$_rR^j$. Particularly preferred groups for $R^1$ and $R^3$ are halogen, ($C_1$-$C_8$) alkyl, ($C_1$-$C_8$)haloalkyl, nitro, O-phenyl, $NR^jCOR^k$ and S(O)$_rR^j$. Still further preferred groups for $R^1$ and $R^3$ are F, Cl, ($C_1$-$C_4$)alkyl, $CF_3$, $NHCOCF_3$, $NO_2$, $SCH_3$ and $OC_6H_4CF_3$.

The substituent $R^2$ is preferably H or ($C_1$-$C_4$)alkyl, more preferably H or $CH_3$. In the most preferred embodiments, $R^2$ is H.

The letter Q is preferably CH.

The subscript m is preferably 0 to 2. In one group of embodiments, m is 0. In another group of embodiments, m is 1. In yet another group of embodiments, m is 2.

The subscript p is 0 to 2. In one group of embodiments, p is 0. In another group of embodiments, p is 1. In yet another group of embodiments, p is 2.

Within the above groups of embodiments, certain combinations are also preferred. Turning first to the embodiments in which Q is CH, X is preferably O, S or NR. Still further preferred are those embodiments in which Y is $CO_2R^c$. Even further preferred are those embodiments in which m is 0 to 2 and p is 0 to 1. Within the group of embodiments in which Q is CH, X is O, S or NR, Y is $CO_2R^c$, m is 0 to 2 and p is 0 to 1, the symbol $R^1$ will preferably represent halogen, nitro, ($C_1$-$C_8$)alkyl, ($C_1$-$C_8$)alkoxy, or ($C_1$-$C_8$)haloalkyl. Returning to the group of embodiments in which Q is CH, X is O, S or NR, Y is $CO_2R^c$, m is 0 to 2 and p is 0 to 1, the symbol $R^3$ will preferably represent halogen, nitro, ($C_1$-$C_8$)alkyl, ($C_1$-$C_8$)alkoxy, or ($C_1$-$C_8$)haloalkyl. For those embodiments in which two $R^3$ groups are present, it is understood that each $R^3$ group is independently selected from the provided list. For each of these groups of embodiments, including those in which $R^1$ and $R^3$ are provided with their full scope according to formula I above, the symbol $R^c$ is preferably H, ($C_1$-$C_8$)alkyl or ($C_1$-$C_8$)alkylene Z. Further preferred are those embodiments in which $R^2$ is H or $CH_3$.

In one group are particularly preferred embodiments, Q is CH; X is selected from the group consisting of O and NR; Y is selected from the group consisting of $CH_2OR^c$ and $CO_2R^c$; the subscript m is 0 to 2 and the subscript p is 0 to 1; each $R^1$ is selected from the group consisting of halogen, nitro, ($C_1$-$C_8$) alkyl and ($C_1$-$C_8$) alkoxy; each $R^3$ is selected from the group consisting of halogen, nitro, ($C_1$-$C_8$) alkyl and ($C_1$-$C_8$) alkoxy; and $R^2$ is H or $CH_3$. Selected groups of embodiments within the above are those in which (i) X is O and Y is $CO_2R^c$; (ii) X is O and Y is $CH_2OR^c$; (iii) X is NH and Y is $CO_2R^c$; (iv) X is NH and Y is $CH_2OR^c$. Still further preferred embodiments for each of these group are those in which $R^1$ and $R^3$ are selected from F, Cl, ($C_1$-$C_4$)alkyl, $CF_3$, $NHCOCF_3$, $NO_2$, $SCH_3$ and $OC_6H_4$—$CF_3$.

The compounds of formula VI correspond to those disclosed in PCT Application Publication No. WO/2005/080340 and U.S. Patent Application Publication No. 20050222213 which are each incorporated herein by reference in its entirety, with particular regard to the PPARγ modulators disclosed therein and methods of making and using same.

Compounds of formula VI include the following compounds:

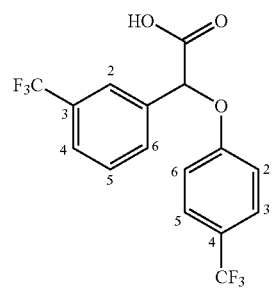

39

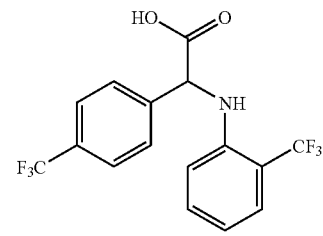

40

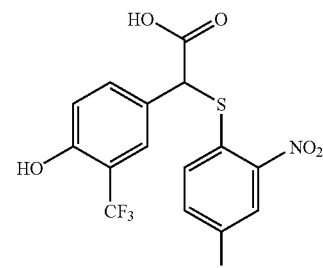

41

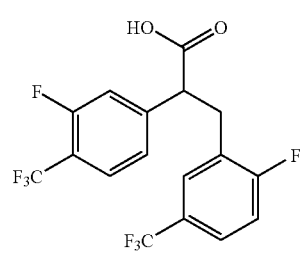

42

43 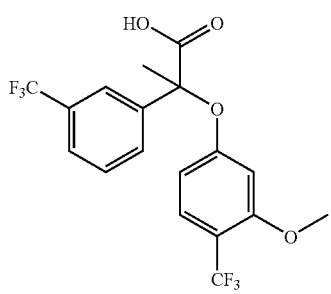
44 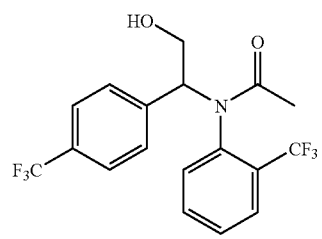
45 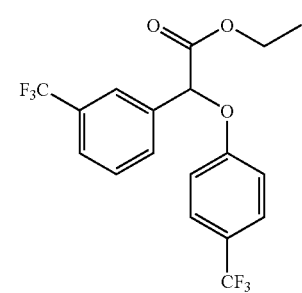
81 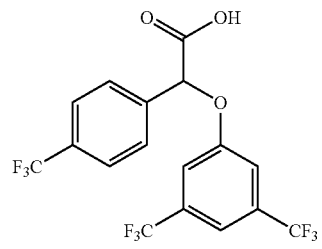
82 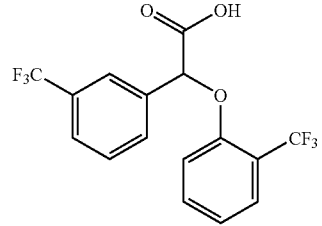
83 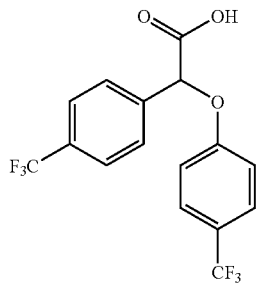
84 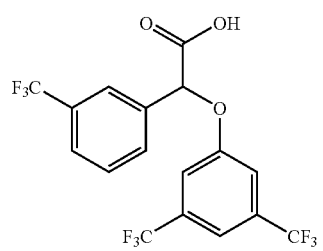
85 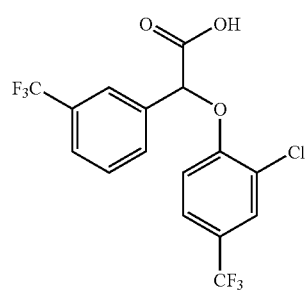
86 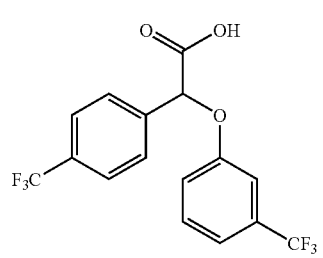
87 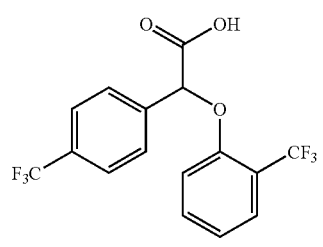
88 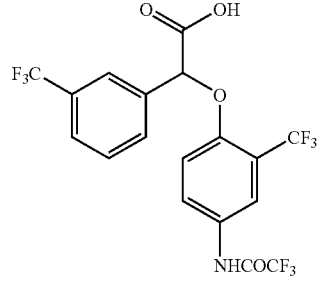
89 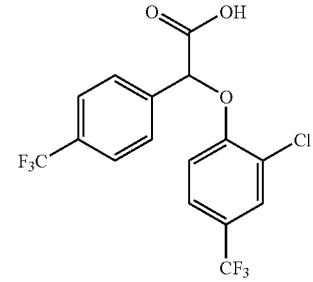

-continued

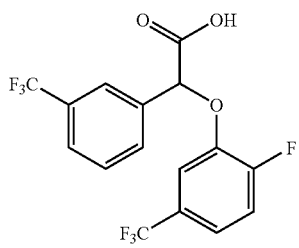
90

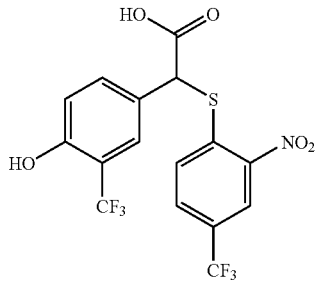
41

In one embodiment, the compound is a compound of formula VII, including the pharmaceutically acceptable salts and prodrugs thereof, including, particularly, ester prodrugs thereof which readily hydrolyze in vivo to release a compound of formula VII:

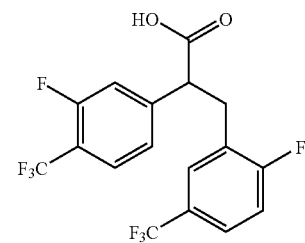
42

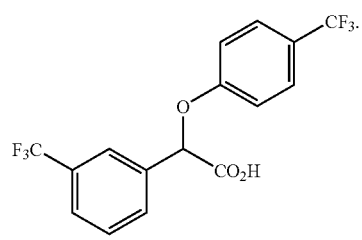
Formula VII

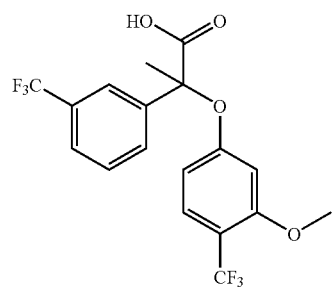
43

The compound of formula VII may be used as the racemate or either enantiomer which is in a composition that is substantially free of the opposite enantiomer thereof.

The compounds of formula I, II, III, IVa or IVb, V, VI, and VII are compounds to be administered according to the invention. These compounds include all salts and polymorphs and solvates thereof, and particularly, pharmaceutically acceptable salts thereof. Still further, the invention includes compounds that are single isomers of the above formula (e.g., single enantiomers of compounds having a single chiral center), as well as prodrug forms thereof.

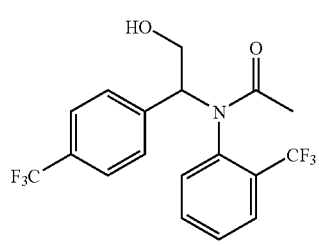
44

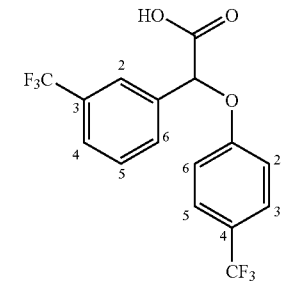
39

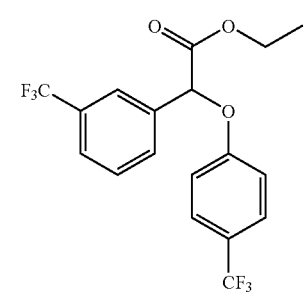
45

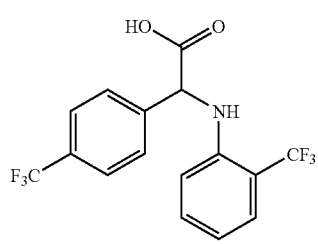
40

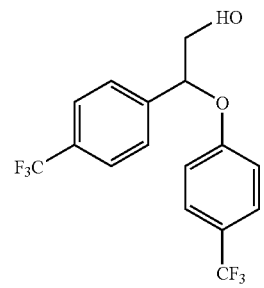
128

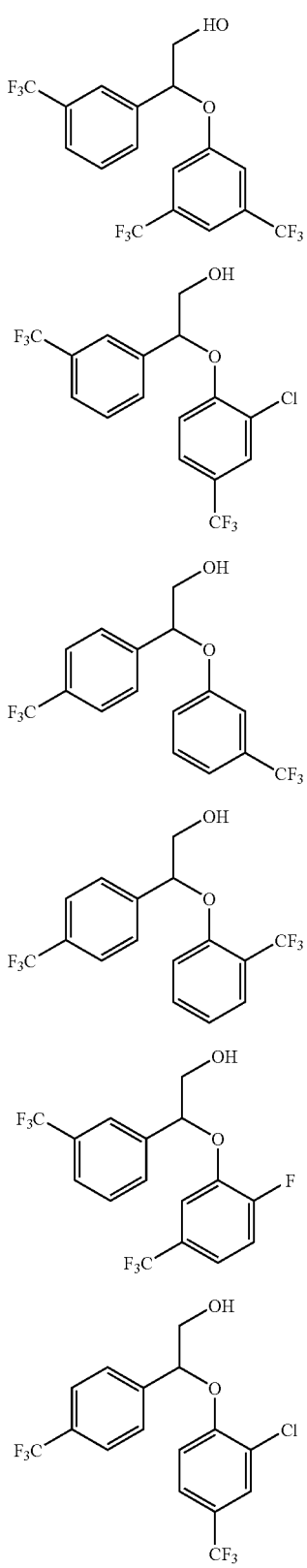

The compounds of formula I, II, III, IVa or IVb, V, VI, and VII are compounds to be administered according to the invention. These compounds include all salts and polymorphs and solvates and stereoisomers thereof, and particularly, pharmaceutically acceptable salts thereof. Still further, the invention includes compounds that are single isomers of the above formula (e.g., single enantiomers of compounds having a single chiral center), as well as prodrug forms thereof.

The above compounds have many therapeutic applications in treating edema and other edematious diseases as well as in PPARγ-mediated diseases. Diseases, risk factors, and conditions mediated by PPAR gamma include type I diabetes, type 2 or non-insulin dependent diabetes, syndrome X, (including metabolic syndrome), insulin resistance, heart failure, dyslipidemia including diabetic dyslipidemia and mixed dyslipidemia, hyperlipidemia, hypercholesterolemia, hypertension and cardiovascular disease, including atherosclerosis, arteriosclerosis and hypertriglyceridemia, epithelial hyperproliferative diseases including eczema and psoriasis and conditions associated with the lung and gut, osteoporosis, acne, cancer, and eating disorders or conditions such as obesity, bulimia, and anorexia nervosa. In some embodiments, the invention provides method of treating or preventing diseases or conditions susceptible to therapy with a PPARγ modulator according to the present invention. Such conditions include, but are not limited to, cachexia, irritable bowel syndrome, inflammatory bowel disease, including Crohn's disease and ulcerative colitis, other inflammatory conditions, pancreatitis, abdominal obesity, neurodegenerative disease, retinopathy, neoplastic conditions, adipose cell tumors, adipose cell carcinomas, such as liposarcoma, prostate cancer and other cancers, including gastric, breast, bladder and colon cancers, angiogenesis, Alzheimer's disease, psoriasis, acne vulgaris, and skin diseases modulated by PPAR, and high blood pressure. In some further embodiments, the PPARγ modulator of any of Formulae III or V or VII.

Accordingly, in a first aspect, the invention provides methods of treating PPARγ-responsive hyperproliferative cells, cancer, hyperplasias, or neoplasms by administering a phenoxyacetic acid PPARγ modulator to a subject in need of such treatment. The invention also provides pharmaceutical compositions of phenoxyacetic acid modulators for use in treating PPARγ-responsive hyperproliferative cells, cancers, hyperplasia and neoplasms. In a related aspect, the invention provides a method for inhibiting proliferation of a PPARγ-responsive hyperproliferative cell by contacting the cell with a compound of Formula I, II, III, IVa, IVb, V, VI, or VII. The compound can be administered in a therapeutically effective amount to induce differentiation of the hyperproliferative cell and/or to inhibit cell growth and proliferation. In preferred embodiments, phenoxyacetic acid compound is a compound of Formulae I, II, III, Iva, IVb, V, VI, or VII. Preferably, the phenoxyacetic acid compound of formula I, II, or III is an enantiomer whose configuration corresponds to the (−) isomer configuration of the halofenic acid moiety.

In some embodiments, the phenoxyacetic acid PPARγ modulator can be administered to subjects to treat sarcomas, carcinomas and/or leukemias. Exemplary disorders for which halofenate can be administered include: fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma.

In further embodiments, the edema-sparing PPARγ modulator can be administered to subjects to treat carcinomas forming from tissue of the breast, prostate, kidney, bladder or colon.

In other embodiments, the edema sparing PPARγ modulator is administered to treat breast adenocarcinomas and advanced metastatic breast tumors.

In other embodiments, the edema-sparing PPARγ modulator is administered to treat adipose cell tumors or any of the major histologic types of human liposarcoma.

In still other embodiments, edema-sparing PPARγ modulator can be administered to treat subjects having hyperplastic or neoplastic disorders arising in adipose tissue. These disorders include, but are not limited to, adipose cell tumors (e.g., lipomas, fibrolipomas, lipoblastomas, lipomatosis, hibernomas, hemangiomas and/or liposarcomas).

In yet other embodiments, edema-sparing PPARγ modulator can be administered to treat hyperplastic or neoplastic disorders of the hematopoietic system (e.g., leukemic cancers). In other embodiments, the condition to be treated is human multiple myeloma and Waldenstrom's macroglobulinemia.

In still other embodiments, edema-sparing PPARγ modulator is administered to treat mesenchymal tumors. These tumors include, but nor limited to, sarcomas (general), rhabdomyosarcomas, fibrosarcomas, retinoblastoma, hemangiopericytoma, congenital mesoblastic nephroma, and mesotheliomas.

The edema-sparing PPARγ modulator can be administered by a variety of routes and dosage regimens. The phenoxyacetic acid compound of any one of Formulae I to VII can be administered alone, or as part of a combination therapy with a second agent according to the condition or disease to be treated. Exemplary second agents include mitotic inhibitors, alkylating agents, antimetabolites, RXR modulators, MAP kinase inhibitors (e.g., PD098059 (Parke-Davis), nucleic acid intercalating agents, topoisomerase inhibitors, agents which promote apoptosis, and/or agents which increase immune responses. In other embodiments, the edema-sparing PPARγ modulator can be administered with an RXR agonist. Such RXR agonist can be natural or synthetic retinoids.

Still another aspect of the present invention provides compositions and kits for administering edema-sparing PPARγ modulator and the at least one second agent (e.g., RXR agonist, MAP kinase inhibitor). For example, both the edema-sparing PPARγ modulator and second agent(s) can be premixed, preferably in a pharmaceutically acceptable carrier. Alternatively, the edema-sparing PPARγ modulator and second agent(s) can be provided separately in the form of a kit comprising (i) a first pharmaceutical composition including edema-sparing PPARγ modulator in a pharmaceutically acceptable carrier, and (ii) a second pharmaceutical composition including the second agent in a pharmaceutically acceptable carrier, the edema-sparing PPARγ modulator and second agent being present in a therapeutically effective amount to, upon administration, to induce terminal differentiation or reduce proliferation of a PPARγ-responsive hyperproliferative cell in the subject.

In each of the above embodiments, the phenoxyacetic acid PPARγ modulator can be a compound of any one of Formula I, II, III, IVa, IVb, V, VI and VII. In some embodiments, the compound is a compound of Formula III or V.

In another aspect, the invention is directed to a method for treating a subject having, or susceptible to having inflammation, an immune disorder, a type I hypersensitivity, asthma or allergy, comprising administering to said subject a therapeutically effective amount of a phenoxyacetic acid modulator of PPARγ. In one embodiment, the subject has one or more symptoms selected from the group consisting of an increase in $T_{H2}$ type cytokines, lung airway inflammation, eosinophil infiltration, mucous production in the lung, airway hyperreactivity (AHR) and elevated serum IgE levels. In each of the above embodiments, the phenoxyacetic acid PPARγ modulator can be a compound of any one of Formula I, II, III, IVa, IVb, V, VI, and VII. In some embodiments, the compound is a compound of Formula III or V.

In another aspect, the invention is directed to a method for treating a subject having, or susceptible to having osteoporosis (including, but not limited to retrograde osteoporosis) or psoriasis comprising administering to said subject a therapeutically effective amount of a phenoxyacetic acid modulator of PPARγ. The phenoxyacetic acid PPARγ modulator can be a compound of any one of Formula I, II, III, IVa, IVb, V, VI, and VII. In some embodiments, the compound is a compound of Formula III or V or VII.

In each of the above aspects and embodiments, there are further embodiments, wherein the subject to be treated has or has had edema, or has a condition which can contribute to edema, or is otherwise in need of treatment for edema or susceptible to edema due to the health condition to be treated or due to side effects of another drug therapy.

In another aspect, the invention provides a method for treating one or more conditions selected from excess fluid retention, peripheral edema, and pulmonary edema by administering to a subject in need thereof a compound of any one of Formula I, II, III, IVa, IVb, V, VI, or VII. In some embodiments, the invention provides a method for treating or preventing one or more conditions which cause edema or are exacerbated by edema (e.g., congestive heart failure, hypertension, angina, cardiac insufficiency, coronary vasospasm, cardiac ischemia, liver cirrhosis, hyponatremia, renal vasospasm, renal failure, diabetic nephropathy, cerebral edema, cerebral ischemia, stroke, and thrombosis) by administering to a subject in need thereof a compound of any one of Formula I, II, III, IVa, IVb, V, VI, or VII.

The subject is a mammal having the condition or disease to be treated or at a known elevated risk of occurrence or recurrence of the condition to be treated. The term "mammal" includes, without limitation, humans, domestic animals (e.g., dogs or cats), farm animals (cows, horses, or pigs), monkeys, rabbits, mice, and laboratory animals. Preferably, the subject is human. In some embodiments, the subject is a human with one or more of obesity, NIDDM, hypertension, edema, hypertension, or heart failure.

In another aspect, the invention provides modulators of PPARγ which are useful in treating one or more of the above conditions. In some embodiments, the compound for use according to the invention is a partial agonist of PPARγ. In related embodiments, the compound is a compound which is a PPARγ partial agonist and is of the Formulae I, II, III, Iva, IVb, V, VI, or VII. In further embodiments, the compound is a partial PPARγ agonist which has less than 50%, 25%, or 10% of the agonist activity as a full PPARγ agonists or which can antagonize up to 50%, 75% or 90% of the agonist activity of a full PPARγ agonist.

In another aspect, without intending to be bound by theory, the invention provides methods of identifying a compound for use according to the invention by first screening the compound for PPARγ modulatory activity and selecting compounds behaving as partial agonists of PPARγ for further testing for their anti-edema activity in a suitable animal model or clinical trial. In related embodiments, the compound is a compound which is a PPARγ partial agonist and is of the Formulae I, II, III, Iva, IVb, V, VI, or VII. In additional embodiments, the compound is a partial PPARγ agonist which has less than 50%, 25%, or 10% of the agonist activity as a full PPARγ agonists or which can antagonize up to 50%, 75% or 90% of the agonist activity of a full PPARγ agonist. Both halofenic acid and the compound of Formula V are partial PPARγ agonists. In other embodiments, the compound can be directly screened for anti-edema activity in a suitable animal or clinical model.

DETAILED DESCRIPTION OF THE INVENTION

Figure 1A:
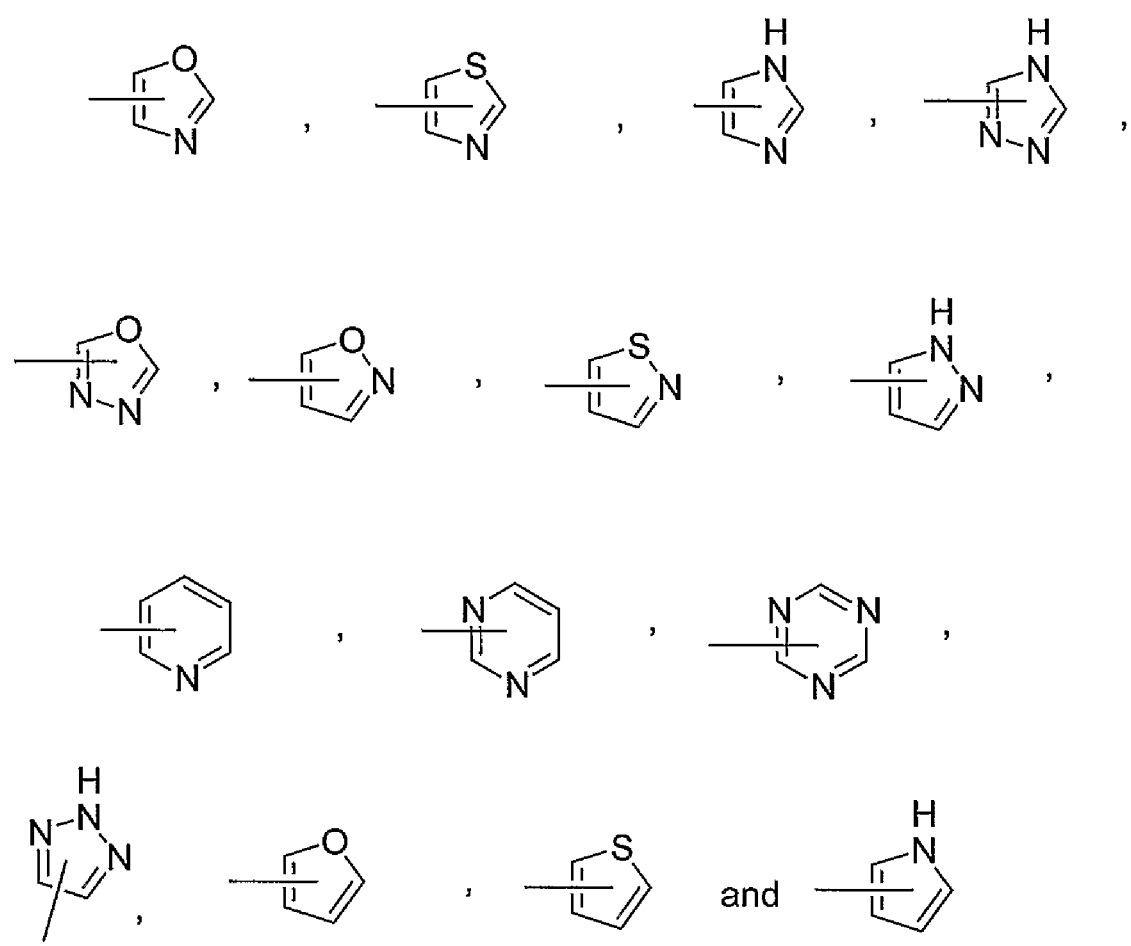
FIG. 1A provides selected monocyclic heteroaryl groups while FIG. 1B provides selected fused bicyclic heteroaryl groups. Each of the groups is optionally substituted with $R^4$ substituents that can be the same or different.

The invention relates to the surprising finding that edema-sparing compounds of Formulae I, II, II, IVa, IVb, V, VI, and VII have properties which makes them therapeutically useful in avoiding or preventing edema. These compounds can be PPARγ partial agonists, and without intending to be bound by theory, it is believed their anti-edema properties may derive from their particular PPARγ modulatory activity. Thus, the invention provides compounds, compositions, and methods for reducing cardiovascular and cerebrovascular risk in patients with edema, or patients without edema but whose underlying disease would be exacerbated by edema.

The above compounds are taught to be useful in treating insulin resistance, Syndrome X, NIDDM, atherosclerosis, and hyperuricemia. These findings further suggest that a particularly useful subpopulation for therapy with these agents according to the invention are subjects with insulin resistance, Syndrome X, NIDDM, atherosclerosis, hyperlipidemia, hypertriglyceridemia, and/or hyperuricemia who also suffer from edema. In other distinct embodiments, the invention provides for the treatment of subpopulations in which the subject has edema but does not have one or more of insulin resistance, Syndrome X, NIDDM, atherosclerosis, hyperlipidemia, hypertriglyceridemia, and/or hyperuricemia.

Malignant and hyperproliferative disease states can be treated by induction of terminal differentiation or of apoptosis of cancer cells that appear to be stuck at an immature stage of development and rapid proliferation. Terminal differentiation can render such cells more quiescent. Such effects are illustrated by the use of all-trans retinoic acid as the standard in treating acute promyelocytic leukemia. In that therapy, the all-trans retinoic acid induces differentiation of the leukemic cells by targeting the retinoic acid receptor $\alpha$. which regulates differentiation and malignant transformation of myelocytic cells (Warrell, R. P. et al., (1993) N. Engl. J. Med. 329:177-189). Receptors of the RXR-related peroxisome proliferator-activated receptor (PPAR) are similarly targets for differentiation therapy. In particular, agonists of PPAR$\gamma$ have been shown to inhibit the proliferation of a variety of hyperplastic and neoplastic tissues in vitro and in vivo. (see, the Background and, particularly, PCT Patent Publication, WO 98/25598).

This invention further relates to the finding that 2-acetamidoethyl 4-chlorophenyl-(3-trifluoromethylphenoxy)-acetate (i.e., halofenate), a prodrug of (−) halofenic acid has advantages over both other halofenic acid derivatives and other selective partial PPAR$\gamma$ partial agonists in the treatment of hyperplasias and neoplasms. Recent clinical trials have provided evidence of an improved side effect profile for the phenoxyacetic acid compounds according to the invention as compared to other PPAR$\gamma$ modulators. In particular, in a Phase II clinical trial, (−) halofenate was largely free of such side effects as hepatoxicity, edema, heart failure, and increased weight gain. And, in addition, the (−) halofenate composition had anti-edema activity of its own.

Thus, in one aspect of the invention provides a method for inhibiting proliferation of a PPAR$\gamma$-responsive hyperproliferative cell, comprising contacting the cell with a compound of Formula I, II, III, IVa, IVb, V, VI, or VII in an amount effective to induce differentiation of the cell. For example, the instant method treats and/or prevents disorders characterized by aberrant cell growth of PPAR$\gamma$-responsive hyperproliferative cells by administering halofenate in a therapeutically effective amount.

ABBREVIATIONS AND DEFINITIONS

The abbreviations used herein are conventional, unless otherwise defined.

The practice of the present invention will employ, unless otherwise indicated, conventional methods of chemistry, biochemistry, molecular biology, cell biology, genetics, immunology and pharmacology, within the skill of the art. Such techniques are explained fully in the literature. See, e.g., Gennaro, A. R., ed. (1990) Remington's Pharmaceutical Sciences, 18th ed., Mack Publishing Co.; Hardman, J. G., Limbird, L. E., and Gilman, A. G., eds. (2001) The Pharmacological Basis of Therapeutics, 10th ed., McGraw-Hill Co.; Colowick, S. et al., eds., Methods In Enzymology, Academic Press, Inc.; Weir, D. M., and Blackwell, C. C., eds. (1986) Handbook of Experimental Immunology, Vols. I-IV, Blackwell Scientific Publications; Maniatis, T. et al., eds. (1989) Molecular Cloning: A Laboratory Manual, 2nd edition, Vols. I-III, Cold Spring Harbor Laboratory Press; Ausubel, F. M. et al., eds. (1999) Short Protocols in Molecular Biology, 4th edition, John Wiley & Sons; Ream et al., eds. (1998) Molecular Biology Techniques: An Intensive Laboratory Course, Academic Press; Newton, C. R., and Graham, A., eds. (1997) PCR (Introduction to Biotechniques Series), 2nd ed., Springer Verlag.

Unless otherwise stated, the following terms used in the specification and claims have the meanings given below.

It is noted here that as used in this specification and the appended claims, the singular forms "a" "an," and "the" include plural reference unless the context clearly dictates otherwise.

The term "edema" refers to an increase in the interstitial fluid volume. Typically, an increase of several liters may occur before the abnormality is evident. Thus, a weight gain of several kilograms may be apparent. The term edema includes anasarca or gross generalized edema, ascites, and hydrothorax. The term includes both pulmonary edema and peripheral edema and is associated with a harmful renal retention of salt and water. The edema may be caused by a primary heart disease (e.g., right- or left-sided heart failure), renal disease, or be a side-effect of a drug therapy. Edema can also be due to obesity, fluid overload states, electrolyte imbalances, liver disease, burns, infections, immune reactions, and sepsis. Symptoms of edema can include weight gain from the retained fluid, congestive heart failure, hypertension, localized ischemia, hypoalbuminemia, hyponatremia, local venous stasis, and local lymphatic stasis. Edema includes lower limb edema and can occur along with venous congestion and/or lymphedema. Swollen lower limbs can be a sign of edema. Edema is often noted clinically by a persistent indentation of the skin "pitting" following pressure.

The term "edema sparing PPAR$\gamma$ modulator" or "edema sparing PPAR$\gamma$ modulator according to the invention" interchangeably refer to the compounds of formula I, II, III, IVa, IVb, V, VI, and VII which are partial agonists of PPAR$\gamma$ and which do not cause clinically significant edema when administered at therapeutically effective doses. The term "phenoxy acetic acid compound" when used with respect to the compounds of Formula I, II, II, IVa, IVb, V, VI, and VII is not meant to be further limiting.

The term "cardiovascular disease" includes heart failure, hypertension, atherosclerosis, arteriosclerosis, stroke, and thrombosis. "Heart failure" includes congestive heart failure, heart failure with diastolic dysfunction, heart failure with systolic dysfunction, heart failure associated with cardiac hypertrophy, and heart failure that develops as a result of chemically induced cardiomyopathy, congenital cardiomyopathy, and cardiomyopathy associated with ischemic heart disease or myocardial infarction. In another aspect the invention provides a method for treating or reducing the risk of a cardiovascular condition in a subject, comprising administering to a subject an effective amount of a compound selected from the group consisting of Formula I, II, III, IVa, IVb, V, VI, and VII. In one embodiment, the cardiovascular condition can be hypertension, stroke, coronary arterial disease, myocardial infarction, peripheral vascular atherosclerosis, or congestive heart failure. In additional embodiments, the subject is obese. In other embodiments, the subject has or has had hypertension. In still other embodiments, the subject has had an infarction of the central nervous system or brain or a myocardial infarction. In still other embodiments, the subject has or has had peripheral edema or pulmonary edema or ascites or hyrothorax. In some embodiments, the subject is obese and hypertensive and over 50 years of age. In other embodiments still, the subject has insulin resistance, metabolic syndrome, Syndrome X, impaired fasting glucose, impaired glucose tolerance, polycystic ovary disease, or "pre-diabetes", or any condition characterized by insulin resistance of any degree.

The term "hypertension" generally includes borderline hypertension (blood pressures between 120/80 and 140/90) and mild hypertension (blood pressures which are greater than a systolic/diastolic reading of 140-159/90-99) as well as the more severe forms of hypertension with higher diastolic values (e.g., greater than 160) or higher systolic values values (e.g., greater than 100 or 120) (as measured in mmHg).

"Hyperproliferative cells" or "hyperplasia" refers to cells undergoing an abnormally high, typically harmful, rate of growth. The term "neoplasia" refers to "new cell growth" that results as a loss of responsiveness to normal growth controls, e.g. to neoplastic cell growth. Neoplasias include but are not limited to cancers and tumors. The neoplasias may be benign, premalignant, or malignant. Neoplasia is a form of hyperplasia or hyperproliferation. The terms are meant to include all types of cancerous growths or oncogenic processes, metastatic tissues or malignantly transformed cells, tissues, or organs, irrespective of histopathologic type or stage of invasiveness.

The term "adipose cell tumor" refers to all cancers or neoplasias arising from cells of adipocytic lineage (i.e., arising from adipose or adipose precursor cells). Adipose cell tumors can be benign or malignant lesions. Examples include lipoma, intramuscular and intermuscular lipoma, neural fibrolipoma, lipoblastoma, lipomatosis, hibernoma, hemangioma, liposarcoma, and lesions that may mimic fat-containing soft-tissue masses.

The term "carcinoma" is recognized by those skilled in the art and refers to malignancies of epithelial or endocrine tissues including respiratory system carcinomas, gastrointestinal system carcinomas, genitourinary system carcinomas (e.g, renal cell carcinoma and bladder tumors), testicular carcinomas, breast carcinomas, prostatic carcinomas, endocrine system carcinomas, and melanomas. Exemplary carcinomas include those forming from tissue of the cervix, lung, prostate, breast, head and neck, colon and ovary. The term also includes carcinosarcomas, (i.e., malignant tumors composed of carcinomatous and sarcomatous tissues). An "adenocarcinoma" refers to a carcinoma derived from glandular tissue or in which the tumor cells form recognizable glandular structures.

The term "sarcoma" refers to malignant tumors of mesenchymal derivation.

The term "leukemic cancer" is known to one of ordinary skill in the art and refers to all cancers or neoplasias of the hemopoietic and immune systems (blood and lymphatic system). The acute and chronic leukemias, together with the other types of tumors of the blood, bone marrow cells (myelomas), and lymph tissue (lymphomas), cause about 10% of all cancer deaths and about 50% of all cancer deaths in children and adults less than 30 years old. Chronic myelogenous leukemia (CML), also known as chronic granulocytic leukemia (CGL), is a neoplastic disorder of the hematopoietic stem cell.

"Leukemia" is known to one of ordinary skill in the art and refers to a progressive, malignant disease of the blood-forming organs, marked by distorted proliferation and development of leukocytes and their precursors in the blood and bone marrow.

The terms "PPARγ-responsive hyperproliferative cell and "PPARγ-responsive neoplastic cell" are used interchangeably herein and refer to a neoplastic or hyperplastic cell which is responsive to PPARγ agonists and partial agonists, including halofenate. Edema-sparing compounds of formula I, II, III, IVa, IVb, V, VI, or VII can inhibit the proliferation and/or induces the expression of differentiation-specific genes and/or induce apoptosis in these cells. These cells include tumor-derived cells that differentiate into adipocytic lineages in response to PPARγ ligands, e.g., human liposarcoma cells. Methods of assessing whether a cell is PPARγ-responsive are well known to one of ordinary skill in the art, and are exemplified in PCT Patent Publication No. WO 98/25598 published Jun. 18, 1998; and also in U.S. Pat. No. 6,242,196 to Spiegelman, which are incorporated by reference herein and particularly with respect to such subject matter.

The identification of subjects who are in need of treatment or prevention of hyperplastic/neoplastic disease states is well within the ability and knowledge of the clinician skilled in the art. Methods of identifying subjects who have, or are at risk of developing hyperplastic or neoplastic disease states suitable for treatment in the instant methods, are well known in the medical arts. Methods for identifying subjects at risk include family history of the development of a particular disease state and the presence of risk factors (e.g., occupational and environmental exposures, genetic histories) associated with the development of that disease state in the subject patient. More generally, a clinician skilled in the art can readily identify subjects in need of the subject invention, by the use of, for example, clinical tests, physical examination and medical/family history.

In one embodiment, the cells to be treated can be hyperproliferative cells of adipocytic lineage (e.g., arising from adipose or adipose precursor cells). Edema-sparing compounds of formula I, II, III, IVa, IVb, V, VI, VII can be administered to prevent the proliferation of an adipose cell tumor. The adipose tumor cell can be of a liposarcoma (e.g., a malignant tumor characterized by large anaplastic lipoblasts, sometimes with foci of normal fat cells). Liposarcomas include, but are not limited to, well differentiated/dedifferentiated, myxoid/round cell and pleiomorphic.

Other adipose cell tumors suitable for treatment with edema-sparing compounds of formula I, II, III, IVa, IVb, V, VI, or VII include, but are not limited to, lipomas (e.g., benign fatty tumors usually composed of mature fat cells). Edema-sparing compounds of formula I, II, III, IVa, IVb, V, VI, or VII can be administered to a subject to treat and/or prevent lipochondromas (comprising mature lipomatous and cartilaginous elements), lipofibromas (containing areas of fibrosis) and lipogranulomas which typically have nodules of lipoid material associated with granulomatous inflammation.

Edema-sparing compounds of formula I, II, III, IVa, IVb, V, VI, or VII can also be administered to inhibit the proliferation of hyperplastic/neoplastic cells of hematopoietic origin (e.g., cells having a myeloid, lymphoid or erythroid lineages or, and precursor cells thereof). For example, edema-sparing compounds of formula I, II, III, IVa, IVb, V, VI, or VII can be administered to a subject to treat myeloid disorders including, but not limited to, acute promyeloid leukemia (APML), acute myelogenous leukemia (AML) and chronic myelogenous leukemia (CML) (Vaickus, L. Crit Rev. in Oncol./Hemotol. 11:267-97 (1991)). Lymphoid malignancies which can be treated by the administration of edema-sparing compounds of formula I, II, III, IVa, IVb, V, VI, or VII include, but are not limited to acute lymphoblastic leukemia (ALL), which includes B-lineage ALL and T-lineage ALL, chronic lymphocytic leukemia (CLL), prolymphocytic leukemia (PLL), hairy cell leukemia (HLL) and Waldenstrom's macroglobulinemia (WM). Additionally, edema-sparing compounds of formula I, II, III, IVa, IVb, V, VI, or VII may be administered to treat malignant lymphomas and leukemias including, but are not limited to, non-Hodgkin's lymphoma and variants thereof, peripheral T-cell lymphomas, adult T-cell leukemia/lymphoma (ATL), cutaneous T-cell lymphoma (CTCL), large granular lymphocytic leukemia (LGF) and Hodgkin's disease.

compounds of formula I, II, III, IVa, IVb, V, VI, or VII can also be administered to a subject to treat organ system malignancies, including, but not limited to, those of the lung, breast, lymphoid, gastrointestinal, and genito-urinary tract as well as adenocarcinomas. Compounds of formula I, II, III, IVa, IVb, V, VI, or VII can be administered, for instance, to a subject with a malignancy or cancer of the brain, colon; kidney (e.g., renal-cell carcinoma), prostate, or testes, lung (e.g., non-small cell carcinoma of the lung), small intestine, stomach, and esophagus.

In some embodiments, compounds of formula I, II, III, IVa, IVb, V, VI, or VII is administered to a subject to treat a solid tumor (e.g., sarcomas and carcinomas having PPARγ-responsive phenotypes). These tumors include, but are not limited to, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma.

In one embodiment, invention is drawn to an individualized therapy. For example, the subject can first be tested to insure that the hyperproliferative or neoplastic cell to be treated is a PPARγ cell type and then administered the compound of formula I, II, III, IVa, IVb, V, VI, or VII when it is demonstrated that the cells are responsive to the compound. In this embodiment, the compound can be administered to the subject and the effect of the compound on the target cell be determined by biopsy to determine the morphology of the target cell. In other embodiments, the target cells may be removed from the subject first and then tested for their responsiveness (e.g., induction of terminal differentiation, apoptosis, contact inhibition of growth, etc.) in vitro. Such means are well known to one of ordinary skill in the art. (See, for instance, PCT Patent Publication, WO 98/25598; U.S. Pat. No. 6,242,196 to Spiegelman. Eucker et al., *Anticancer Drugs* 15(10):955-60 (2004); Mitsiades et al., *Semin Oncol.* 30(2):309-12 (2003); (Guo et al., *World J Gastroenterol.* 0(23):3419-23 (2004); Yoshizumi et al., *Int J Oncol.* 25(3): 631-9 (2004); Fujii et al., *Anticancer Res.* 24(3a):1409-16 (2004); Keshamouni et al., *Oncogene* 23(1):100-8 (2004); and Yoshimura et al., *Int J Mol Med.* 12(6):861-5 (2003)).

A "PPARγ agonist" is an agent which binds to PPARγ to activate or enhance the transcriptional activity of a PPARγ receptor. In certain embodiments, an agonist may induce activation of transcription by PPARγ transcriptional complexes by mimicking a natural ligand for the receptor.

A "PPARγ partial agonist" is an agent which binds to PPARγ to activate or enhance the transcriptional activity of a PPARγ receptor. However, a "partial agonist" also has some antagonist activity and can antagonize the agonist activity of a full PPARγ agonist. Partial agonists are characterized by dose-response curves which, even at the upper end, provide less than the full activation of the PPARγ receptor which can be achieved with a full PPARγ agonist such as rosiglitazone.

A "selective" or "specific" PPARγ ligand, modulator, agonist, or partial agonist is one which interacts preferentially with PPARγ as compared to PPARα, PPARβ, and PPARδ (e.g., can activate, bind to, or inhibit the PPARγ receptor at concentration levels which do not appreciably activate, bind to, or inhibit these of other PPAR receptors).

"Alkyl" refers to a linear saturated monovalent hydrocarbon radical or a branched saturated monovalent hydrocarbon radical having the number of carbon atoms indicated in the prefix. For example, $(C_1-C_6)$alkyl is meant to include methyl, ethyl, n-propyl, 2'-propyl, tert-butyl, pentyl, and the like. For each of the definitions herein (e.g., alkyl, alkenyl, alkoxy, aralkyloxy), when a prefix is not included to indicate the number of main chain carbon atoms in an alkyl portion, the radical or portion thereof will have six or fewer main chain carbon atoms.

"Alkylene" refers to a linear saturated divalent hydrocarbon radical or a branched saturated divalent hydrocarbon radical having the number of carbon atoms indicated in the prefix. For example, $(C_1-C_6)$alkylene is meant to include methylene, ethylene, propylene, 2-methylpropylene, pentylene, and the like.

"Alkenyl" refers to a linear monovalent hydrocarbon radical or a branched monovalent hydrocarbon radical having the number of carbon atoms indicated in the prefix and containing at least one double bond, but no more than three double bonds. For example, $(C_2-C_6)$alkenyl is meant to include, ethenyl, propenyl, 1,3-butadienyl and the like.

"Alkynyl" means a linear monovalent hydrocarbon radical or a branched monovalent hydrocarbon radical containing at least one triple bond and having the number of carbon atoms indicated in the prefix. The term "alkynyl" is also meant to include those alkyl groups having one triple bond and one double bond. For example, $(C_2-C_6)$alkynyl is meant to include ethynyl, propynyl, and the like.

"Alkoxy", "aryloxy" or "aralkyloxy" refers to a radical —OR wherein R is an alkyl, aryl or arylalkyl, respectively, as defined herein, e.g., methoxy, phenoxy, benzyloxy, and the like.

"Aryl" refers to a monovalent monocyclic or bicyclic aromatic hydrocarbon radical of 6 to 10 ring atoms which is substituted independently with one to four substituents, preferably one, two, or three substituents selected from alkyl, cycloalkyl, cycloalkyl-alkyl, halo, nitro, cyano, hydroxy, alkoxy, amino, acylamino, mono-alkylamino, di-alkylamino, haloalkyl, haloalkoxy, heteroalkyl, COR (where R is hydrogen, alkyl, cycloalkyl, cycloalkyl-alkyl, phenyl or phenylalkyl), —$(CR'R'')_n$—COOR (where n is an integer from 0 to 5, R' and R'' are independently hydrogen or alkyl, and R is hydrogen, alkyl, cycloalkyl, cycloalkylalkyl, phenyl or phenylalkyl) or —$(CR'R'')_n$—CONR$^x$R$^y$ (where n is an integer from 0 to 5, R' and R'' are independently hydrogen or alkyl, and R$^x$ and R$^y$ are independently selected from hydrogen, alkyl, cycloalkyl, cycloalkylalkyl, phenyl or phenylalkyl). More specifically the term aryl includes, but is not limited to, phenyl, biphenyl, 1-naphthyl, and 2-naphthyl, and the substituted forms thereof.

"Aralkyl" or "Aryl$(C_1-C_x)$alkyl" refers to the radical —R$^x$R$^y$ where R$^x$ is an alkylene group (having eight or fewer main chain carbon atoms) and R$^y$ is an aryl group as defined above. Thus, "aralkyl" refers to groups such as, for example, benzyl, phenylethyl, 3-(4-nitrophenyl)-2-methylbutyl, and the like. Similarly, "Aralkenyl" means a radical —$R^xR^y$ where $R^x$ is an alkenylene group (an alkylene group having one or two double bonds) and $R^y$ is an aryl group as defined above, e.g., styryl, 3-phenyl-2-propenyl, and the like.

"Cycloalkyl" refers to a monovalent cyclic hydrocarbon radical of three to seven ring carbons. The cycloalkyl group may have one double bond and may also be optionally substituted independently with one, two, or three substituents selected from alkyl, optionally substituted phenyl, or —C(O)$R^z$ (where $R^z$ is hydrogen, alkyl, haloalkyl, amino, mono-alkylamino, di-alkylamino, hydroxy, alkoxy, or optionally substituted phenyl). More specifically, the term cycloalkyl includes, for example, cyclopropyl, cyclohexyl, cyclohexenyl, phenylcyclohexyl, 4-carboxycyclohexyl, 2-carboxamidocyclohexenyl, 2-dimethylaminocarbonyl-cyclohexyl, and the like.

"Cycloalkyl-alkyl" means a radical —$R^xR^y$ wherein $R^x$ is an alkylene group and $R^y$ is a cycloalkyl group as defined herein, e.g., cyclopropylmethyl, cyclohexenylpropyl, 3-cyclohexyl-2-methylpropyl, and the like. The prefix indicating the number of carbon atoms (e.g., $C_4$-$C_{10}$) refers to the total number of carbon atoms from both the cycloalkyl portion and the alkyl portion.

"Haloalkyl" refers to an alkyl group which is substituted with one or more same or different halo atoms, e.g., —$CH_2Cl$, —$CF_3$, —$CH_2CF_3$, —$CH_2CCl_3$, and the like, and further includes those alkyl groups such as perfluoroalkyl in which all hydrogen atoms are replaced by fluorine atoms. The prefix "halo" and the term "halogen" when used to describe a substituent, refer to —F, —Cl, —Br and —I.

"Heteroalkyl" means an alkyl radical as defined herein with one, two or three substituents independently selected from cyano, —$OR^w$, —$NR^xR^y$, and —$S(O)_nR^z$ (where n is an integer from 0 to 2), with the understanding that the point of attachment of the heteroalkyl radical is through a carbon atom of the heteroalkyl radical. $R^w$ is hydrogen, alkyl, cycloalkyl, cycloalkyl-alkyl, aryl, aralkyl, alkoxycarbonyl, aryloxycarbonyl, carboxamido, or mono- or di-alkylcarbamoyl. $R^x$ is hydrogen, alkyl, cycloalkyl, cycloalkyl-alkyl, aryl or aralkyl. $R^y$ is hydrogen, alkyl, cycloalkyl, cycloalkyl-alkyl, aryl, aralkyl, alkoxycarbonyl, aryloxycarbonyl, carboxamido, mono- or di-alkylcarbamoyl or alkylsulfonyl. $R^z$ is hydrogen (provided that n is 0), alkyl, cycloalkyl, cycloalkyl-alkyl, aryl, aralkyl, amino, mono-alkylamino, di-alkylamino, or hydroxyalkyl. Representative examples include, for example, 2-hydroxyethyl, 2,3-dihydroxypropyl, 2-methoxyethyl, benzyloxymethyl, 2-cyanoethyl, and 2-methylsulfonyl-ethyl. For each of the above, $R^w$, $R^x$, $R^y$, and $R^z$ can be further substituted by amino, fluorine, alkylamino, di-alkylamino, OH or alkoxy. Additionally, the prefix indicating the number of carbon atoms (e.g., $C_1$-$C_{10}$) refers to the total number of carbon atoms in the portion of the heteroalkyl group exclusive of the cyano, —$OR^w$, —$NR^xR^y$, or —$S(O)_nR^z$ portions.

"Heteroaryl" means a monovalent monocyclic or bicyclic radical of 5 to 12 ring atoms having at least one aromatic ring containing one, two, or three ring heteroatoms selected from N, O, or S, the remaining ring atoms being C, with the understanding that the attachment point of the heteroaryl radical will be on an aromatic ring. The heteroaryl ring is optionally substituted independently with one to four substituents, preferably one or two substituents, selected from alkyl, cycloalkyl, cycloalkyl-alkyl, halo, nitro, cyano, hydroxy, alkoxy, amino, acylamino, mono-alkylamino, di-alkylamino, haloalkyl, haloalkoxy, heteroalkyl, —COR (where R is hydrogen, alkyl, phenyl or phenylalkyl), —(CR'R")$_n$—COOR (where n is an integer from 0 to 5, R' and R" are independently hydrogen or alkyl, and R is hydrogen, alkyl, cycloalkyl, cycloalkyl-alkyl, phenyl or phenylalkyl), or —(CR'R")$_n$—CONR$^x$R$^y$ (where n is an integer from 0 to 5, R' and R" are independently hydrogen or alkyl, and R$^x$ and R$^y$ are, independently of each other, hydrogen, alkyl, cycloalkyl, cycloalkylalkyl, phenyl or phenylalkyl). More specifically the term heteroaryl includes, but is not limited to, pyridyl, furanyl, thienyl, thiazolyl, isothiazolyl, triazolyl, imidazolyl, isoxazolyl, pyrrolyl, pyrazolyl, pyridazinyl, pyrimidinyl, benzofuranyl, tetrahydrobenzofuranyl, isobenzofuranyl, benzothiazolyl, benzoisothiazolyl, benzotriazolyl, indolyl, isoindolyl, benzoxazolyl, quinolyl, tetrahydroquinolinyl, isoquinolyl, benzimidazolyl, benzisoxazolyl or benzothienyl, and the derivatives thereof.

"Heterocyclyl" or "cycloheteroalkyl" means a saturated or unsaturated non-aromatic cyclic radical of 3 to 8 ring atoms in which one or two ring atoms are heteroatoms selected from O, NR (where R is independently hydrogen or alkyl) or $S(O)_n$ (where n is an integer from 0 to 2), the remaining ring atoms being C, where one or two C atoms may optionally be replaced by a carbonyl group. The heterocyclyl ring may be optionally substituted independently with one, two, or three substituents selected from alkyl, cycloalkyl, cycloalkyl-alkyl, halo, nitro, cyano, hydroxy, alkoxy, amino, mono-alkylamino, di-alkylamino, haloalkyl, haloalkoxy, —COR (where R is hydrogen, alkyl, cycloalkyl, cycloalkyl-alkyl, phenyl or phenylalkyl), —(CR'R")$_n$—COOR (n is an integer from 0 to 5, R' and R" are independently hydrogen or alkyl, and R is hydrogen, alkyl, cycloalkyl, cycloalkyl-alkyl, phenyl or phenylalkyl), or —(CR'R")$_n$—CONR$^x$R$^y$ (where n is an integer from 0 to 5, R' and R" are independently hydrogen or alkyl, R$^x$ and R$^y$ are, independently of each other, hydrogen, alkyl, cycloalkyl, cycloalkylalkyl, phenyl or phenylalkyl). More specifically the term heterocyclyl includes, but is not limited to, tetrahydropyranyl, piperidino, N-methylpiperidin-3-yl, piperazino, N-methylpyrrolidin-3-yl, 3-pyrrolidino, 2-pyrrolidon-1-yl, morpholino, thiomorpholino, thiomorpholino-1-oxide, thiomorpholino-1,1-dioxide, pyrrolidinyl, and the derivatives thereof. The prefix indicating the number of carbon atoms (e.g., $C_3$-$C_{10}$) refers to the total number of carbon atoms in the portion of the cycloheteroalkyl or heterocyclyl group exclusive of the number of heteroatoms.

"Heterocyclylalkyl" or "Cycloheteroalkyl-alkyl" means a radical —$R^xR^y$ where $R^x$ is an alkylene group and $R^y$ is a heterocyclyl group as defined herein, e.g., tetrahydropyran-2-ylmethyl, 4-methylpiperazin-1-ylethyl, 3-piperidinylmethyl, and the like.

"Heterosubstituted cycloalkyl" means a cycloalkyl group wherein one, two, or three hydrogen atoms are replaced by substituents independently selected from the group consisting of cyano, hydroxy, alkoxy, amino, acylamino, mono-alkylamino, di-alkylamino, or —$SO_nR$ (where n is an integer from 0 to 2 and when n is 0, R is hydrogen or alkyl and when n is 1 or 2, R is alkyl, cycloalkyl, cycloalkylalkyl, aryl, aralkyl, heteroaryl, amino, acylamino, mono-alkylamino, di-alkylamino, or hydroxyalkyl). Examples include 4-hydroxycyclohexyl, 2-aminocyclohexyl etc.

"Heteroalkyl substituted cycloalkyl" means a cycloalkyl group wherein one, two, or three hydrogen atoms are replaced independently by heteroalkyl groups, with the understanding that the heteroalkyl group is attached to the cycloalkyl group via a carbon-carbon bond. Examples include 1-hydroxymethyl-cyclopent-1-yl, 2-hydroxymethyl-cyclohex-2-yl and the like.

"Heteroalkyl substituted heterocyclyl" means a heterocyclyl group wherein one, two, or three hydrogen atoms are replaced independently by heteroalkyl groups, with the understanding that the heteroalkyl group is attached to the heterocyclyl group via a carbon-carbon bond. Examples include 4-hydroxymethyl-piperidin-1-yl, and the like.

"Optionally substituted phenyl" means a phenyl ring which is optionally substituted independently with one to four substituents, preferably one or two substituents selected from alkyl, cycloalkyl, cycloalkyl-alkyl, halo, nitro, cyano, hydroxy, alkoxy, amino, acylamino, mono-alkylamino, dialkylamino, haloalkyl, haloalkoxy, heteroalkyl, —COR (where R is hydrogen, alkyl, phenyl or phenylalkyl, —(CR'R")$_n$—COOR (where n is an integer from 0 to 5, R' and R" are independently hydrogen or alkyl, and R is hydrogen, alkyl, cycloalkyl, cycloalkylalkyl, phenyl or phenylalkyl), or —(CR'R")$_n$—CONR$^x$R$^y$ (where n is an integer from 0 to 5, R' and R" are independently hydrogen or alkyl, and R$^x$ and R$^y$ are, independently of each other, hydrogen, alkyl, cycloalkyl, cycloalkylalkyl, phenyl or phenylalkyl).

For each of the definitions above, the term "di-alkylamino" refers to an amino moiety bearing two alkyl groups that can be the same, or different.

As used herein, the term "carboxylic acid surrogate" refers to those moieties that are used as surrogates for a carboxylic acid moiety. Such groups are generally known to one of skill in the art (see, for example, THE PRACTICE OF MEDICINAL CHEMISTRY; Wermuth, C. G., ed., Academic Press, New York, 1996, page 203). Suitable isosteres or surrogates include —C(O)NHSO$_2$R wherein R can be alkyl, haloalkyl, heteroalkyl, aralkyl, aryl, heteroaryl, heterocyclyl, alkoxy, haloalkoxy, aryloxy, alkylamino, haloalkylamino, dialkylamino, dihaloalkylamino, arylamino, diarylamino, arakylamino, diarakylamino or other groups to provide an overall acidic character to the moiety; sulfonic acids; sulfinic acids; phosphonic acids; phosphinic acids; activated sulfonamides (e.g., —SO$_2$NHX wherein X is an electron withdrawing group relative to an alkyl group, such as an acyl group or aryl group; activated carboxamides (e.g., —C(O)NHCN); hydroxamic acids (—C(O)NHOH); acidic heterocycles or substituted heterocycles (e.g., tetrazoles, triazoles, hydroxypyrazoles, hydroxyoxazoles, hydroxythiadiazoles); and acidic alcohols (e.g., —C(CF$_3$)$_2$OH or —CH(CF$_3$)OH).

Compounds that have the same molecular formula but differ in the nature or sequence of bonding of their atoms or the arrangement of their atoms in space are termed "isomers". Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The compounds of this invention may exist in stereoisomeric form if they possess one or more asymmetric centers or a double bond with asymmetric substitution and, therefore, can be produced as individual stereoisomers or as mixtures. Unless otherwise indicated, the description is intended to include any individual stereoisomers as well as mixtures. The methods for the determination of stereochemistry and the separation of stereoisomers are well-known in the art (see discussion in Chapter 4 of ADVANCED ORGANIC CHEMISTRY, 4th edition J. March, John Wiley and Sons, New York, 1992).

"Pharmaceutically acceptable salt" of a compound means a salt that is pharmaceutically acceptable and that possesses the desired pharmacological activity of the parent compound. Such salts include:

(1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynapthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, trimethylamine, N-methylglucamine, and the like.

"Prodrugs" means any compound which releases an active parent drug.

"Protecting group" refers to a grouping of atoms that when attached to a reactive group in a molecule masks, reduces or prevents that reactivity. Examples of protecting groups can be found in T. W. Greene and P. G. Wuts, PROTECTIVE GROUPS IN ORGANIC CHEMISTRY, (Wiley, 2nd ed. 1991) and Harrison and Harrison et al., COMPENDIUM OF SYNTHETIC ORGANIC METHODS, Vols. 1-8 (John Wiley and Sons. 1971-1996). Representative amino protecting groups include formyl, acetyl, trifluoroacetyl, benzyl, benzyloxycarbonyl (CBZ), tert-butoxycarbonyl (Boc), trimethyl silyl (TMS), 2-trimethylsilyl-ethanesulfonyl (SES), trityl and substituted trityl groups, allyloxycarbonyl, 9-fluorenylmethyloxycarbonyl (FMOC), nitro-veratryloxycarbonyl (NVOC) and the like. Representative hydroxy protecting groups include those where the hydroxy group is either acylated or alkylated such as benzyl and trityl ethers as well as alkyl ethers, tetrahydropyranyl ethers, trialkylsilyl ethers and allyl ethers.

Turning next to the compositions of the invention, the term "pharmaceutically acceptable carrier or excipient" means a carrier or excipient that is useful in preparing a pharmaceutical composition that is generally safe, non-toxic and neither biologically nor otherwise undesirable, and includes a carrier or excipient that is acceptable for veterinary use as well as human pharmaceutical use. A "pharmaceutically acceptable carrier or excipient" as used in the specification and claims includes both one and more than one such carrier or excipient.

With reference to the methods of the present invention, the following terms are used with the noted meanings:

The terms "treating" or "treatment" of a disease includes:

(1) preventing the disease, i.e., causing the clinical symptoms of the disease not to develop in a mammal that may be exposed to or predisposed to the disease but does not yet experience or display symptoms of the disease, (2) inhibiting the disease, i.e., arresting or reducing the development of the disease or its clinical symptoms, or (3) relieving the disease, i.e., causing regression of the disease or its clinical symptoms.

The term "therapeutically effective amount" means the amount of the subject compound that will elicit the biological or medical response of a tissue, system, animal or human that is being sought by the researcher, veterinarian, medical doctor or other clinician. "A therapeutically effective amount" includes the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

The term "mammal" includes, without limitation, humans, domestic animals (e.g., dogs or cats), farm animals (cows, horses, or pigs), monkeys, rabbits, mice, and laboratory animals.

The term "insulin resistance" can be defined generally as a disorder of glucose metabolism. More specifically, insulin resistance can be defined as the diminished ability of insulin to exert its biological action across a broad range of concentrations producing less than the expected biologic effect. (see, e.g., Reaven, G. M., *J. Basic & Clin. Phys. & Pharm.* (1998) 9: 387-406 and Flier, J. *Ann Rev. Med.* (1983) 34: 145-60). Insulin resistant persons have a diminished ability to properly metabolize glucose and respond poorly, if at all, to insulin therapy. Manifestations of insulin resistance include insufficient insulin activation of glucose uptake, oxidation and storage in muscle and inadequate insulin repression of lipolysis in adipose tissue and of glucose production and secretion in liver. Insulin resistance can cause or contribute to polycystic ovarian syndrome, Impaired Glucose Tolerance (IGT), gestational diabetes, hypertension, obesity, atherosclerosis and a variety of other disorders. Eventually, the insulin resistant individuals can progress to a point where a diabetic state is reached. The association of insulin resistance with glucose intolerance, an increase in plasma triglyceride and a decrease in high-density lipoprotein cholesterol concentrations, high blood pressure, hyperuricemia, smaller denser low-density lipoprotein particles, and higher circulating levels of plasminogen activator inhibitor-1), has been referred to as "Syndrome X" (see, e.g., Reaven, G. M., *Physiol. Rev.* (1995) 75: 473-486).

The term "diabetes mellitus" or "diabetes" means a disease or condition that is generally characterized by metabolic defects in production and utilization of glucose which result in the failure to maintain appropriate blood sugar levels in the body. The result of these defects is elevated blood glucose, referred to as "hyperglycemia." Two major forms of diabetes are Type 1 diabetes and Type 2 diabetes. As described above, Type 1 diabetes is generally the result of an absolute deficiency of insulin, the hormone which regulates glucose utilization. Type 2 diabetes often occurs in the face of normal, or even elevated levels of insulin and can result from the inability of tissues to respond appropriately to insulin. Most Type 2 diabetic patients are insulin resistant and have a relative deficiency of insulin, in that insulin secretion can not compensate for the resistance of peripheral tissues to respond to insulin. In addition, many Type 2 diabetics are obese. Other types of disorders of glucose homeostasis include Impaired Glucose Tolerance, which is a metabolic stage intermediate between normal glucose homeostasis and diabetes, and Gestational Diabetes Mellitus, which is glucose intolerance in pregnancy in women with no previous history of Type 1 or Type 2 diabetes.

The term "atherosclerosis" encompasses vascular diseases and conditions that are recognized and understood by physicians practicing in the relevant fields of medicine. Atherosclerotic cardiovascular disease, coronary heart disease (also known as coronary artery disease or ischemic heart disease), cerebrovascular disease and peripheral vessel disease are all clinical manifestations of atherosclerosis and are therefore encompassed by the terms "atherosclerosis" and "atherosclerotic disease".

The term "modulate" refers to the treating, prevention, suppression, enhancement or induction of a function or condition.

The terms "obese" and "obesity" refers to, according to the World Health Organization, a Body Mass Index (BMI) greater than 27.8 $kg/m^2$ for men and 27.3 $kg/m^2$ for women (BMI equals weight (kg)/height ($m^2$). Obesity is linked to a variety of medical conditions including diabetes and hyperlipidemia. Obesity is also a known risk factor for the development of Type 2 diabetes (See, e.g., Barrett-Conner, E., *Epidemol. Rev.* (1989) 11: 172-181; and Knowler, et al., *Am. J. Clin. Nutr.* (1991) 53:1543-1551).

Figure 1B:
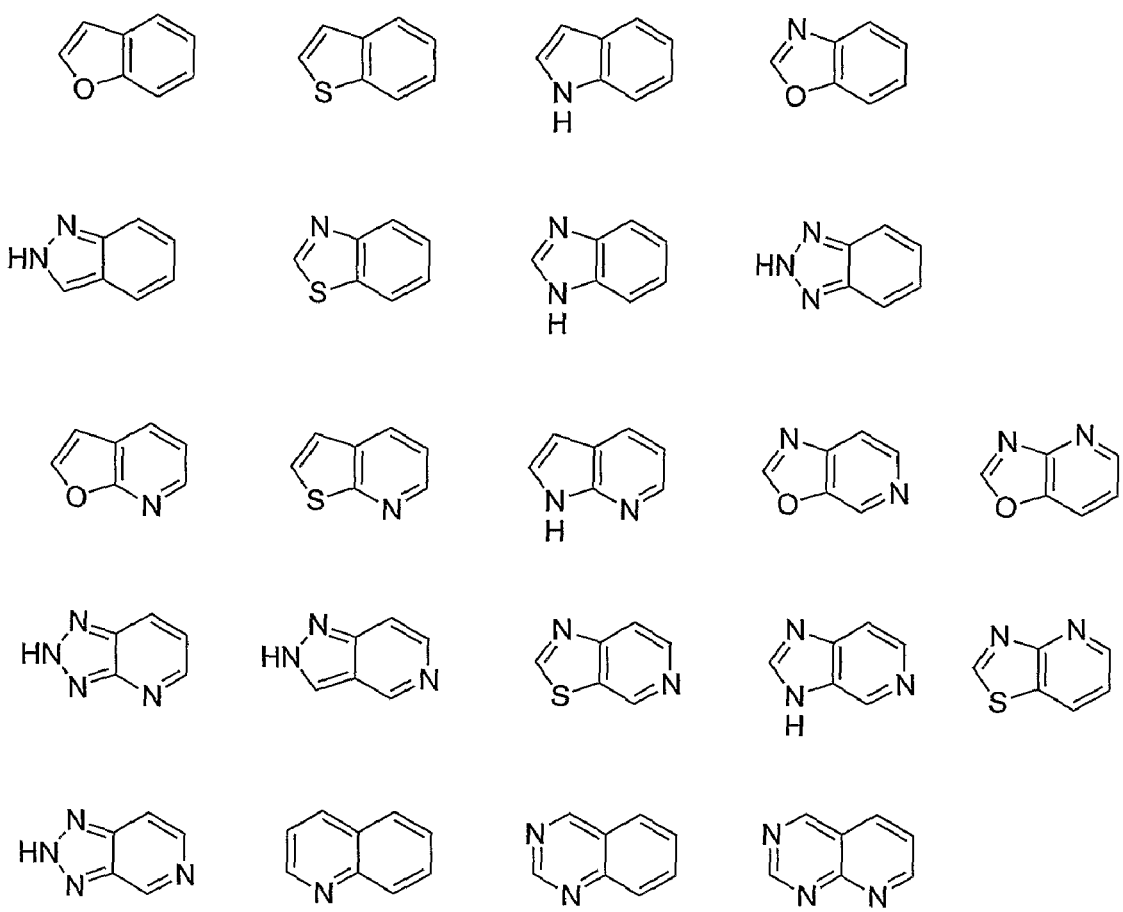
FIG. 1 illustrates a variety of heteroaryl groups (HAr) useful in compounds of formula I.
Figure 2:
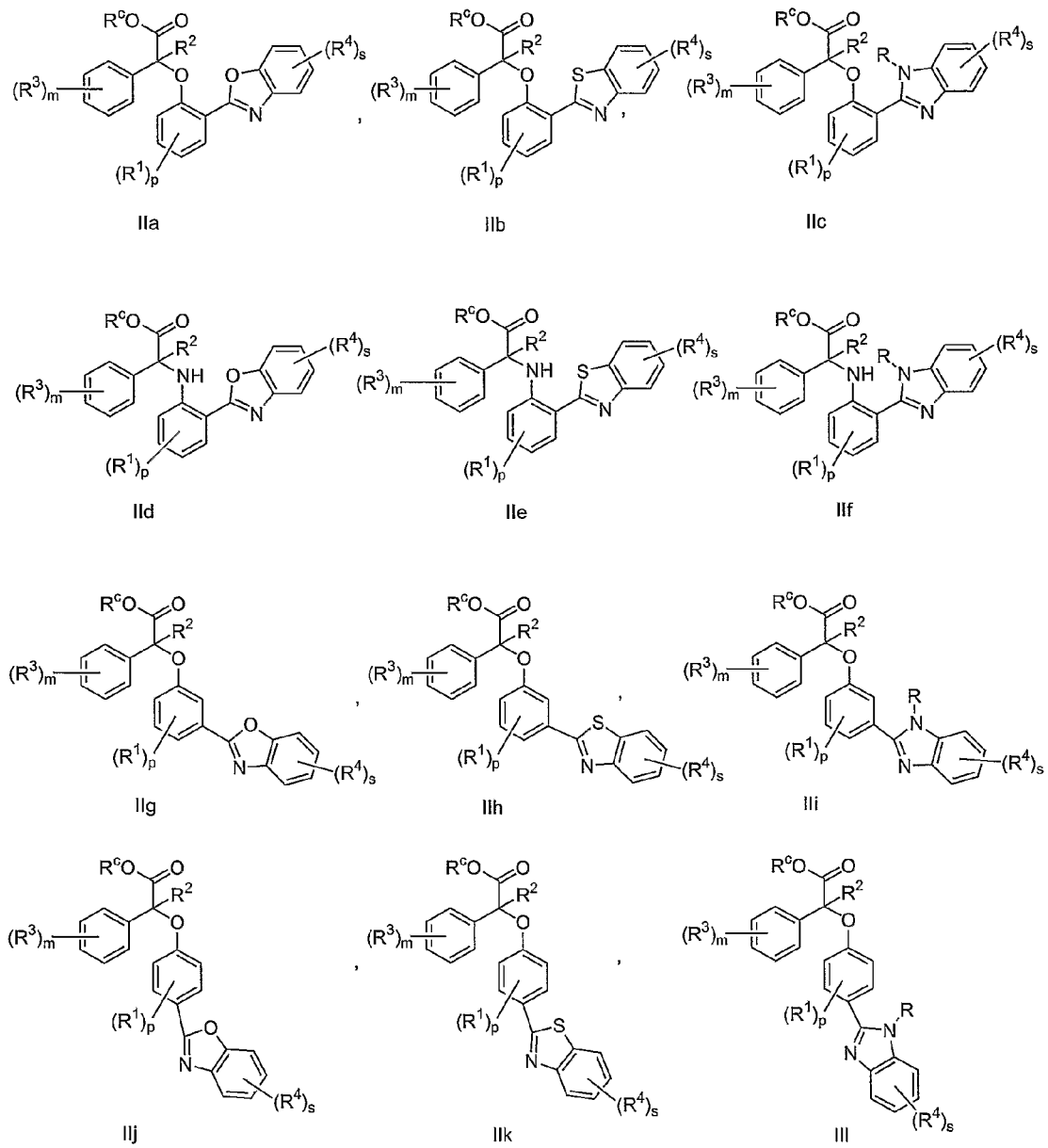
FIG. 2 illustrates a family of preferred sub-generic formulae for compounds of the invention wherein HAr is benzoxazol-2-yl; benzothiazol-2-yl and benzimidazol-2-yl.
Figure 3:
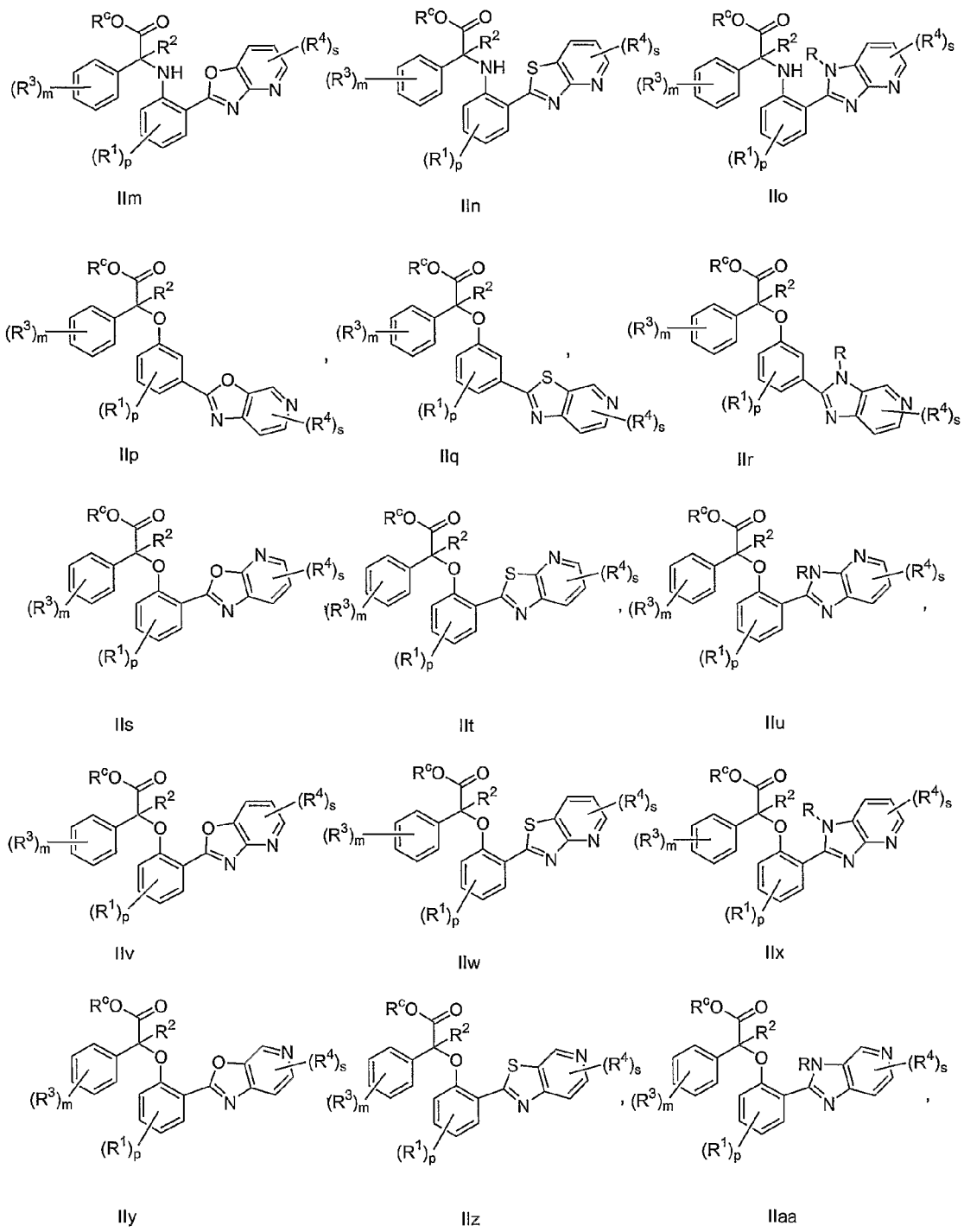
FIG. 3 illustrates another family of preferred sub-generic formulae for compounds of the invention, wherein HAr is a fused bicyclic heteroaryl group.
Figure 4A:
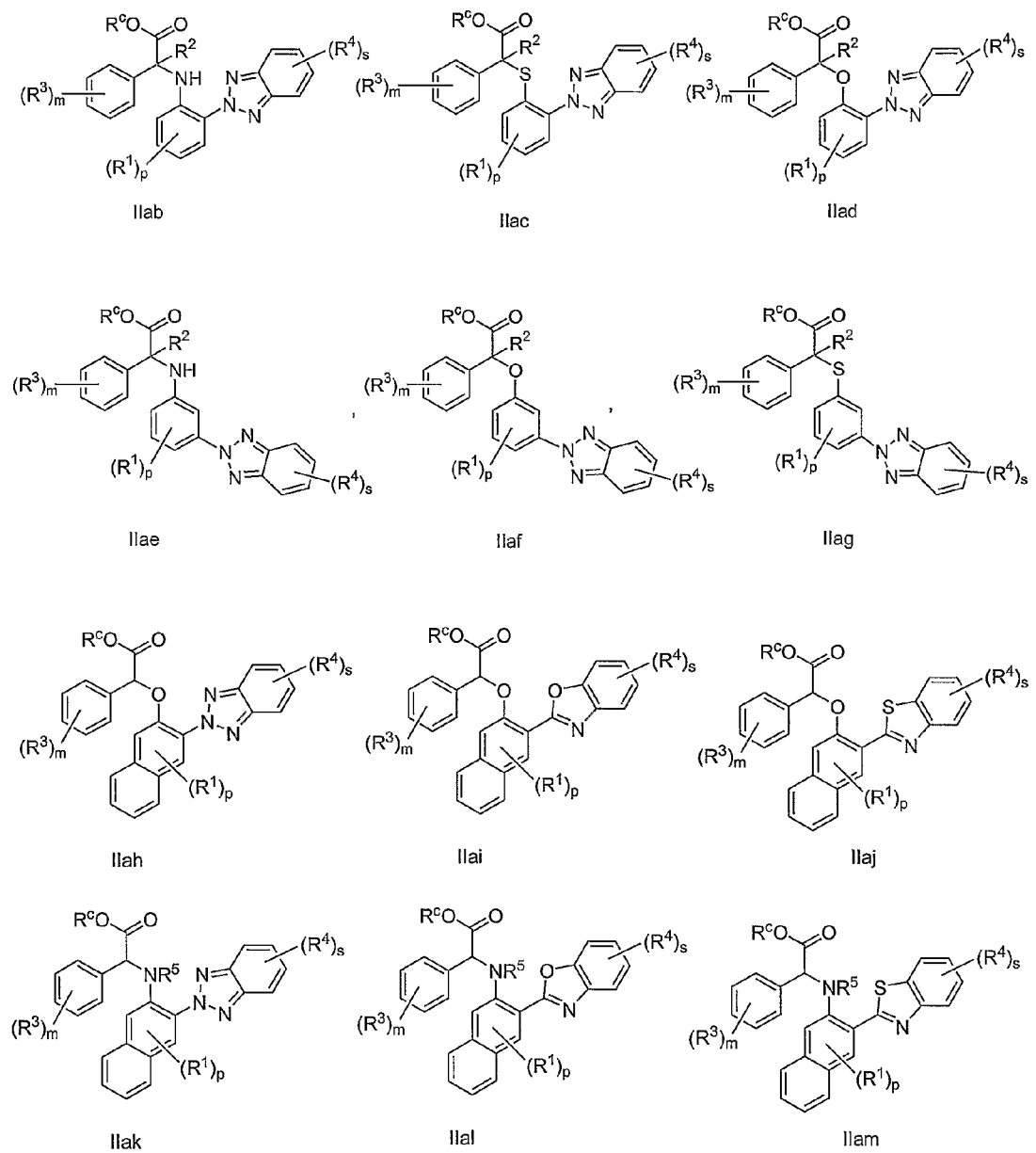
FIG. 4 illustrates yet another family of preferred sub-generic formulae for compounds of the invention wherein HAr is benzoxazol-2-yl, benzothiazol-2-yl and benzotriazol-2-yl (see FIG. 4A).
FIG. 4B illustrates other preferred compounds having carboxylic acid surrogates in place of $CO_2R^c$.
Figure 5A:
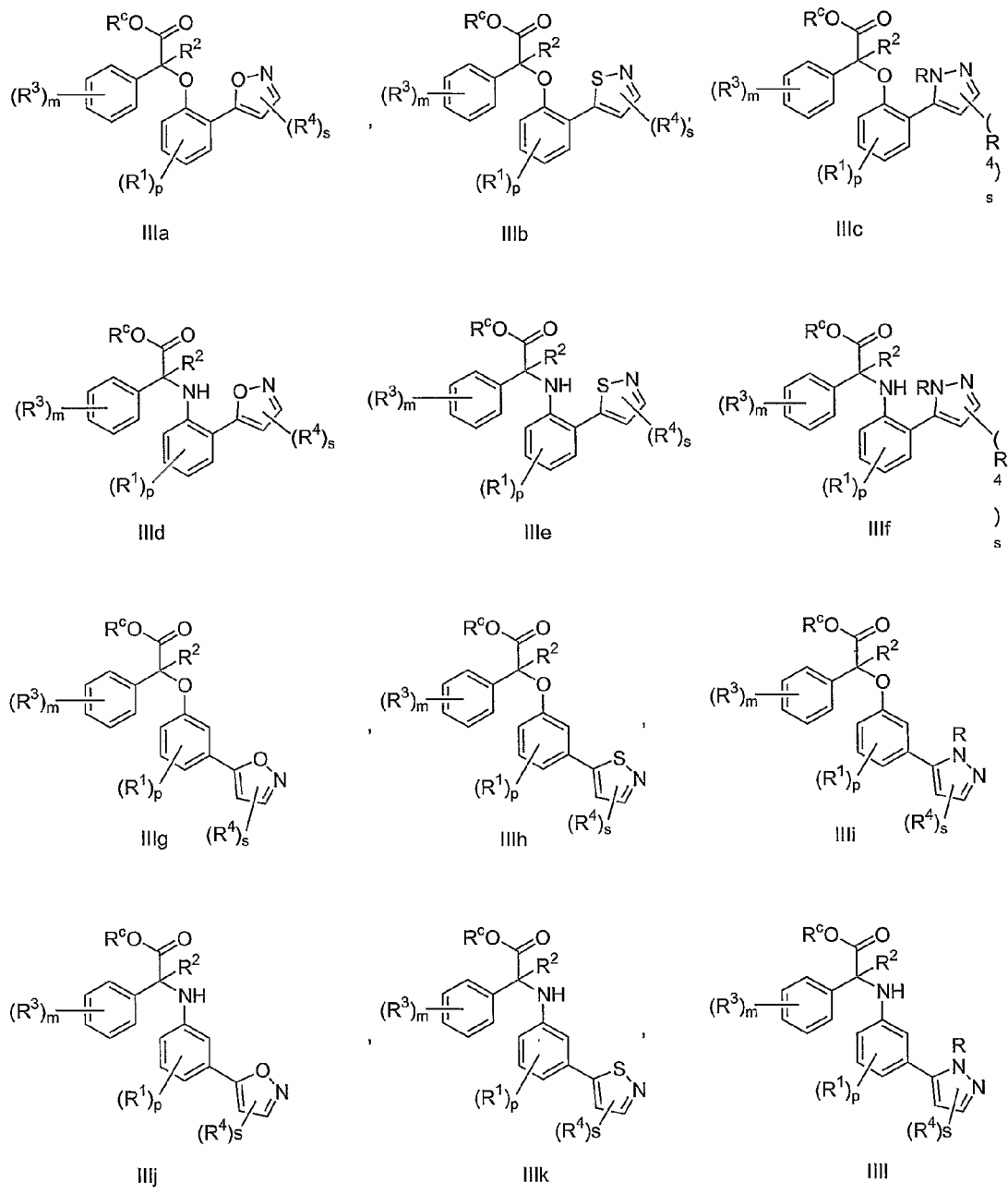
FIG. 5 illustrates yet another family of preferred sub-generic formulae for compounds of the invention wherein HAr is a monocyclic heteroaryl group selected from oxazolyl, isoxazolyl, thiazolyl, isothiazolyl, pyrazolyl and triazolyl (see FIGS. 5A and 5B).
FIG. 5C illustrates other preferred compounds having carboxylic acid surrogates in place of $CO_2R^c$.
Figure 5B:
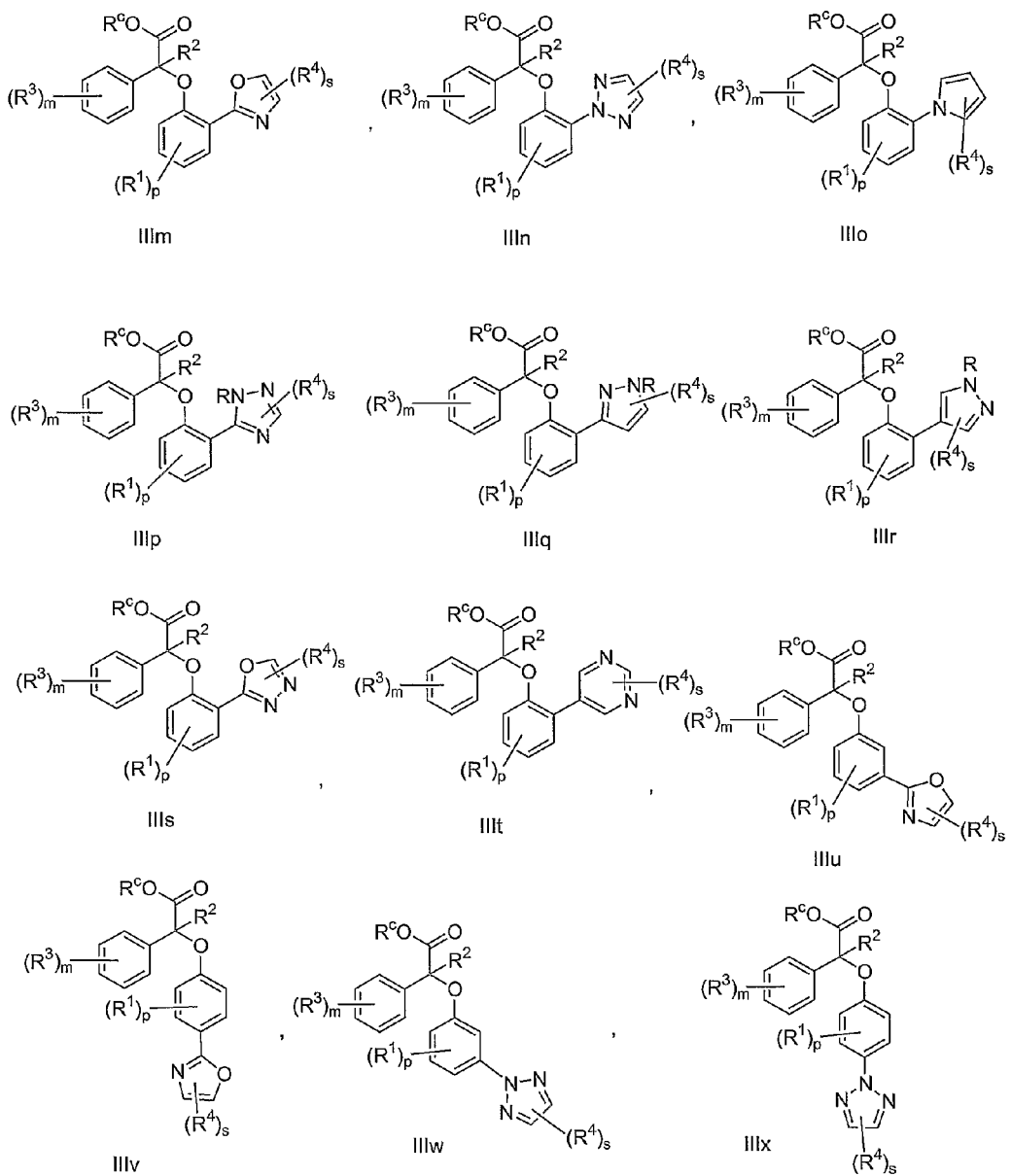
Figure 5C:
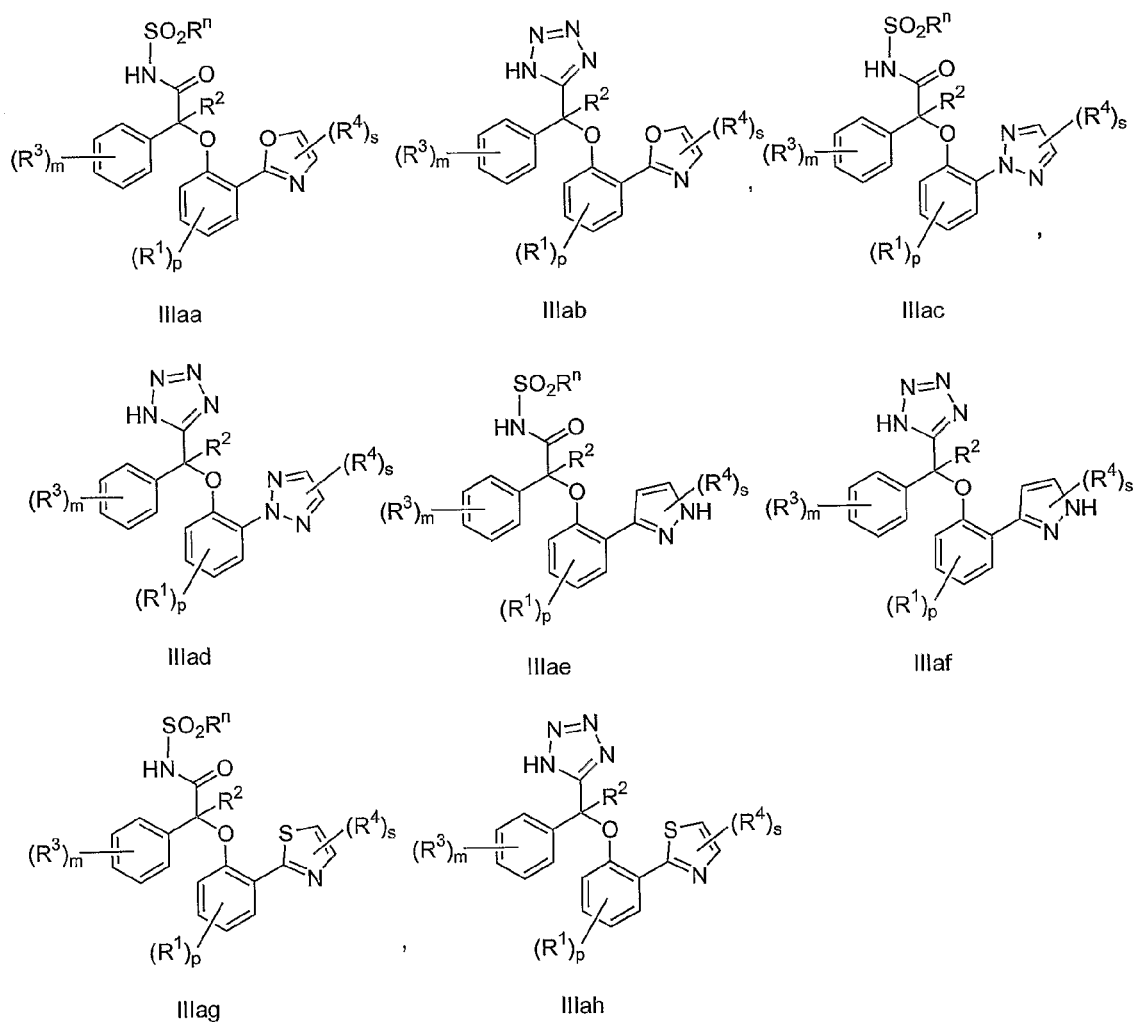

The term "substantially free" with respect to the enantiomeric purity of a compound means that the compound or composition contains a substantially greater proportion of a specified isomer of the compound in relation to its other isomer. In a preferred embodiments, the compound or composition has at least 90% by weight the specified isomer and 10% by weight or less of the other isomer. In a more preferred embodiment, the compound or composition has at least 99% by weight of the specified isomer and 1% by weight or less of the other isomer. In the most preferred embodiments, the compound or composition contains greater than 99%, 99.5% or 99.9% by weight of a specified isomer. These percentages are based upon the total amount of the compound of formula I, II, III, IVa, IVb, V, VI, or VII in the composition. For use according to the invention, either enantiomer may be used. With regard to compounds of FIG. 1, II, or III, compositions which are substantially free of the (+) enantiomer are preferred.

For instance, a composition of the (−) isomer which is "substantially free" of the (+) isomer" indicates the composition has a substantially greater proportion of the (−) isomer of the compound in relation to the (+) isomer. In a preferred embodiments, the compound composition is at least 90% by weight the (−) isomer and 10% by weight or less the (+) isomer. In a more preferred embodiment, the (−) compound is at least 99% by weight the (−) isomer and 1% by weight or less the (+) isomer. In the most preferred embodiment, the (−) isomer is greater than 99%, 99.5% or 99.9% by weight the (−) isomer as compared to the (+) isomer. These percentages are accordingly based upon the total amount of the compound in the composition.

Changes in drug metabolism mediated by inhibition of cytochrome P450 enzymes has a very high potential to precipitate significant adverse effects in patients. Such effects were previously noted in patients treated with racemic halofenate. Recently, racemic halofenic acid was found to inhibit cytochrome P450 2C9, an enzyme known to play a significant role in the metabolism of specific drugs. This inhibition can lead to significant problems with drug interactions with anticoagulants, anti-inflammatory agents and other drugs metabolized by this enzyme. However, quite surprisingly, a substantial difference was observed between the enantiomers of halofenic acid in their inability to inhibit cytochrome P450 2C9, the (−) enantiomer being about twenty-fold less active whereas the (+) enantiomer was quite potent. Thus, use of the (−) enantiomer of halofenic acid and its derivatives can avoid the inhibition of this enzyme and the adverse effects on drug metabolism previously observed with racemic mixtures of halofenic acid or its derivatives. In addition, the (−) isomers of halofenic acid and its derivatives have a superior properties with respect to inhibition of cyclooxygenase 1 (COX-1) which reduce their potential to cause stomach upset as compared to the (+) isomers of halofenic acids and its derivatives. These properties also extend to halofenate and serve to make the (−) isomer of halofenate preferred to the (+) isomer of halofenate in the instant invention.

The term "enantiomeric excess" or "ee" is related to the term "optical purity" in that both are measures of the same phenomenon. The value of ee will be a number from 0 to 100, 0 being racemic and 100 being pure, single enantiomer. A compound that is referred to as 98% optically pure can be described as 96% ee. In some embodiments, the (−) halofenate as an ee of at least 90%, 95%, 98%, 99%, 99.5% or 99.9%. Methods for achieving such levels of optical purity are disclosed in the examples.

"PPARγ" is a member of the peroxisome proliferator-activated receptor family. PPARγ encompasses variants of the receptor such as PPARγ1 and PPARγ2. These two isoforms have different N-terminal amino acid sequence reflecting alternate splicing of a primary RNA transcript (see, Tontonoz, P. et al., *Genes & Dev.* 8:1224-34 (1994); Zhu et al. *J. Biol. Chem.* 268: 26817-20 (1993)).

Compounds for Use According to the Invention

Compounds for use according to the invention include those of formulae I, II, III, IVa, IVb, and V as set forth above.

There are a number of exemplary embodiments.

Embodiment 1

A compound having a formula selected from the group consisting of:

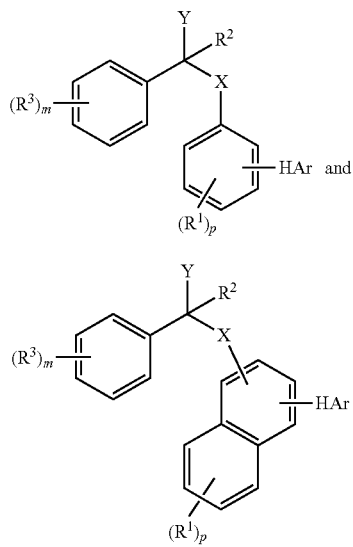

wherein
X is a member selected from the group consisting of O, S, SO, $SO_2$ and NR, wherein R is H, $(C_1-C_8)$alkyl, $COR^a$, $COOR^a$ and $CONR^aR^b$ wherein $R^a$ and $R^b$ are each independently selected from the group consisting of H and $(C_1-C_8)$alkyl;
Y is a member selected from the group consisting of $CH_2OR^c$, $CO_2R^c$, CHO, $CONR^cR^m$, CH(=$NR^c$), CH(=$NOR^c$) and carboxylic acid surrogates, wherein $R^c$ is a member selected from the group consisting of H, $(C_1-C_8)$alkyl, $(C_3-C_8)$alkenyl, $(C_3-C_8)$alkynyl, $(C_3-C_7)$cycloalkyl, $(C_4-C_8)$cycloalkyl-alkyl, aryl, aryl$(C_1-C_8)$alkyl and $(C_1-C_8)$alkylene-Z, wherein Z is selected from the group consisting of $COR^d$, $COOR^d$, $NR^dR^e$, $NR^d$-$CONR^eR^f$, $NR^dCOR^e$, $NR^dCOOR^e$ and $CONR^dR^e$ wherein $R^d$, $R^e$ and $R^f$ are each independently selected from the group consisting of H, $(C_1-C_8)$alkyl and phenyl, or optionally two of $R^d$, $R^e$ and $R^f$ when attached to the same nitrogen atom are combined to form a five- or six-membered ring; and wherein $R^m$ is selected from the group consisting of H, $(C_1-C_8)$alkyl, aryl, OH and $SO_2R^n$, wherein $R^n$ is selected from the group consisting of $(C_1-C_8)$alkyl, $(C_1-C_8)$haloalkyl, aryl$(C_1-C_8)$alkyl, $(C_1-C_8)$heteroalkyl, aryl, heteroaryl, $(C_1-C_8)$alkoxy, aryloxy, alkylamino, dialkylamino, arylamino, diarylamino, haloalkylamino and di(haloalkyl)amino, and $R^m$ and $R^c$ are optionally combined with the nitrogen atom to which each is attached to form a five- or six-membered ring;

HAr is heteroaryl moiety, optionally substituted with from one to three substituents independently selected from the group consisting of halogen, hydroxy, $(C_1-C_8)$alkyl, aryl$(C_1-C_8)$alkyl, $(C_1-C_8)$alkoxy, $(C_2-C_8)$alkenyl, $(C_2-C_8)$alkynyl, $(C_3-C_7)$cycloalkyl, $(C_4-C_8)$cycloalkyl-alkyl, $(C_1-C_8)$heteroalkyl, $(C_2-C_5)$heterocyclyl, aryl, aryloxy, heterosubstituted $(C_3-C_7)$cycloalkyl, heteroalkyl substituted $(C_3-C_7)$cycloalkyl, $(C_1-C_8)$haloalkyl, $O(C_1-C_8)$haloalkyl, nitro, cyano, $CO_2R^g$, $COR^g$, $NR^gR^h$, $S(O)_qR^g$, $SO_2NR^gR^h$, $NR^gCONR^hR^i$, $NR^gCOR^h$, $NR^gCOOR^h$ and $CONR^gR^h$, wherein $R^g$, $R^h$ and $R^i$ are each independently selected from the group consisting of H and $(C_1-C_8)$alkyl, or optionally two of $R^g$, $R^h$ and $R^i$ when attached to the same nitrogen atom are combined to form a five- or six-membered ring, and the subscript q is an integer of from 0 to 2;

each $R^1$ and $R^3$ is a member independently selected from the group consisting of halogen, hydroxy, $(C_1-C_8)$alkyl, $(C_2-C_8)$alkenyl, $(C_2-C_8)$alkynyl, $(C_1-C_8)$alkoxy, $(C_3-C_7)$cycloalkyl, $(C_4-C_8)$cycloalkyl-alkyl, $(C_1-C_8)$haloalkyl, $(C_1-C_8)$heteroalkyl, $(C_2-C_5)$heterocyclyl, heterosubstituted $(C_3-C_7)$cycloalkyl, heteroalkyl substituted $(C_3-C_7)$cycloalkyl, $O(C_1-C_8)$haloalkyl, nitro, cyano, phenyl, O-phenyl, $NR^j$-phenyl, $S(O)_r$-phenyl, $COR^j$, $COOR^j$, $NR^jR^k$, $S(O)_rR_j$, $SO_2NR^jR^k$, $NR^j$-$CONR^kR^l$, $NR^jCOR^k$, $NR^jCOOR^k$ and $CONR^jR^k$ wherein the phenyl ring is optionally substituted and $R^j$, $R^k$ and $R^l$ are each independently selected from the group consisting of H, $(C_1-C_8)$alkyl and $(C_1-C_8)$haloalkyl, or optionally two of $R^j$, $R^k$ and $R^l$ when attached to the same nitrogen atom are combined to form a five- or six-membered ring, and the subscript r is an integer of from 0 to 2;

$R^2$ is a member selected from the group consisting of H, $(C_1-C_8)$alkyl, $(C_1-C_8)$haloalkyl, aryl$(C_1-C_8)$alkyl and $(C_1-C_4)$alkylene-Z, wherein Z is as defined above;

the subscript m is an integer of from 0 to 4;

the subscript p is an integer of from 0 to 3; and pharmaceutically acceptable salts thereof.

Embodiment 2

A compound of embodiment 1, wherein Y is selected from the group consisting of $CH_2OR^c$, $CO_2R^c$, tetrazol-5-yl, $CONHSO_2R^n$ and CHO.

Embodiment 3

A compound of embodiment 1, wherein Y is selected from the group consisting of $CH_2OR^c$, tetrazol-5-yl, $CONHSO_2R^n$ and $CO_2R^c$

Embodiment 4

A compound of embodiment 3, wherein HAr is a fused bicyclic heteroaryl moiety, wherein each of said HAr groups is optionally substituted with from one to three substituents independently selected from the group consisting of halogen, $(C_1-C_4)$alkyl, aryl, aryloxy, $(C_1-C_4)$alkoxy, $(C_1-C_4)$haloalkyl, $O(C_1-C_4)$haloalkyl, nitro, cyano, $CO_2R^g$, $COR^g$ and $CONR^gR^h$.

Embodiment 5

A compound of embodiment 4, wherein X is selected from the group consisting of O, S and NH

Embodiment 6

A compound of embodiment 5, wherein $R^2$ is selected from the group consisting of H, $CH_3$ and $CF_3$.

Embodiment 7

A compound of embodiment 6, wherein HAr is attached to the 2- or 3-position of the ring bearing X and is selected from the group consisting of:

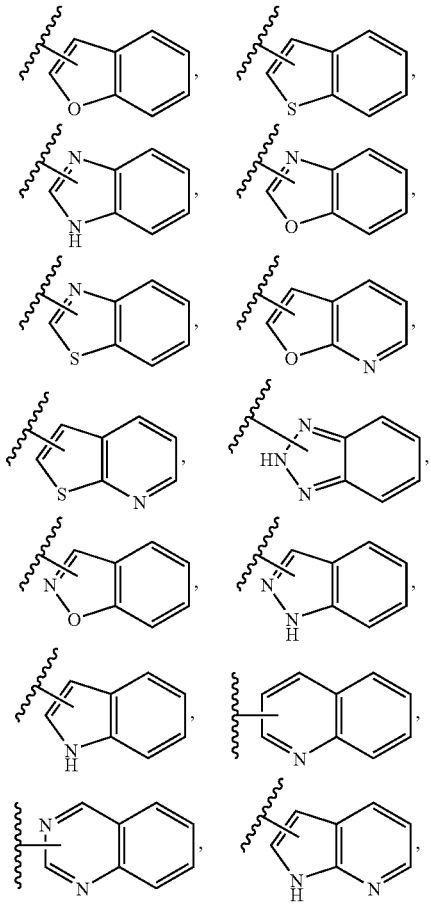

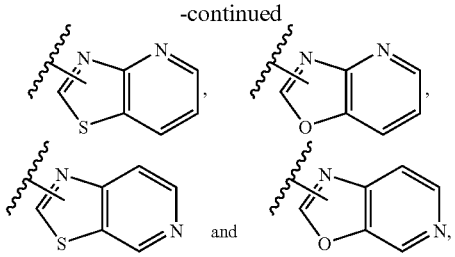

wherein each of said HAr groups is optionally substituted with from one to three substituents independently selected from the group consisting of halogen, $(C_1-C_4)$alkyl, $(C_1-C_4)$alkoxy, $(C_1-C_4)$haloalkyl, $O(C_1-C_4)$haloalkyl, nitro, cyano, $CO_2R^g$, $COR^g$ and $CONR^gR^h$, and wherein the wavy line indicates the point of attached to the ring bearing X through attachment to any available ring member in either ring of HAr.

Embodiment 8

A compound of embodiment 7, wherein the subscript m is 0 to 2 and each $R^3$ when present is independently selected from the group consisting of halogen, $(C_1-C_4)$alkyl, $(C_1-C_4)$alkoxy, $(C_1-C_4)$haloalkyl, $O(C_1-C_4)$haloalkyl, nitro, cyano, phenyl, O-phenyl, $NR^j$-phenyl and $S(O)_r$-phenyl.

Embodiment 9

A compound of embodiment 8, wherein p is an integer of from 0 to 2 and each $R^1$ when present is independently selected from the group consisting of halogen, $(C_1-C_4)$alkyl, $(C_1-C_4)$alkoxy, $(C_1-C_4)$haloalkyl, $O(C_1-C_4)$haloalkyl, nitro, cyano, phenyl, O-phenyl, $NR^j$-phenyl and $S(O)_r$-phenyl.

Embodiment 10

A compound of embodiment 9, wherein m is an integer of from 0 to 2; each $R^3$ when present is independently selected from the group consisting of halogen, $(C_1-C_4)$alkyl, $(C_1-C_4)$alkoxy, $(C_1-C_4)$haloalkyl, $O(C_1-C_4)$haloalkyl, nitro, cyano, phenyl, O-phenyl, $NR^j$-phenyl and $S(O)_r$-phenyl; p is an integer of from 0 to 2; and each $R^1$ is independently selected from the group consisting of halogen, $(C_1-C_4)$alkyl, $(C_1-C_4)$alkoxy, $(C_1-C_4)$haloalkyl, $O(C_1-C_4)$haloalkyl, nitro, cyano, phenyl, O-phenyl, $NR^j$-phenyl and $S(O)_r$-phenyl.

Embodiment 11

A compound of embodiment 7, having a formula selected from the group consisting of:

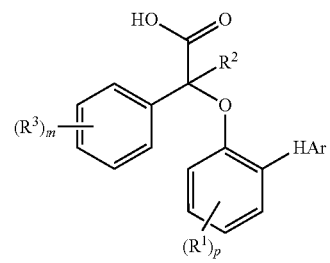

-continued

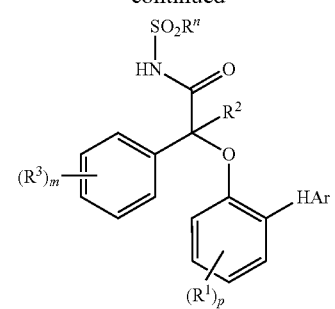

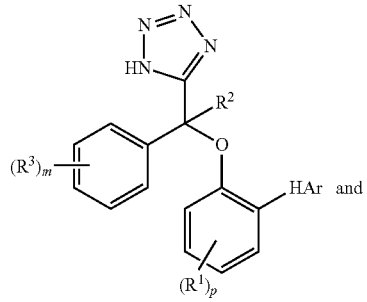

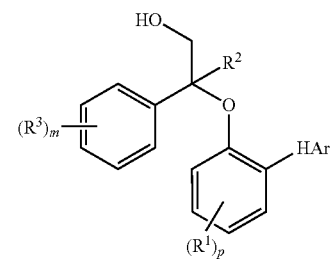

wherein the subscript m is an integer of from 0 to 2, the subscript p is an integer of from 0 to 2, and $R^1$ and $R^3$ are each independently selected from the group consisting of halogen, $(C_1-C_4)$alkyl, $(C_1-C_4)$alkoxy, $(C_1-C_4)$haloalkyl, $O(C_1-C_4)$haloalkyl, nitro, cyano, phenyl, O-phenyl, $NR^j$-phenyl and $S(O)_r$-phenyl; and $R^n$ is selected from the group consisting of $(C_1-C_8)$alkyl, $(C_1-C_8)$haloalkyl, aryl$(C_1-C_8)$alkyl, $(C_1-C_8)$heteroalkyl, aryl, heteroaryl, $(C_1-C_8)$alkoxy, aryloxy, alkylamino, dialkylamino, arylamino, diarylamino, haloalkylamino and di(haloalkyl)amino.

Embodiment 12

A compound of embodiment 11, wherein HAr is selected from the group consisting of

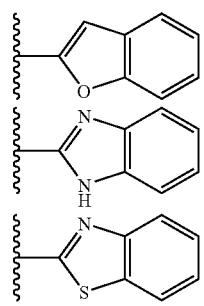

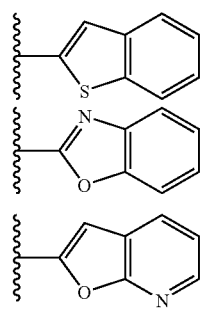

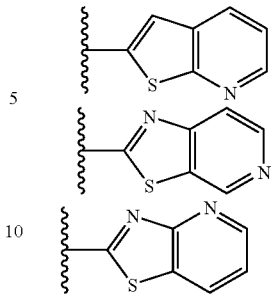

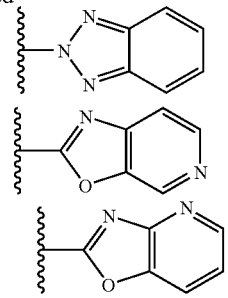

and wherein each of said HAr groups is optionally substituted with from one to three substituents independently selected from the group consisting of halogen, $(C_1-C_4)$alkyl, $(C_1-C_4)$alkoxy, $(C_1-C_4)$haloalkyl, $O(C_1-C_4)$haloalkyl, nitro, cyano, $CO_2R^g$, $COR^g$ and $CONR^gR^h$.

Embodiment 13

A compound of embodiment 12, wherein HAr is selected from the group consisting of

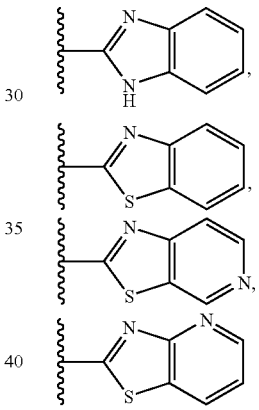

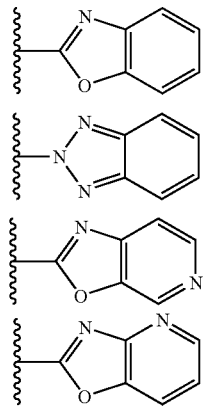

and wherein each of said HAr groups is optionally substituted with from one to three substituents independently selected from the group consisting of halogen, $(C_1-C_4)$alkyl, $(C_1-C_4)$alkoxy, $(C_1-C_4)$haloalkyl, $O(C_1-C_4)$haloalkyl, nitro, cyano, $CO_2R^c$, $COR^c$ and $CONR^cR^d$.

Embodiment 14

A compound of embodiment 13, wherein HAr is 2-benzoxazolyl; $R^2$ is H or $CH_3$; the subscript m is 0 or 1, and p is 1 or 2; and $R^1$ and $R^3$ are each independently selected from the group consisting of halogen, $(C_1-C_4)$alkyl, $(C_1-C_4)$alkoxy, $(C_1-C_4)$haloalkyl, $O(C_1-C_4)$haloalkyl, nitro, cyano, $CO_2R^g$, $COR^g$ and $CONR^gR^h$.

Embodiment 15

A compound of embodiment 13, wherein HAr is 2-benzothiazolyl; $R^2$ is H or $CH_3$; the subscript m is 0 or 1, and p is 1 or 2; and $R^1$ and $R^3$ are each independently selected from the group consisting of halogen, $(C_1-C_4)$alkyl, $(C_1-C_4)$alkoxy, $(C_1-C_4)$haloalkyl, $O(C_1-C_4)$haloalkyl, nitro, cyano, $CO_2R^g$, $COR^g$ and $CONR^gR^h$.

Embodiment 16

A compound of embodiment 13, wherein HAr is 2-benzotriazolyl; $R^2$ is H or $CH_3$; the subscript m is 0 or 1, and p is 1 or 2; and $R^1$ and $R^3$ are each independently selected from the group consisting of halogen, $(C_1-C_4)$alkyl, $(C_1-C_4)$alkoxy, $(C_1-C_4)$haloalkyl, $O(C_1-C_4)$haloalkyl, nitro, cyano, $CO_2R^g$, $COR^g$ and $CONR^gR^h$.

Embodiment 17

A compound of embodiment 3, wherein HAr is a monocyclic heteroaryl moiety, wherein each of said HAr groups is optionally substituted with from one to three substituents independently selected from the group consisting of halogen, $(C_1-C_4)$alkyl, $(C_1-C_8)$heteroalkyl, $(C_1-C_4)$alkoxy, $(C_1-C_4)$haloalkyl, $O(C_1-C_4)$haloalkyl, aryl$(C_1-C_4)$alkyl, aryl, heteroaryl, nitro, cyano, $CO_2R^g$, $COR^g$ and $CONR^gR^h$.

Embodiment 18

A compound of embodiment 17, wherein X is selected from the group consisting of O, S and NH.

Embodiment 19

A compound of embodiment 18, wherein $R^2$ is selected from the group consisting of H, $CH_3$ and $CF_3$.

Embodiment 20

A compound of embodiment 19, wherein HAr is attached to the 2- or 3-position of the phenyl ring bearing X and is selected from the group consisting of

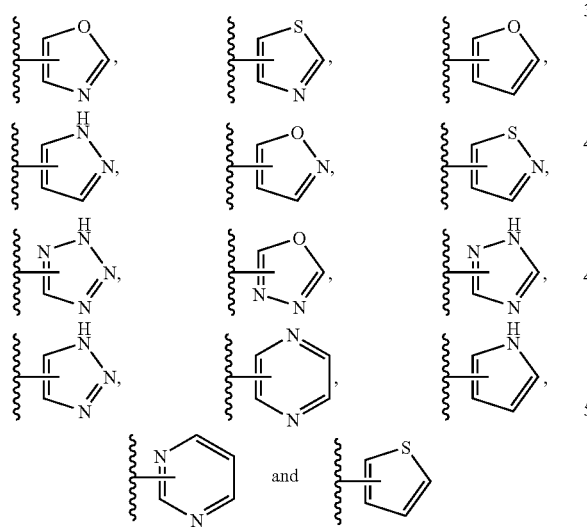

wherein each of said HAr groups is optionally substituted with from one to three substituents independently selected from the group consisting of halogen, $(C_1-C_4)$alkyl, $(C_1-C_8)$heteroalkyl, $(C_1-C_4)$alkoxy, $(C_1-C_4)$haloalkyl, $O(C_1-C_4)$haloalkyl, aryl$(C_1-C_4)$alkyl, aryl, heteroaryl, nitro, cyano, $CO_2R^g$, $COR^g$ and $CONR^gR^h$, and the wavy line indicates the attachment to the ring bearing X.

Embodiment 21

A compound of claim 20, wherein m is 0 to 2 and each $R^3$ when present is independently selected from the group consisting of halogen, $(C_1-C_4)$alkyl, $(C_1-C_4)$alkoxy, $(C_1-C_4)$haloalkyl, $O(C_1-C_4)$haloalkyl, nitro, cyano, phenyl, O-phenyl, $NR^j$-phenyl and $S(O)_r$-phenyl.

Embodiment 22

A compound of embodiment 21, wherein p is 0 to 2 and each $R^1$ when present is independently selected from the group consisting of halogen, $(C_1-C_4)$alkyl, $(C_1-C_4)$alkoxy, $(C_1-C_4)$haloalkyl, $O(C_1-C_4)$haloalkyl, nitro, cyano, phenyl, O-phenyl, $NR^j$-phenyl and $S(O)_r$-phenyl.

Embodiment 23

A compound of embodiment 22, wherein m is an integer of from 0 to 2; each $R^3$ is independently selected from the group consisting of halogen, $(C_1-C_4)$alkyl, $(C_1-C_4)$alkoxy, $(C_1-C_4)$haloalkyl, $O(C_1-C_4)$haloalkyl, nitro and cyano; p is an integer of from 0 to 2; and each $R^1$ is independently selected from the group consisting of halogen, $(C_1-C_4)$alkyl, $(C_1-C_4)$alkoxy, $(C_1-C_4)$haloalkyl, $O(C_1-C_4)$haloalkyl, nitro and cyano.

Embodiment 24

A compound of embodiment 20, having a formula selected from the group consisting of:

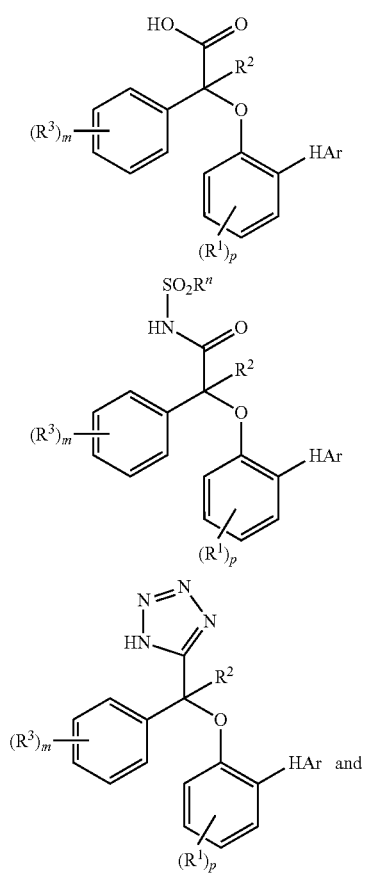

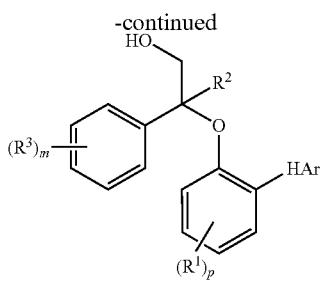

wherein m is an integer of from 0 to 2, p is an integer of from 0 to 2, and $R^1$ and $R^3$ are each independently selected from the group consisting of halogen, $(C_1-C_4)$alkyl, $(C_1-C_4)$alkoxy, $(C_1-C_4)$haloalkyl, $O(C_1-C_4)$haloalkyl, nitro, cyano, phenyl, O-phenyl, $NR^j$-phenyl and $S(O)_r$-, phenyl; and $R^n$ is selected from the group consisting of $(C_1-C_8)$alkyl, $(C_1-C_8)$haloalkyl, aryl$(C_1-C_8)$alkyl, $(C_1-C_8)$heteroalkyl, aryl, heteroaryl, $(C_1-C_8)$alkoxy, aryloxy, alkylamino, dialkylamino, arylamino, diarylamino, haloalkylamino and di(haloalkyl)amino.

Embodiment 25

A compound of embodiment 24, wherein HAr is selected from the group consisting of

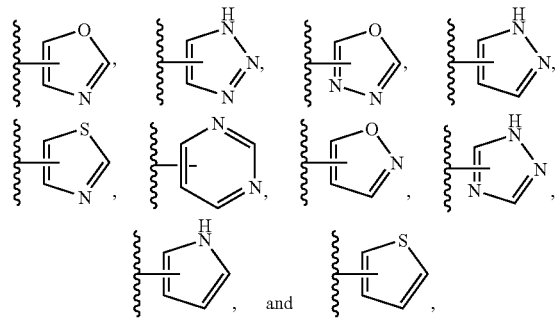

wherein each of said HAr groups is optionally substituted with from one to three substituents independently selected from the group consisting of halogen, $(C_1-C_4)$alkyl, $(C_1-C_8)$heteroalkyl, $(C_1-C_4)$alkoxy, $(C_1-C_4)$haloalkyl, $O(C_1-C_4)$haloalkyl, aryl$(C_1-C_4)$alkyl, aryl, heteroaryl, nitro, cyano, $CO_2R^g$, $COR^g$ and $CONR^gR^h$.

Embodiment 26

A compound of embodiment 24, wherein HAr is selected from the group consisting of

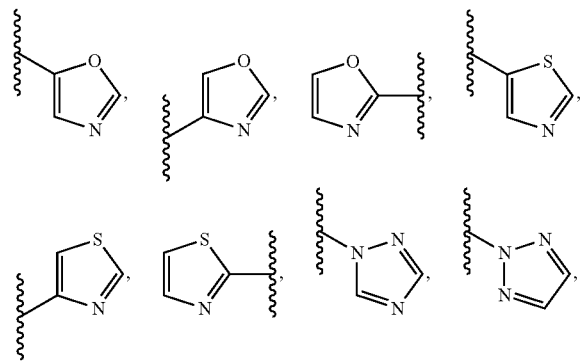

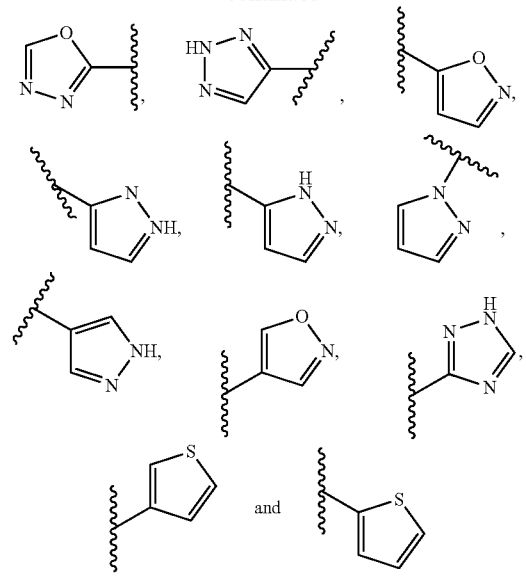

wherein each of said HAr groups is optionally substituted with from one to two substituents independently selected from the group consisting of halogen, $(C_1-C_4)$alkyl, $(C_1-C_8)$heteroalkyl, $(C_1-C_4)$alkoxy, $(C_1-C_4)$haloalkyl, $O(C_1-C_4)$haloalkyl, aryl$(C_1-C_4)$alkyl, aryl, heteroaryl, nitro, cyano, $CO_2R^g$, $COR^g$ and $CONR^gR^h$.

Embodiment 27

A compound of embodiment 26, wherein m is an integer of from 0 to 2, p is an integer of from 0 to 2, $R^1$ and $R^3$ are each independently selected from the group consisting of F, Cl, Br, $(C_1-C_4)$alkyl, $(C_1-C_4)$alkoxy, $(C_1-C_4)$haloalkyl, $O(C_1-C_4)$haloalkyl, CN, $NO_2$ and phenyl.

Embodiment 28

A compound of embodiment 27, wherein HAr is optionally substituted 2-, 4- or 5-thiazolyl wherein the thiazolyl is optionally substituted with from one to two substituents selected from the group consisting of F, Cl, Br, $(C_1-C_4)$alkyl, aryl$(C_1-C_4)$alkyl, $(C_1-C_4)$alkoxy, $(C_1-C_4)$haloalkyl, $O(C_1-C_4)$haloalkyl, CN and phenyl; $R^2$ is H or $CH_3$; the subscript m is 0 or 1 and p is 1 or 2; and $R^1$ and $R^3$ are each independently selected from the group consisting of F, Cl, Br, $(C_1-C_4)$alkyl, $(C_1-C_4)$alkoxy, $(C_1-C_4)$haloalkyl, $O(C_1-C_4)$haloalkyl, CN, $NO_2$ and phenyl.

Embodiment 29

A compound of embodiment 27, wherein HAr is selected from the group consisting of optionally substituted 1, 3, 4 or 5-pyrazolyl wherein the pyrazolyl is optionally substituted with from one to two substituents selected from the group consisting of F, Cl, Br, $(C_1-C_4)$alkyl, aryl$(C_1-C_4)$alkyl, $(C_1-C_4)$alkoxy, $(C_1-C_4)$haloalkyl, $O(C_1-C_4)$haloalkyl, CN and phenyl; $R^2$ is H or $CH_3$; the subscript m is 0 or 1 and p is 1 or 2; and $R^1$ and $R^3$ are each independently selected from the group consisting of F, Cl, Br, $(C_1-C_4)$alkyl, $(C_1-C_4)$alkoxy, $(C_1-C_4)$haloalkyl, $O(C_1-C_4)$haloalkyl, CN, $NO_2$ and phenyl.

Embodiment 30

A compound of embodiment 27, wherein HAr is optionally substituted 2-, 4- or 5-oxazolyl wherein the oxazolyl is optionally substituted with from one to two substituents selected from the group consisting of F, Cl, Br, $(C_1-C_4)$alkyl, aryl$(C_1-C_4)$alkyl, $(C_1-C_4)$alkoxy, $(C_1-C_4)$haloalkyl, O$(C_1-C_4)$haloalkyl, CN and phenyl; $R^2$ is H or $CH_3$; the subscript m is 0 or 1 and p is 1 or 2; and $R^1$ and $R^3$ are each independently selected from the group consisting of F, Cl, Br, $(C_1-C_4)$alkyl, $(C_1-C_4)$alkoxy, $(C_1-C_4)$haloalkyl, O$(C_1-C_4)$haloalkyl, CN, $NO_2$ and phenyl.

Embodiment 31

A compound of embodiment 27, wherein HAr is optionally substituted 1,2,3-triazol-2-yl wherein the 1,2,3-triazol-2-yl is optionally substituted with from one to two substituents selected from the group consisting of F, Cl, Br, $(C_1-C_4)$alkyl, aryl$(C_1-C_4)$alkyl, $(C_1-C_4)$alkoxy, $(C_1-C_4)$haloalkyl, O$(C_1-C_4)$haloalkyl, CN and phenyl; $R^2$ is H or $CH_3$; the subscript m is 0 or 1 and p is 1 or 2; and $R^1$ and $R^3$ are each independently selected from the group consisting of F, Cl, Br, $(C_1-C_4)$alkyl, $(C_1-C_4)$alkoxy, $(C_1-C_4)$haloalkyl, O$(C_1-C_4)$haloalkyl, CN, $NO_2$ and phenyl.

Methods of making the above compounds is taught in U.S. Patent Application Publication No. 20040029933, assigned to the same assignee as the present application and which is incorporated by reference it its entirety. This reference also presents in vivo biological data on the activity of representative compounds of Formula V. See also PCT Application Publication No. WO03/080545, which is incorporated herein by reference.

In some embodiments the compound is of one of the following formula:

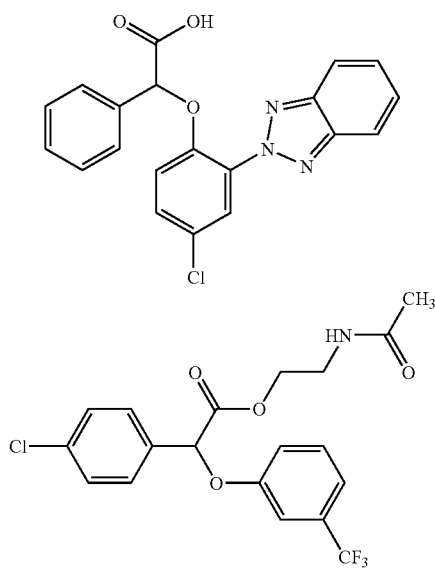

or a pharmaceutically acceptable salt or solvate thereof. Preferably, the compound according to the above formula is the (−) isomer. Methods for making such compounds are taught in U.S. Patent Application Publication No. 20030220399 which is incorporated herein by reference. Methods of resolving alpha-(phenoxy)phenylacetic acid derivatives are taught in U.S. Patent Application Publication No. 20050033084 which is incorporated herein by reference in its entirety.

In another embodiment, the compound is a prodrug which is hydrolysable in vivo to yield a therapeutically effective amount of a (−) halofenic acid or a compound of the formula:

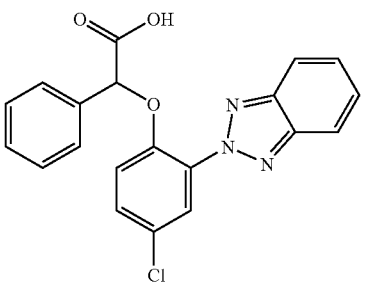

In some embodiments, more than 80%, 90%, 95%, or 99% of the prodrug is converted to the (−) halofenic acid or the above compound by hydrolysis in vivo.

In other embodiments, the compound is a compound of the formula

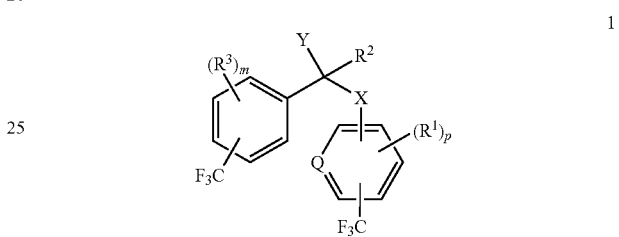

1 including all pharmaceutically acceptable salts and prodrugs thereof, in which X is a member selected from the group consisting of O, S, SO, $SO_2$, CHR and NR, and R is H, $(C_1-C_8)$alkyl, $COR^a$, $COOR^a$ and $CONR^aR^b$ and in which $R^a$ and $R^b$ are each independently selected from the group consisting of H and $(C_1-C_8)$alkyl; and Y is a member selected from the group consisting of $CH_2OR^c$, $CO_2R^c$, tetrazole, CHO, $CONR^cR^m$, CH(=$NR^c$) and CH(=$NOR^c$), in which $R^c$ is a member selected from the group consisting of H, $(C_1-C_8)$alkyl, $(C_3-C_8)$alkenyl, $(C_3-C_8)$alkynyl, $(C_3-C_7)$cycloalkyl, $(C_4-C_8)$cycloalkyl-alkyl, aryl, aryl$(C_1-C_8)$alkyl and $(C_1-C_8)$alkylene-Z, in which Z is selected from the group consisting of $COR^d$, $COOR^d$, $NR^dR^e$, $NR^dCONR^e$, $NR^d$-$COR^e$, $NR^dCOOR^e$ and $CONR^dR^e$ in which $R^d$, $R^e$ and $R^f$ are each independently selected from the group consisting of H, $(C_1-C_8)$alkyl and phenyl, or optionally two of $R^d$, $R^e$ and $R^f$ when attached to the same nitrogen atom are combined to form a five- or six-membered ring; and in which $R^m$ is selected from the group consisting of H, $(C_1-C_8)$alkyl, aryl and OH, and $R^m$ and $R^c$ are optionally combined with the nitrogen atom to which each is attached to form a five or six-membered ring; each $R^1$ and $R^3$ is a member independently selected from the group consisting of halogen, hydroxy, $(C_1-C_8)$alkyl, $(C_2-C_8)$alkenyl, $(C_2-C_8)$alkynyl, $(C_1-C_8)$alkoxy, $(C_3-C_7)$cycloalkyl, $(C_4-C_8)$cycloalkyl-alkyl, $(C_1-C_8)$haloalkyl, $(C_1-C_8)$heteroalkyl, $(C_2-C_5)$heterocyclyl, heterosubstituted $(C_3-C_7)$cycloalkyl, heteroalkyl substituted $(C_3-C_7)$cycloalkyl, O$(C_1-C_8)$haloalkyl, nitro, cyano, phenyl, O-phenyl, $NR^j$-phenyl, S(O)$_r$-phenyl, $COR^j$, $COOR^j$, $NR^jR^k$, S(O)$_rR^j$, $SO_2NR^jR^k$, $NR^jCONR^kR^l$, $NR^jCOR^k$, $NR^jCOOR^k$ and $CONR^jR^k$ in which the phenyl ring is optionally substituted and $R^j$, $R^k$ and $R^l$ are each independently selected from the group consisting of H and $(C_1-C_8)$alkyl, or optionally two of $R^j$, $R^k$ and $R^l$ when attached to the same nitrogen atom are combined to form a five- or six-membered ring, and the subscript r is an integer of from 0 to 2; and $R^2$ is a member selected from the group consisting of H and $(C_1$-$C_8)$alkyl; Q is CH or N; and the subscript m is an integer of from 0 to 3; and the subscript p is an integer of from 0 to 2.

In particular embodiments of the above, Q is CH. In others, X is selected from the group consisting of O, S and NR. In still others, Y is $CO_2R^c$. In some embodiments of the above, m is 0 to 2 and the subscript p is 0 to 1 and, optionally, further, each $R^3$ is selected from the group consisting of halogen, nitro, $(C_1$-$C_8)$ alkyl, $(C_1$-$C_8)$haloalkyl, $(C_1$-$C_8)$ alkoxy and $(C_1$-$C_8)$ haloalkoxy. In other embodiments of any of the above, $R^1$ is selected from the group consisting of halogen, nitro, $(C_1$-$C_8)$ alkyl, $(C_1$-$C_8)$haloalkyl, $(C_1$-$C_8)$ alkoxy and $(C_1$-$C_8)$haloalkoxy. In yet other embodiments of any of the above, $R^c$ is selected from the group consisting of H, $(C_1$-$C_8)$alkyl and $(C_1$-$C_8)$alkylene-Z, and optionally further, $R^2$ is H or $CH_3$.

In yet another embodiment of the above formula, Q is CH; X is selected from the group consisting of O and NR; Y is selected from the group consisting of $CH_2OR^c$ and $CO_2R^c$; the subscript m is 0 to 2 and the subscript p is 0 to 1; each $R^1$ is selected from the group consisting of halogen, nitro, $(C_1$-$C_8)$ alkyl and $(C_1$-$C_8)$ alkoxy; each $R^3$ is selected from the group consisting of halogen, nitro, $(C_1$-$C_8)$ alkyl and $(C_1$-$C_8)$ alkoxy; and $R^2$ is H or $CH_3$. In still further embodiments, X is O and Y is $CO_2R^c$. In yet other embodiments, X is O and Y is $CH_2OR^c$. In still another embodiment, X is NH and Y is $CO_2R^c$. In another embodiment, X is NH and Y is $CH_2OR^c$.

Methods of Making Halofenate

Exemplary processes for making the compounds of the present invention are generally depicted in Schemes 1 and 2:

Scheme 1:

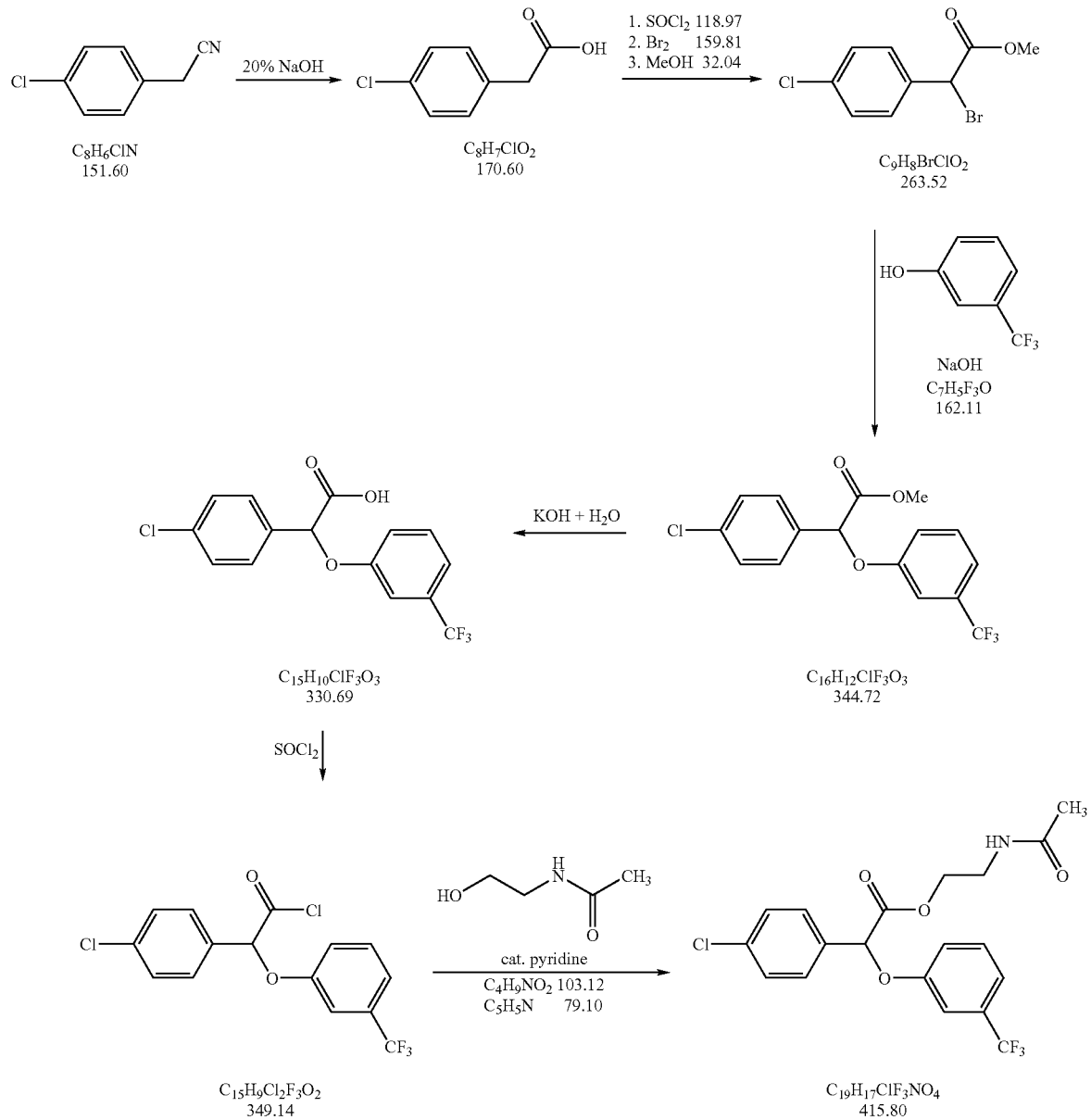

Scheme 2:

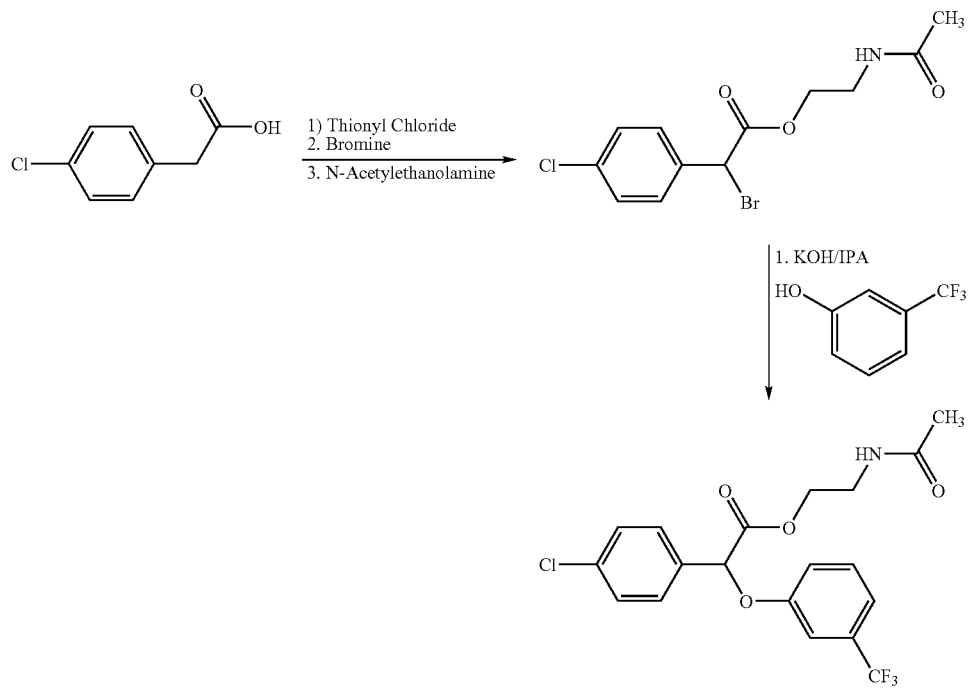

According to Scheme 1, a substituted phenyl acetonitrile is converted to a substituted phenyl acetic acid. The substituted phenyl acetic acid is converted to an activated acid derivative (e.g., acid chloride), followed by halogenation at the alpha-carbon and esterification with an alcohol. The halogenated ester is treated with a substituted phenol (e.g., 3-trifluoromethylphenol), yielding an aryl ether, which is hydrolyzed to form a carboxylic acid derivative. The acid derivated is converted to an activated acid derivative and subsequently treated with a nucleophile (e.g., N-acetylethanolamine) to afford the desired product.

According to Scheme 2, a substituted phenyl acetic acid is converted to an activated acid derivative (e.g., acid chloride) followed by halogenation at the alpha-carbon. The activated acid portion of the molecule is reacted with a nucleophile (e.g., N-acetylethanolamine) to provide a protected acid. The halogenated, protected acid is treated with a substituted phenol (e.g., 3-trifluoromethylphenol), yielding the desired product.

The stereoisomers of the compounds of the present invention can be prepared by using reactants or reagents or catalysts in their single enantiomeric form in the process wherever possible or by resolving the mixture of stereoisomers by conventional methods, discussed supra and in the Examples. Some of the preferred methods include use of microbial resolution, resolving the diastereomeric salts formed with chiral acids or chiral bases and chromatography using chiral supports. See, also U.S. Patent Application Publication No. 20050033084 published Feb. 10, 2005, which is incorporated herein by reference in its entirety and particularly with respect to methods of making and resolving such compounds including halofenate. See, also, U.S. Pat. Nos. 6,646,004; 6,624,194; 6,613,802; and 6,262,118, each to Luskey et al. and which are incorporated herein by reference in their entirety. The synthesis of the compounds of the present invention is further described in the Examples.

The chemical synthesis of racemic mixtures of (3-trihalomethylphenoxy) (4-halophenyl)acetic acid derivatives can also be performed by the methods described in U.S. Pat. No. 3,517,050, the teaching of which are incorporated herein by reference. The individual enantiomers can be obtained by resolution of the racemic mixture of enantiomers using conventional means known to and used by those of skill in the art. See, e.g., Jaques, J., et al., in ENANTIOMERS, PACEMATES, AND RESOLUTIONS, John Wiley and Sons, New York (1981). Other standard methods of resolution known to those skilled in the art, including but not limited to, simple crystallization and chromatographic resolution, can also be used (see, e.g., STEREOCHEMISTRY OF CARBON COMPOUNDS (1962) E. L. Eliel, McGraw Hill; Lochmuller, J. *Chromatography* (1975) 113, 283-302). Additionally, the compounds of the present invention, i.e., the optically pure isomers, can be prepared from the racemic mixture by enzymatic biocatalytic resolution. Enzymatic biocatalytic resolution has been generally described previously (see, e.g., U.S. Pat. Nos. 5,057,427 and 5,077,217, the disclosures of which are incorporated herein by reference). Other generic methods of obtaining enantiomers include stereospecific synthesis (see, e.g., Li, A. J. et al., *Pharm. Sci.* (1997) 86: 1073-1077).

Methods for Screening anti-Edema Activity.

Methods for assessing anti-edemic activity or the lack of edema-causing activity are known to one of ordinary skill in the art. Edema can be assessed according to the number of subjects developing the edema or by the severity of the edema. Improvements in edema can be assessed by comparing subjects administered the test compound to a placebo group. Edema can be assessed by measuring interstitial fluid volumes by use of tracers or MRI imaging. Edema can be indirectly monitored by assessing fluid balance, including urinary output. Given the density and volume of water involved, edema can be assessed by following body weight changes. Clinically, edema may be monitored indirectly by assessing blood pressure or the circumference of extremities (e.g., degree of swelling and proportional area of swelling) or the severity and extent of "pitting" upon application of pressure to the skin. Pulmonary edema can be assessed by patient reports of dyspnea and discomfort or by listening to the chest for the tell-tale signs of fluid accumulation and swelling in the lungs.

Similarly, methods for assessing renal function, heart function, hypertension and the like are well known to one of ordinary skill in the arts.

Methods of Screening for Anti-Lipidemic, Anti-Glycemic, and Anti-Uricemic Activity of the Compounds to be Used According to the Invention.

Methods for screening compounds for the above-recited activities on blood lipids, glucose, and uric acid are well known to one of ordinary skill in the art. Methods of monitoring blood lipids, glucose levels, and uric acid levels are commonly used in medicine and the veterinary arts. U.S. Patent Application Publications No. 20030220399 and 20040029933, and U.S. Pat. Nos. 6,646,004; 6,624,194; 6,613,802; and 6,262,118 which are each incorporated herein by reference illustrate the application of such methods to phenoxyacetic acids. These assays may also be useful in screening for pharmacologically acceptable compounds for use according to the invention.

Methods for Screening for PPARγ Partial Agonism.

Optionally, agents for possible use according to the invention, can be first screened according to their ability to bind to PPARγ. Such first identification of compounds that specifically bind PPARγ can be accomplished by any means known in the art, such as, for example, electrophoretic mobility shift assays and competitive binding assays. One of ordinary skill in the art is readily aware of how to screen compounds for PPARγ activity, including partial agonism. For instance, see European Patent Application Publications Nos. EP1469071, EP1288303, EP1267171, European Patent No. EP1016714, United States Patent Application Publications Nos. 20040077659, 20040010119, 20020119499, 20020031539, and 20030039980; and U.S. Pat. Nos. 6,815,168, 6,200,802, 6,689,574, 6,365,361, and 6365361 which are each incorporated herein by reference with respect to such methodologies. Mammalian PPAR subtypes (e.g., rat, mouse, hamster, rabbit, primate, guinea pig) are preferably used. More preferably, human PPAR subtypes are used.

Electrophoretic mobility shift assays can be used to determine whether test compounds bind to PPARγ and affect its electrophoretic mobility (Forman, et al. (1997) PNAS 94:4312 and Kliewer, et al. (1994) PNAS 91:7355). Electrophoretic mobility shift assays involve incubating a PPAR-RXR with a test compound in the presence of a labeled nucleotide sequence. Labels are known to those of skill in the art and include, for example, radioactive isotopes and non-radioactive labels such as fluorescent labels or chemiluminescent labels. Fluorescent molecules which can be used to label nucleic acid molecules include, for example, fluorescein isothiocyanate and pentafluorophenyl esters. Fluorescent labels and chemical methods of DNA and RNA fluorescent labeling have been reviewed recently (Proudnikov et al., 1996, Nucleic Acids Res. 24:4535-42).

Monoclonal antibodies specific for PPAR subtypes can be used to identify PPARγ specific binding compounds in modified electrophoretic mobility shift assays. Purified PPARβ, PPARα or PPARγ can be incubated with an appropriate amount of a test compound in the presence of RXR. For these assays, the test compound need not be labeled. PPAR subtype specific monoclonal antibodies can be incubated with the PPAR-RXR-test compound mixture. For instance, test compounds that bind PPAR induce supershifting of the PPAR-RXR complex on a gel (Forman, et al. (1997), PNAS 94:4312) which can be detected by anti-PPAR monoclonal antibodies using a Western blot (immunoblot).

In addition to electrophoretic mobility shift assays, competitive binding assays can be used to identify PPARγ specific binding compounds. In competitive assays, the binding of test compounds to PPARγ can be determined by measuring the amount of ligand that they displaced (competed away) from PPARγ. Purified PPAR subtype receptors can be incubated with varying amounts of a test compound in the presence of labeled ligands specific for each PPAR subtype. For example, GW 2433 and L-783483 can be used in conjunction with PPARβ; GW 2331 can be used in conjunction with PPARα; and rosiglitazone, AD-5075, and SB-236636 can be used in conjunction with PPARγ. Specificity of the test compound for each PPAR subtype can be determined by detection of the amount of labeled ligand that remains bound to each PPAR after incubation with the test compound. Labels are discussed above.

The ability of a compound to activate PPARγ can be measured using any means known in the art. PPARγ activators are thought to act by inducing PPARγ-RXR heterodimer formation. The PPARγ-RXR heterodimer then binds to DNA sequences containing the corresponding binding motif and activates PPAR target genes. Preferably PPARγ activators activate PPARγ by at least 5-10 fold, more preferably 10-100 fold, more preferably 100-500 fold, more preferably 500-100 fold, most preferably greater than 1000 fold above base level. PPARγ can be transfected into cells. The transfected cells can be then exposed to candidate compounds. Any means known in the art can be used to determine whether PPARγ is activated by the candidate compound, such as for example, by measuring levels of reporter gene expression and cell proliferation.

Any of the well-known procedures for introducing foreign nucleotide sequences into host cells may be used to transfect PPARγ into cells. Methods of transfection have also been described in U.S. Pat. Nos. 5,616,745, 5,792,6512, 5,965,404, and 6,051,429 and in Current Protocols in Molecular Biology, Ausubel, et al., ed. (2001). It is only necessary that the particular genetic engineering procedure used be capable of successfully introducing at least one gene into the host cell capable of expressing PPARγ. After the expression vector is introduced into the cells, the transfected cells can be cultured under conditions favoring expression of PPARγ.

Expression of reporter genes in response to compounds identified as binders of PPARγ may also be used to measure PPARγ activation. PPARγ may be co-transfected with reporter genes known in the art such as, for example, luciferase, β-galactosidase, alkaline phosphatase, fluorescent green protein, or chloramphenicol acetyltransferase. The transfected cells can be exposed to appropriate concentrations of candidate compounds with rosiglitazone as a positive control. Reporter gene expression will be induced by compounds that bind and activate PPARγ. Thus, compounds that induce reporter gene expression can be identified as activators of PPARγ (Forman, et al. (1997) PNAS 94:4312). Preferably the compounds induce reporter gene expression at levels at least 5-10 fold, more preferably 10-100 fold, more preferably 100-500 fold, more preferably 500-1000 fold, most preferably greater than 1000 fold greater than the negative control.

Upon identifying certain test compounds as potential PPARγ partial agonist, the efficacy and specificity of the selected compounds are further tested both in vitro and in vivo. Whether for subsequent in vivo testing, or for administration to an animal as an approved drug, agents identified in the subject assay can be formulated in pharmaceutical preparations, such as described above, for in vivo administration to an animal, preferably a human.

The effectiveness of treatment may be determined by controlled clinical trials. Patients having cancer with measurable or evaluable tumors will be included in the study. A measurable tumor is one that can be measured in at least two dimensions such as a lung tumor surrounded by aerated lung, a skin nodule, or a superficial lymph node. An evaluable tumor in one that can be measured in one dimension such as a lung tumor not completely surrounded by aerated lung or a palpable abdominal or soft tissue mass that can be measured in one dimension. Tumor markers which have been shown to be highly correlated with extent of disease will also be considered to provide an evaluable disease, such as PSA for prostate cancer, CA-125 for ovarian cancer, CA-15-3 for breast cancer, etc.

The tumor can be measured or evaluated before and after treatment by whatever means provides the most accurate measurement, such as CT scan, MRI scan, Ultrasonography, etc. New tumors or the lack thereof in previously irradiated fields can also be used to assess the anti-tumor response. The criteria for evaluating response will be similar to that of the WHO Handbook of Reporting Results of Cancer Treatment, WHO Offset Publication 1979, 49-World Health Organization, Geneva. The following results are defined for uni- and bi-dimensionally measurable tumors.

Complete response: Complete disappearance of all clinically detectable malignant disease determined by two observations not less than four weeks apart.

Partial Response: (a) for bidimensionally measurable tumors, a decrease of at least 50% in the sum of the products of the largest perpendicular diameters of all measurable tumors as determined by two observations not less than four weeks apart. (b) for unidimensionally measurable tumors, a decrease by at least 50% in the sum of the largest diameters of all tumors as determined by two observations not less than four weeks apart. In cases where the patient has multiple tumors, It is not necessary for all tumors to have regressed to achieve a partial response as defined herein, but no tumor should have progressed and no new tumor should appear.

Stable disease: (a) for bidimensionally measurable tumors, less than a 50% decrease to less than a 25% increase in the sum of the products of the largest perpendicular diameters of all measurable tumors. (b) for unidimensionally measurable tumors, less than a 50% decrease to less than a 25% increase in the sum of the diameters of all tumors. For (a) and (b) no new tumors should appear.

No clinical response, i.e. progressive disease in defined as an increase of more than 50% in the product of the largest perpendicular diameters for at least one bidimensionally measurable tumor, or an increase of more than 25% in measurable dimension of at least one unidimensionally measurable tumor.

Of course elimination or alleviation of other known signs or symptoms of cancer, especially those listed previously can also be used to evaluate the effectiveness of this invention The cancers should be evaluated, i.e. tumors measured, etc., no more than 14 days before the start of the treatment. These cancers should be reevaluated about 28 days after day 1 of administration of the first dose. Twenty eight days after this initial administration another administration period may be performed, and evaluations performed 28 days after the start of this second cycle. The treatment cycles may be continued until a clinical response is achieved or unacceptable toxicity is encountered.

Many methods for screening anti-cancer agents are known in the art. In particular, for instance, one can study the effects of an agent on the growth of subcutaneous implants of tumour cells in immunodeficient mice who have been implanted subcutaneously with a tumor of interest. For instance, 4 week old nude mice can be injected s.c. at 4 different sites with tissue culture medium containing human cancer cells. The mice can then be treated with various dosages of a compound and the effects of the agents on tumor size and histology and appearance and mouse survival time and frequency can be monitored over the course of the experiment. The tumor volume can be assessed three times a week using calipers to measure the perpendicular diameters of the tumor, and the volume calculated therefrom. Animals' weights can also be measured 3 times a week.

The ability of an agent according to the invention to induce apoptosis or inhibit the growth or survival of a cancer cell in vitro can also be assessed according to any of the methods known to one of ordinary skill in the art. For instance, one can (i) establish cultures of PPARγ-responsive hyperproliferative cells; (ii) contact the transformed cells with a test compound; and (iii) detect one of proliferation and/or differentiation, wherein compounds are selected by observing a statistically significant decrease in the extent of proliferation (or in the appearance of a differentiated phenotype) in the presence of the test compound. For example, changes in the proliferation of test cells can be assayed by comparing the number of cells labeled with bromo-deoxy uridine (BrdU) in cultures treated with a potential PPARγ partial agonist compared to untreated controls. The extent of, for example, adipocyte differentiation, for example, can be determined by detecting at least one of changes in cell morphology, accumulation of intracellular lipid, induction of adipocyte-specific genes, e.g., aP2 and adipsin, and/or withdrawal from the cell cycle.

Prior to testing a compound in the cell-based assay, simple binding assays, e.g., using purified or semi-purified PPAR-.gamma. protein, can be used to isolate those test compounds which at least bind to the receptor.

Assays can be based upon the ability of PPARγ modulators to induce cell cycle withdrawal, induce terminal differentiation of human liposarcoma cells, or reduce the size of adipose cell tumors in vivo, inhibit proliferation of leukemic cells, inhibit proliferation of prostate cancer cells, induce terminal differentiation of human breast cancer cells (See, U.S. Pat. No. 6,242,196 which is incorporated herein by reference and particularly with respect to how such methods can be conducted).

Pharmaceutical Compositions and Methods of Treating Diseases and Conditions

In accordance with the present invention, a therapeutically effective amount of a compound of Formula I, II, III, IVa, IVb, V, VI, or VII can be used for the preparation of a pharmaceutical composition useful for treating or preventing edema and the various other conditions and diseases set forth above.

The compositions of the invention can include compounds of Formula I, II, III, IVa, IVb, V, VI, or VII, pharmaceutically acceptable salts thereof, or a hydrolyzable precursor thereof. In general, the compound is mixed with suitable carriers or excipient(s) in a therapeutically effective amount. By a "therapeutically effective dose", "therapeutically effective amount", or, interchangeably, "pharmacologically acceptable dose" or "pharmacologically acceptable amount", it is meant that a sufficient amount of the compound of the present invention and a pharmaceutically acceptable carrier, will be present in order to achieve a desired result, e.g., alleviating a symptom or complication of edema.

The compounds of Formula I, II, III, IVa, IVb, V, VI, or VII that are used in the methods of the present invention can be incorporated into a variety of formulations for therapeutic administration. More particularly, the compounds of Formula I, II, III, IVa, IVb, V, VI, or VII can be formulated into pharmaceutical compositions by combination with appropriate, pharmaceutically acceptable carriers or diluents, and can be formulated into preparations in solid, semi-solid, liquid or gaseous forms, such as tablets, capsules, pills, powders, granules, dragees, gels, slurries, ointments, solutions, suppositories, injections, inhalants and aerosols. As such, administration of the compounds can be achieved in various ways, including oral, buccal, rectal, parenteral, intraperitoneal, intradermal, transdermal, intratracheal administration. Moreover, the compound can be administered in a local rather than systemic manner, in a depot or sustained release formulation. In addition, the compounds can be administered in a liposome.

The compounds of Formula I, II, III, IVa, IVb, V, VI, or VII can be formulated with common excipients, diluents or carriers, and compressed into tablets, or formulated as elixirs or solutions for convenient oral administration, or administered by the intramuscular or intravenous routes. The compounds can be administered transdermally, and can be formulated as sustained release dosage forms and the like. compounds of Formula I, II, III, IVa, IVb, V, VI, or VII can be administered alone, in combination with each other, or they can be used in combination with other known compounds useful in the treatment of a subject's particular condition. In some embodiments, the compounds are co-administered to a subject being treated with an agent known to cause or causally associated with edema in treated subjects.

Suitable formulations for use in the present invention are found in *Remingtion's Pharmaceutical Sciences* (Mack Publishing Company (1985) Philadelphia, Pa., 17th ed.), which is incorporated herein by reference. Moreover, for a brief review of methods for drug delivery, see, Langer, *Science* (1990) 249:1527-1533, which is incorporated herein by reference. The pharmaceutical compositions described herein can be manufactured in a manner that is known to those of skill in the art, i.e., by means of conventional mixing, dissolving, granulating, dragee-making, levigating, emulsifying, encapsulating, entrapping or lyophilizing processes. The following methods and excipients are merely exemplary and are in no way limiting.

For injection, the compounds can be formulated into preparations by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives. Preferably, the compounds of the present invention can be formulated in aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the compounds of Formula I, II, III, IVa, IVb, V, VI, or VII can be formulated readily by combining with pharmaceutically acceptable carriers that are well known in the art. Such carriers enable the compounds to be formulated as tablets, pills, dragees, capsules, emulsions, lipophilic and hydrophilic suspensions, liquids, gels, syrups, slurries, suspensions and the like, for oral ingestion by a patient to be treated. Pharmaceutical preparations for oral use can be obtained by mixing the compounds with a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents can be added, such as the cross-linked polyvinyl pyrrolidone, agar, or alginic acid or a salt thereof such as sodium alginate.

Dragee cores are provided with suitable coatings. For this purpose, concentrated sugar solutions can be used, which can optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds can be dissolved or suspended in suitable liquids, such as fatty oils, liquid paraffin, or liquid polyethylene glycols. In addition, stabilizers can be added. All formulations for oral administration should be in dosages suitable for such administration. For instance, these doses is from 100 to 800 mg per day by the oral route, or from about 200 mg to about 400 mg by the oral route.

For buccal administration, the compositions can take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas, or from propellant-free, dry-powder inhalers. In the case of a pressurized aerosol the dosage unit can be determined by providing a valve to deliver a metered amount. Capsules and cartridges of, e.g., gelatin for use in an inhaler or insufflator can be formulated containing a powder mix of the compound and a suitable powder base such as lactose or starch.

The compounds can be formulated for parenteral administration by injection, e.g., by bolus injection or continuous infusion. Formulations for injection can be presented in unit dosage form, e.g., in ampules or in multidose containers, with an added preservative. The compositions can take such forms as suspensions, solutions or emulsions in oily or aqueous vehicles, and can contain formulator agents such as suspending, stabilizing and/or dispersing agents.

Pharmaceutical formulations for parenteral administration include aqueous solutions of the active compounds in water-soluble form. Additionally, suspensions of the active compounds can be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions can contain substances which increase the viscosity of the suspension, such as sodium carboxymethyl cellulose, sorbitol, or dextran. Optionally, the suspension can also contain suitable stabilizers or agents which increase the solubility of the compounds to allow for the preparation of highly concentrated solutions. Alternatively, the active ingredient can be in powder form for constitution with a suitable vehicle, e.g., sterile pyrogen-free water, before use.

The compounds can also be formulated in rectal compositions such as suppositories or retention enemas, e.g., containing conventional suppository bases such as cocoa butter, carbowaxes, polyethylene glycols or other glycerides, all of which melt at body temperature, yet are solidified at room temperature.

In addition to the formulations described previously, the compounds can also be formulated as a depot preparation. Such long acting formulations can be administered by implantation (for example subcutaneously or intramuscularly) or by intramuscular injection. Thus, for example, the compounds can be formulated with suitable polymeric or hydrophobic materials (for example as an emulsion in an acceptable oil) or ion exchange resins, or as sparingly soluble derivatives, for example, as a sparingly soluble salt.

Alternatively, other delivery systems for hydrophobic pharmaceutical compounds can be employed. Liposomes and emulsions are well known examples of delivery vehicles or carriers for hydrophobic drugs. In a presently preferred embodiment, long-circulating, i.e., stealth liposomes can be employed. Such liposomes are generally described in Woodle, et al., U.S. Pat. No. 5,013,556. The compounds of the present invention can also be administered by controlled release means and/or delivery devices such as those described in U.S. Pat. Nos. 3,845,770; 3,916,899; 3,536,809; 3,598,123; and 4,008,719.

Certain organic solvents such as dimethylsulfoxide (DMSO) also can be employed, although usually at the cost of greater toxicity. Additionally, the compounds can be delivered using a sustained-release system, such as semipermeable matrices of solid hydrophobic polymers containing the therapeutic agent. Various types of sustained-release materials have been established and are well known by those skilled in the art. Sustained-release capsules can, depending on their chemical nature, release the compounds for a few hours up to over 100 days.

The pharmaceutical compositions also can comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Pharmaceutical compositions suitable for use in the present invention include compositions wherein the active ingredients are contained in a therapeutically effective amount. The amount of composition administered will, of course, be dependent on the subject being treated, on the subject's weight, the severity of the affliction, the manner of administration and the judgment of the prescribing physician. Determination of an effective amount is well within the capability of those skilled in the art, especially in light of the detailed disclosure provided herein.

For any compound used in the method of the present invention, a therapeutically effective dose can be estimated initially from cell culture assays or animal models.

Moreover, toxicity and therapeutic efficacy of the compounds described herein can be determined by standard pharmaceutical procedures in cell cultures or experimental animals, e.g., by determining the $LD_{50}$, (the dose lethal to 50% of the population) and the $ED_{50}$ (the dose therapeutically effective in 50% of the population). The dose ratio between toxic and therapeutic effect is the therapeutic index and can be expressed as the ratio between $LD_{50}$ and $ED_{50}$. compounds which exhibit high therapeutic indices are preferred. The data obtained from these cell culture assays and animal studies can be used in formulating a dosage range that is not toxic for use in human. The dosage of such compounds lies preferably within a range of circulating concentrations that include the $ED_{50}$ with little or no toxicity. The dosage can vary within this range depending upon the dosage form employed and the route of administration utilized. The exact formulation, route of administration and dosage can be chosen by the individual physician in view of the patient's condition. (See, e.g., Fingl et al 1975 In: *The Pharmacological Basis of Therapeutics*, Ch. 1).

The amount of active compound that can be combined with a carrier material to produce a single dosage form will vary depending upon the disease treated, the mammalian species, and the particular mode of administration. However, as a general guide, suitable unit doses for the compounds of the present invention can, for example, preferably contain between 100 mg to about 3000 mg of the active compound. A preferred unit dose is between 100 mg to about 1000 mg. A more preferred unit dose is between 100 to about 600 mg. Such unit doses can be administered more than once a day, for example 2, 3, 4, 5 or 6 times a day, but preferably 1 or 2 times per day, so that the total daily dosage for a 70 kg adult is in the range of 0.1 to about 250 mg per kg weight of subject per administration. A preferred dosage is 5 to about 250 mg per kg weight of subject per administration, and such therapy can extend for a number of weeks or months, and in some cases, years. A more preferred dosage is from 2 mg/kg to about 10 mg/kg. It will be understood, however, that the specific dose level for any particular patient will depend on a variety of factors including the activity of the specific compound employed; the age, body weight, general health, sex and diet of the individual being treated; the time and route of administration; the rate of excretion; other drugs which have previously been administered; and the severity of the particular disease undergoing therapy, as is well understood by those of skill in the area.

A typical dosage can be one 10 to about 1500 mg tablet taken once a day, or, multiple times per day, or one time-release capsule or tablet taken once a day and containing a proportionally higher content of active ingredient. In some embodiments, the dosage can be a 50 to 800 mg or a 200 to 600 mg tablet taken once a day, or, multiple times per day, or one time-release capsule or tablet taken once a day and containing a proportionally higher content of active ingredient. The time-release effect can be obtained by capsule materials that dissolve at different pH values, by capsules that release slowly by osmotic pressure, or by any other known means of controlled release.

It can be necessary to use dosages outside these ranges in some cases as will be apparent to those skilled in the art. Further, it is noted that the clinician or treating physician will know how and when to interrupt, adjust, or terminate therapy in conjunction with individual patient response.

For the compositions provided above, one of skill in the art will understand that preferred compounds for use in each are those compounds that are preferred above and particularly those compounds provided in formulae IIa through IIat, and IIIa through IIIt in FIGS. 2, 3, 4A, 4B, 5A, 5B and 5C. Still further preferred compounds for the compositions, methods and kits are those compounds provided in the Examples below.

EXAMPLE 1

This example relates to the preparation of Methyl Bromo-(4-chlorophenyl)-acetate:

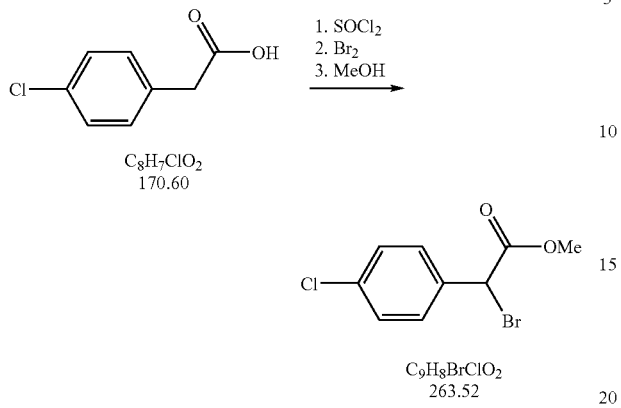

The initial compound listed in Scheme 1, i.e., 4-chlorophenylacetic acid, is readily available from several commercial sources (e.g., Aldrich and Fluka).

A 5-L Morton reactor equipped with a magnetic stirrer, a pot temperature control, and addition funnel was vented through a gas scrubber and charged with p-chlorophenylacetic acid (720 gm, 4.2 moles) and $SOCl_2$ (390 ml, 630 gm, 5.3 moles). The reaction was stirred, heated and held at 55°±5° C. for 1 hour. Bromine (220 ml., 670 gm, 5.3 moles) was then added over 20 min. and stirred at 55°±5° C. for 16 hours. The temperature was raised to 80° C. for 7 hours and then cooled to 9° C. in an ice-water bath. Methanol (2.0 L, 1.6 kg, 49.4 moles) was then carefully added. The solvent was stripped to obtain 2 liquids weighing 1.28 kg. These were dissolved in a mixture of 0.84 L water and 2.1 L ether and separated. The organic phase was washed once with 0.78 L 25% (w:w) aqueous NaCl and dried over 0.13 kg $MgSO_4$. This was filtered through Whatman #1 filter paper and stripped of solvent to obtain 0.985 kg of orange liquid. The proton NMR showed this to be 80% product and 19% non-brominated ester. The HPLC showed 82% product and 18% non-brominated ester. HPLC was run on a Zorbax SB-C8 column at 30° C. measuring 250×4.6 mm and 5μ particle size. The mobile phase was 60:40 (v:v) acetonitrile: 0.1% $H_3PO_4$ at 1.5 ml/min. Detection was at 210 nm. The injected sample of 1 μl was dissolved in acetonitrile at a concentration of 10 mg/ml. The product had a retention time of 5.0 min. and that of the non-brominated ester was 3.8 min. This crude product was purified by vacuum distillation to obtain 96% pure product with an 84% yield. The product proton NMR ($CDCl_3$, 300 MHz) showed shifts at 3.79 (s, 3H), 5.32 (s, 1H) and 7.20-7.55 (m, 4H) ppm.

EXAMPLE 2

This example relates to the preparation of Methyl 4-Chlorophenyl-(3-trifluoromethylphenoxy)-acetate:

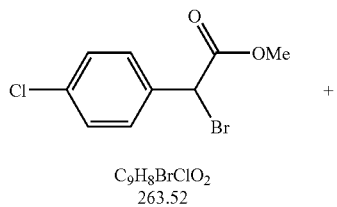

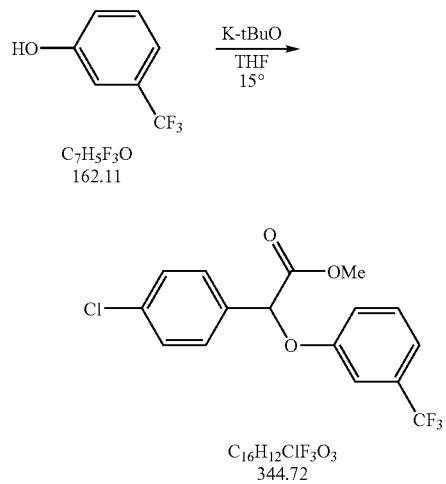

This step was similar to the same step in U.S. Pat. No. 3,517,050 with one exception; potassium t-butoxide was used in place of sodium methoxide to prevent generation of the corresponding methyl ether. A 5-L Morton reactor equipped with an overhead stirrer, a pot temperature detector, and addition funnel and under a nitrogen atmosphere was charged with methyl bromo-(4-chlorophenyl)-acetate (830 gm, 3.0 moles) and THF (600 ml). The reactor was cooled to 14°±3° C. in an ice-water bath and then a similarly cooled solution of trifluoromethyl-m-cresol (530 gm, 3.3 moles) in 1.0 M potassium t-butoxide in THF (3.1 L, 3.1 moles) was added. The reaction proceeded exothermically with a typical temperature rise exceeding 25° C. and the addition was controlled to maintain a temperature of 15°±2° C. and stirred at ambient temperature for 2 hours. HPLC was run on a Zorbax SB-C8 column at 30° C. measuring 250×4.6 mm and 5μ particle size. The mobile phase was 60:40 (v:v) acetonitrile: 0.1% $H_3PO_4$ at 1.5 ml/min. Detection was at 210 nm. The injected sample of 1 μl was dissolved in acetonitrile at a concentration of 10 mg/ml. The product had a retention time of 9.6 min., the starting ester eluted at 5.0 min., the phenol at 3.0 and the non-brominated ester at 3.8 min. The solvent was stripped using a rotary evaporator to obtain a yellow slush that was dissolved in a mixture of 4.0 L water and 12.0 L ether. The mixture was separated and the organic phase was washed once with 1.6 L 5% (w:w) aqueous NaOH followed by 1.6 L water and finally 1.6 L 25% (w:w) aqueous NaCl. The organic phase was dried over 0.32 kg $MgSO_4$ and filtered through Whatman #1 filter paper. The solvent was stripped to obtain 1.0 kg of damp, off-white crystals. This was recrystallized on the rotary evaporator by dissolving in 1.0 L methylcyclohexane at 75° C. and then cooling to 20° C. The crystals were filtered through Whatman #1 filter paper and washed with three 0.25 L portions of cool (15° C.) methylcyclohexane. The wet product (0.97 kg) was dried overnight to obtain 0.81 kg of 98% pure product that corresponds to a 79% yield. The product proton NMR ($CDCl_3$, 300 MHz) shows shifts at 3.75 (s, 3H), 5.63 (s, 1H) and 7.05-7.55 (m, 8H).

EXAMPLE 3

This example relates to the preparation of 4-Chlorophenyl-(3-trifluoromethylphenoxy)-acetic Acid:

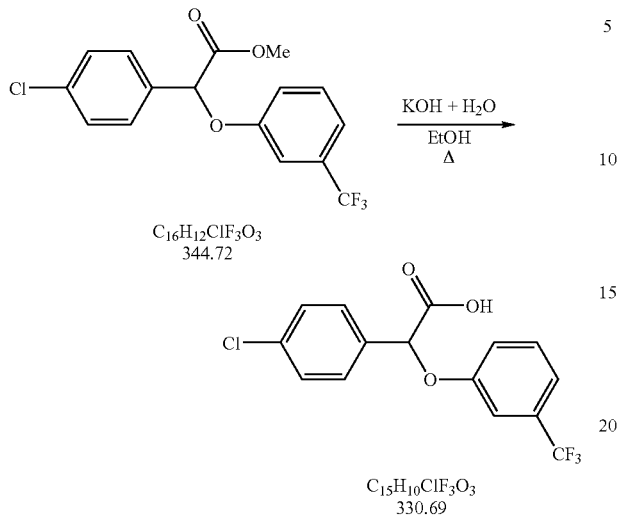

A 12-L Morton reactor with magnetic stirrer, pot temperature controller, a reflux condenser and under a nitrogen atmosphere was charged with methyl 4-chlorophenyl-(3-trifluoromethylphenoxy)-acetate (810 gm, 2.3 moles) and absolute ethanol (5.8 L) and heated with stirring to 57° C. to dissolve the solid. A solution of KOH (520 gm, 9.3 moles) in 0.98 L water was added. The solution was refluxed for 30 min. and solvent was stripped by a rotary evaporator to obtain 2.03 kg of a mixture of two nearly colorless liquids. These were dissolved in water (16 L) and treated with 16 gm neutral Norit, then filtered through a pad of infusorial earth retained on Whatman #1 filter paper. The pH of the filtrate was lowered from an initial range of 13 to a range of 1 to 2 by adding a total of 2.75 L of 3 M HCl (8.25 moles). A very sticky solid formed after the addition of the first 2.30 L of acid and ether (7 L) was added at this point. The two layers were separated and the organic layer was dried over $MgSO_4$ (230 gm) and filtered through Whatman #1 filter paper. The solvent was then stripped to obtain 0.85 kg water-white syrup. The material was then recrystallized on the rotary evaporator by adding methylcyclohexane (800 ml) and cooling to 18° C. with slow rotation. The temperature was then dropped to 5° C., the crystals were filtered, and washed 5 times with 0.10 L portions of cold (0° C.) methylcyclohexane to obtain 0.59 kg wet crystals. The wet crystals were dried to obtain 0.48 kg (62% yield) product with no p-chlorophenylacetic acid detectable in the proton NMR. The product proton NMR ($CDCl_3$, 300 MHz) shows shifts at 5.65 (s, 1H), 7.02-7.58 (m, 8H) and 10.6 (s, 1H).

EXAMPLE 4

This example relates to the preparation of resolved enantiomers of 4-Chlorophenyl-(3-trifluoromethylphenoxy)-acetic Acid:

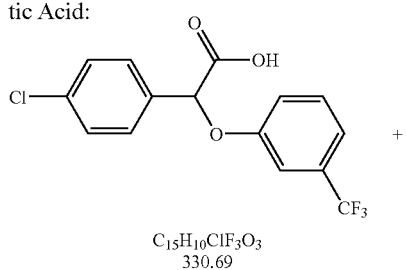

+

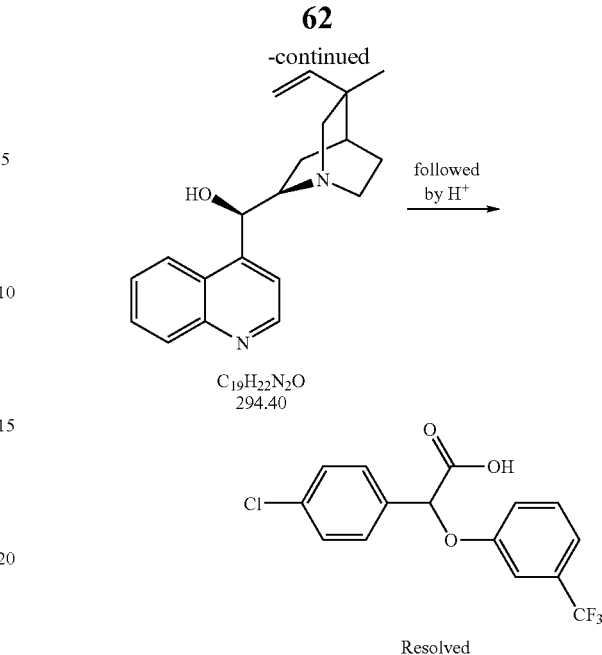

A 12-L open-top Morton reactor with an overhead stirrer was charged with 4-chlorophenyl-(3-trifluoromethyl-phenoxy)-acetic acid (350 gm, 1.06 moles) and isopropanol (4.0 L) and heated to 65°±3° C. A slurry of (−) cinchonidine (300 gm, 1.02 moles) in isopropanol (2.0 L) was added, rinsing all solid into the reactor with an additional 0.8 L of isopropanol. The temperature dropped from 65° to 56° C. and a transparent, orange solution ultimately formed and the mixture was held at 55°±5° C. for 2 hours. Fine crystals were collected by filtration through Whatman #1 filter paper, washing once with 0.7 L hot (55° C.) isopropanol. The crystals were dried for 16 hours at ambient temperature in a 12.6-L vacuum oven under a 5 LPM nitrogen flow. The dry solid weighed 0.37 kg and had an 80% enantiomeric excess (ee) of the (+) enantiomer. The enantiomeric excess was determined by HPLC using a 250× 4.6 mm R,R-WhelkO-1 column at ambient temperature. Injected samples were 20 µl of 2 mg/ml solutions of the samples in ethanol. The column was eluted with 95:5:0.4, hexane:isopropanol:acetic acid at a flow of 1 ml/min. Detection was at 210 nm. The (+) enantiomer eluted at 7 to 8 min. and the (−) enantiomer at 11 to 13 min. The mother liquor dropped a second crop almost immediately that was filtered, washed, and dried to afford 0.06 kg salt that has a 90% ee of the (−)-enantiomer. Similarly third, fourth and fifth crops weighing 0.03 kg, 0.03 kg and 0.7 kg, respectively, were obtained; with (−) enantiomer excesses of 88%, 89% and 92%, respectively.

The crude (+) salt (320 gm) was recrystallized from a mixture of ethanol (5.9 L) methanol (1.2 L). The mixture was heated with overhead stirring to dissolve, cooled at ambient temperature for 16 hours, filtered and washed twice with 0.20 L of 5:1 (v:v) ethanol:methanol. The crystals were dried to obtain 0.24 kg of the (+) enantiomer that had an ee of 97%. This corresponded to an 80% recovery of this isomer. The resolved salt was suspended in a mixture of ether (6.5 L) and water (4.0 L) with overhead stirring. The pH was lowered to 0-1 as measured by pH indicating strips with a solution of concentrated H2SO4 (0.13 L) in water (2.5 L). The phases were separated and the organic phase and washed twice with 6.5 L portions of water. Ether (1.9 L) was added and the organic layer washed once more with 6.5 L water. After the final separation, 0.1 L of 25% (w:w) aqueous NaCl was added clean up any slight emulsion. The product was dried over 0.19 kg MgSO₄, filtered and solvent removed solvent to obtain 0.13 kg of water-white syrup that solidifies on cooling. This corresponded to a 97% recovery of product that had a 95% ee of the (+) enantiomer. [α]$_D$+5.814° (c.=0.069 in methyl alcohol).

The combined, crude (−) salt (200 gm) was recrystallized from isopropanol (3.1 L). The mixture was heated to dissolve almost all of the solid and fast-filtered to remove insoluble solids. The mixture was then cooled with stirring at ambient temperature for 16 hours, filtered, washed, and dried to obtain 0.16 kg of the (−) enantiomer that has an ee of 97%. This corresponds to a 49% recovery of this isomer. The (−) enantiomer of the acid was isolated in the same manner as described above for the (+) acid. The resolved salt was suspended in ether and water, the pH lowered with concentrated H₂SO₄, and the product extracted in the organic phase.

EXAMPLE 5

This example relates to the making of either isomer of halofenate;

A. Preparation of (−) 4-Chlorophenyl-(3-trifluoromethylphenoxy)-acetyl Chloride

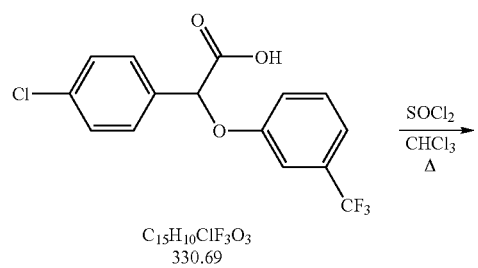

A 2-L evaporation flask with magnetic stirrer, Claissen adapter, pot thermometer and a reflux condenser routed to a gas scrubber was charged with (−) 4-chlorophenyl-(3-trifluoromethylphenoxy)-acetic acid (143 g, 0.42 mole based on 97% purity) and CHCl₃ (170 ml) and heated to boiling in order to dissolve. SOCl₂ (38 ml, 62.1 gm, 0.52 mole) was added. The mixture was heated to reflux (68° C. final) for 4.5 hours and then stripped of volatiles to obtain 151 g yellow, turbid liquid (103% apparent yield). The material was used in the next step without further purification.

B. Preparation of (+) 4-Chlorophenyl-(3-trifluoromethylphenoxy)-acetyl Chloride

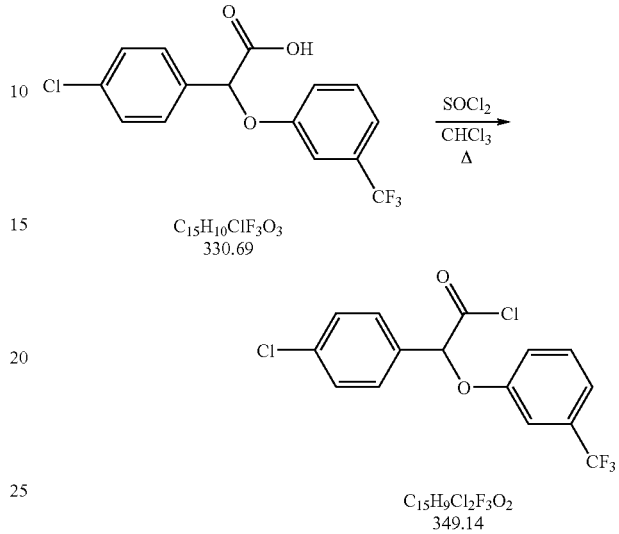

A 3-L evaporation flask with magnetic stirrer, Claissen adapter, pot thermometer and a reflux condenser routed to a gas scrubber was charged with (+) 4-chlorophenyl-(3-trifluoromethylphenoxy)-acetic acid (131 g, 0.37 mole) and CHCl₃ (152 ml) and heated to boiling in order to dissolve. SOCl₂ (35 ml, 56.5 g, 0.48 mole) was added. The mixture was heated to reflux (70° C. final) for 4 hours and then stripped of volatiles to obtain 139 g liquid. The material was used in the next step without further purification.

EXAMPLE 6

This example further illustrates making the (+) and (−) isomers of halofenate.

A. Preparation of (−) 2-Acetamidoethyl 4-Chlorophenyl-(3-trifluoromethylphenoxy)-acetate

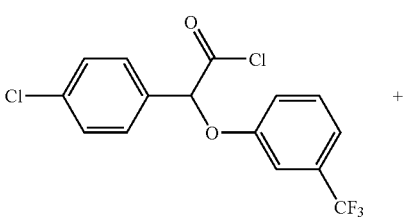

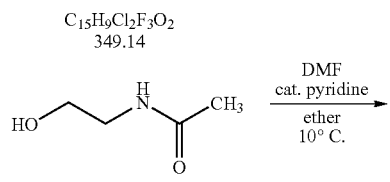

-continued

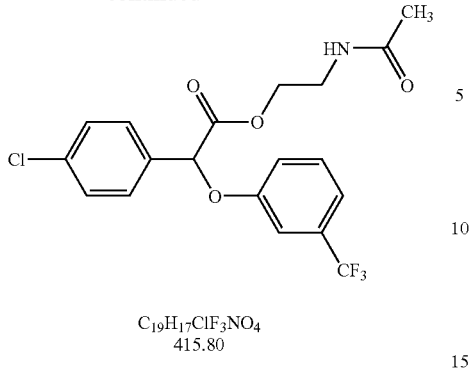

C$_{19}$H$_{17}$ClF$_3$NO$_4$
415.80

A 3-L round-bottom flask with magnetic stirrer, pot thermometer, under a nitrogen atmosphere and in an ice-water bath was charged with DMF (420 ml), pyridine (37 ml, 36 g, 0.46 mole) and N-acetoethanolamine (39 ml, 43 g, 0.42 mole). The mixture was cooled to 0° to 5° C. and a solution of crude (−) 4-chlorophenyl-(3-trifluoromethylphenoxy)-acetyl chloride (151 gm, 0.42 mole based on 100% yield of previous step) in ether (170 ml) was added over a 40 min. period so as to maintain the pot temperature below 13° C. The mixture was stirred at ambient temperature for 16 hours and dissolved by adding water (960 ml) followed by ethyl acetate (630 ml). The water addition proceeded exothermically raising the temperature from 24° to 34° C. Ethyl acetate addition caused a temperature drop to 30° C. The layers were separated and the aqueous phase extracted once with ethyl acetate (125 ml). The combined organic layers were extracted once with 7% (w:w) aqueous NaHCO$_3$ (125 ml) and five times with 60 ml portions of water and then twice with 60 ml portions of 25% (w:w) aqueous NaCl. The product was dried over MgSO$_4$ (42 g) and filtered through Whatman #1 filter paper. Solvent was stripped using a rotary evaporator to obtain 160 g of a yellow syrup corresponding to an 80% yield based on the proton NMR that shows 87% product, 8% EtOAc, 4% non-brominated amide, and 1% DMF. This syrup was dissolved in MTBE (225 ml) at ambient temperature and chilled (−15° C.) 85% hexanes (400 ml) was added with stirring. Two liquids formed, then crystals, then the mixture formed a solid. The solid mass was scraped onto a Buchner funnel fitted with Whatman #1, packed down and washed three times with 100 ml portions of 1:1 (v:v) MTBE:hexanes to obtain 312 g wet product which dries to 127 gm, corresponding to a 73% yield.

B. Preparation of (+) 2-Acetamidoethyl 4-Chlorophenyl-(3-trifluoromethylphenoxy)-acetate

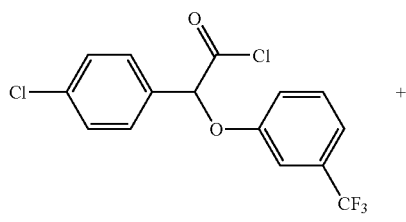

C$_{15}$H$_9$Cl$_2$F$_3$O$_2$
349.14

+

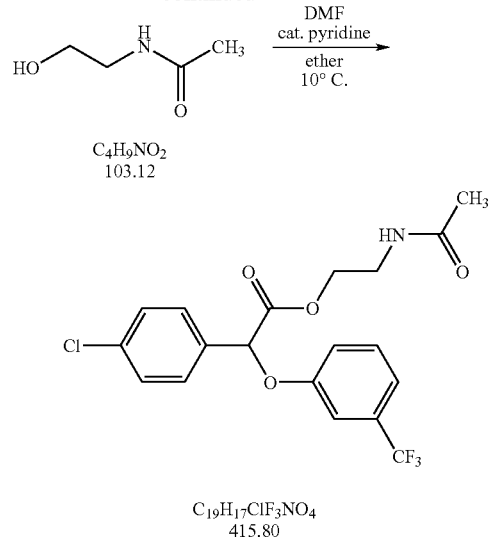

C$_4$H$_9$NO$_2$
103.12

C$_{19}$H$_{17}$ClF$_3$NO$_4$
415.80

A 3-L round-bottom flask with magnetic stirrer, pot thermometer, under a nitrogen atmosphere and in an ice-water bath was charged with DMF (365 ml), pyridine (33 ml, 32.3 g, 0.41 mole) and N-acetoethanolamine (34 ml, 38.1 g, 0.37 mole). The mixture was cooled to 0° to 5° C. and a solution of crude (+) 4-chlorophenyl-(3-trifluoromethylphenoxy)-acetyl chloride (139 gm, 0.37 mole based on 100% yield of previous step) in ether (155 ml) was added over a 25 min. period so as to maintain the pot temperature below 13° C. The mixture was stirred at ambient temperature 40 hours and dissolved by adding water (850 ml) followed by ethyl acetate (550 ml). The water addition proceeded exothermically raising the temperature from 24° to 34° C. Ethyl acetate addition caused a temperature drop to 30° C. The layers were separated and the aqueous phase extracted once with ethyl acetate (110 ml). The combined organic layers were washed twice with 55 ml portions of water and then five times with 55 ml portions of 25% (w:w) aqueous NaCl and dried over 30 g MgSO$_4$ and filtered through Whatman #1 filter paper. Solvent was stripped using a rotary evaporator to obtain 168 g yellow liquid corresponding to an 86% yield based on the proton NMR that shows 79% product, 9% EtOAc, 8% non-brominated amide, and 4% DMF. The product was crystallized in an 800-ml beaker by dissolving in MTBE (200 ml) at ambient temperature, cooling at −15° for 1.4 hours, adding 200 ml 85% hexanes and then chilling 1 hour. The solid mass was scraped out onto a Buchner funnel fitted with Whatman #1, packed down and washed once with 1:1 (v:v) MTBE:hexanes (100 ml) to obtain 201 gm wet product. The product was dried under nitrogen flow and triturated with 85% hexanes (700 ml) using an overhead stirrer. The material was filtered and dried to obtain 87 gm product. [α]$_D$+2.769° (c.=0.048 in methyl alcohol). [α]$_D$−2.716° (c.=0.049 in methyl alcohol). The (+) and (−) enantiomers were also analyzed by HPLC using a 250×4.6 mm R,R-WhelkO-1 column at ambient temperature. Injected samples were 20 μl of 2 mg/ml solutions of the samples in ethanol. The column was eluted with 60:40, isopropanol:hexane at a flow of 1 ml/min. Detection was at 220 nm. The (+) enantiomer eluted at 5.0 to 5.2 min. and the (−) enantiomer at 5.7 to 5.9 min.

EXAMPLE 7

This example describes the preparation of (−) 2-Acetamidoethyl 4-Chlorophenyl-(3-trifluoro methylphenoxy)-acetate ((−) halofenate).

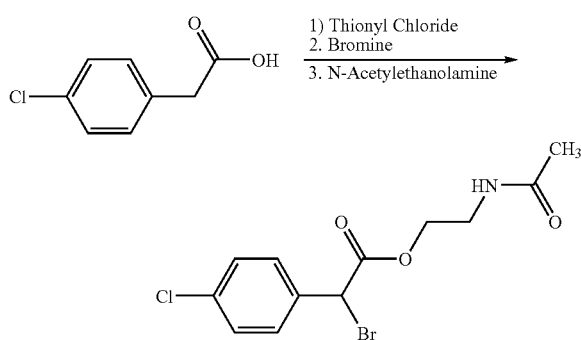

4-Chlorophenylacetic acid was combined with 1,2-dichloroethane and the resulting solution was heated to 45° C. Thionyl chloride was added to the reaction mixture, which was heated at 60° C. for 18 hours. The reaction was allowed to cool to room temperature and was then added slowly to a solution of N-acetylethanolamine in dichloromethane. After stirring 30 min., the reaction was quenched with aqueous potassium carbonate and sodium thiosulfate. The organic layer was washed with water, dried over magnesium sulfate and filtered. Removal of the solvent by rotary evaporation provided N-acetylaminoethyl 2-bromo-2-(4-chlorophenyl) acetate as an oil.

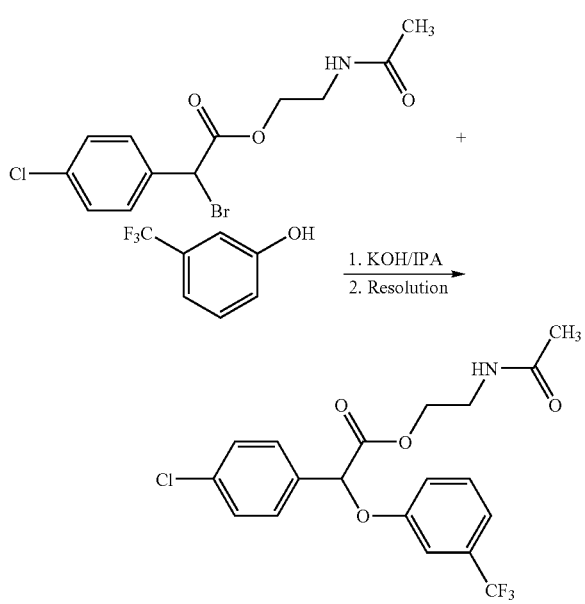

3-Hydroxybenzotrifluoride was added to a solution of potassium hydroxide in isopropanol. N-acetylaminoethyl 2-bromo-2-(4-chlorophenyl)acetate in isopropanol was added to the isopropanol/phenoxide solution and stirred at room temperature for 4 hours. The isopropanol was removed by vacuum distillation, and the resulting slush was dissolved in ethyl acetate and washed twice with water and once with brine. After drying over magnesium sulfate and filtration, the solvent was removed to give crude product as an oil. The crude product was dissolved in hot toluene/hexanes (1:1 v/v) and cooled to between 0 and 10° C. to crystallize the product. The filter cake was washed with hexanes/toluene (1:1 v/v) and then dried under vacuum at 50° C. The isolated solid was dissolved in hot 1:6 (v/v) isopropanol in hexanes. After cooling, the pure racemic 2-Acetamidoethyl 4-Chlorophenyl-(3-trifluoro methylphenoxy)-acetate formed as a crystalline solid. The solid was collected by filtration, the filter cake washed with 1:6 (v/v) isopropanol in hexanes and dried under vacuum at 50° C.

The racemic compound was dissolved in a solution of 20% isopropanol (IPA) and 80% hexane at 2.5% (wt/wt). The resulting solution was passed over a Whelk-O R,R Chiral Stationary Phase (CSP) in continuous fashion until >98% ee extract could be removed. The solvent was evaporated from the extract under reduced pressure to provide (−) 2-Acetamidoethyl 4-Chlorophenyl-(3-trifluoro methylphenoxy)-acetate. (The Simulated Moving Bed resolution was conducted by Universal Pharm Technologies LLC of 70 Flagship Drive, North Andover, Mass. 01845.)

EXAMPLE 8

Figure 6:
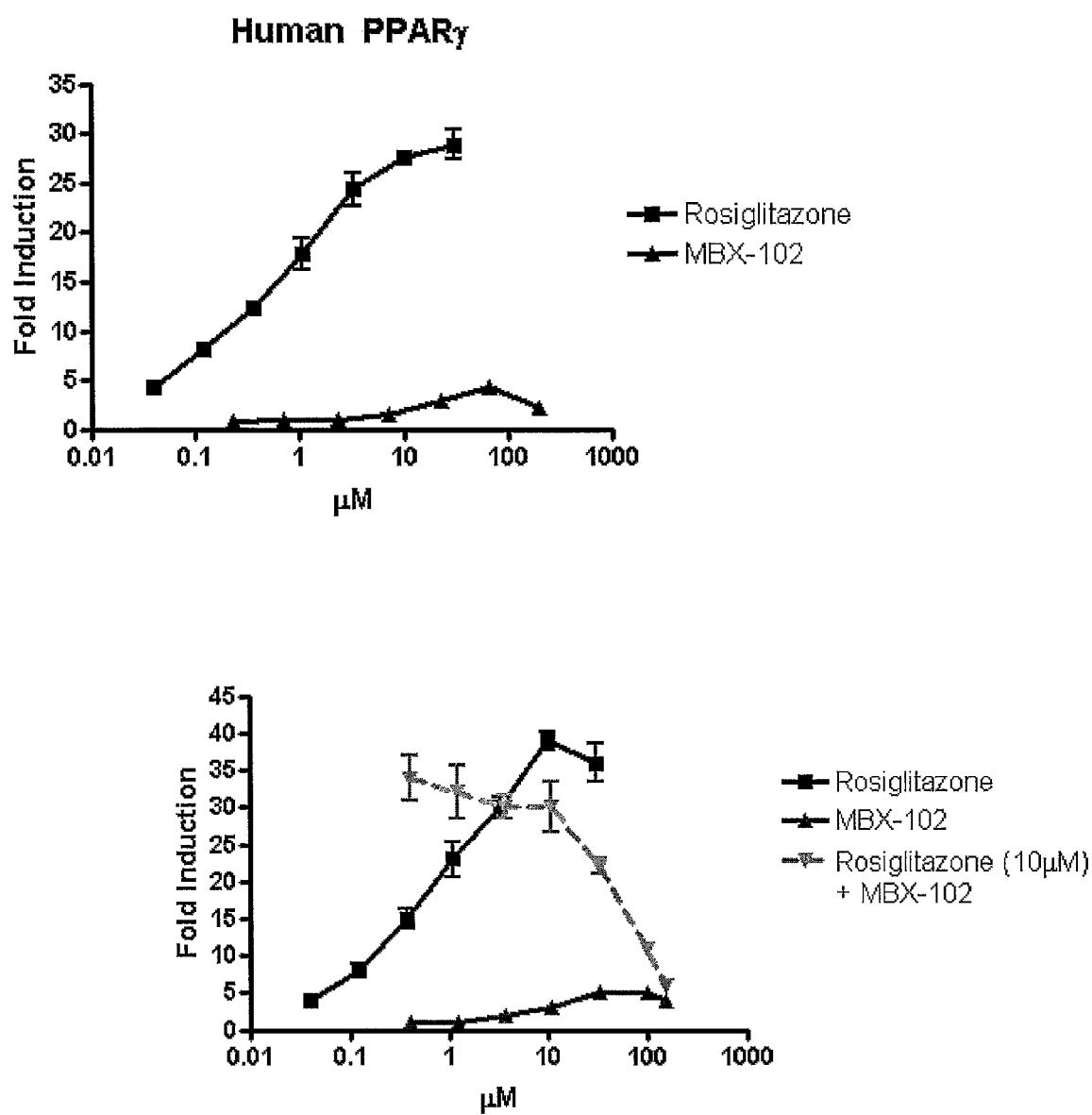
FIG. 6 illustrates the activity of (–) halofenic acid or of a (–) halofenate composition which is substantially free of the (+) isomer (MBX-102) and can be hydrolyzed to release (–)halofenic acid to act as a partial agonist of the PPARγ receptor.

Example 8 illustrates the partial agonism of the (−) isomer of either halofenic acid or halofenate on PPARγ (see, FIG. 6). The test compound displayed an ability to induce PPARγ expression a few fold while significantly antagonizing the agonist activity of rosiglitazone.

EXAMPLE 9

Example 9 presents the results of two randomized, double-blind, placebo-controlled, multi-centre studies on type 2 diabetics with inadequate control on insulin. The first study included 217 patients, randomized to dose groups of Placebo, 200 and 400 mg of a composition of (−) halofenate which was substantially free of the (+) isomer. The second study followed a substantially identical overall design, and included 100 patients randomized to dose groups of placebo and 600 mg of a composition of (−) halofenate which was substantially free of the (+) isomer. Both studies were about 4 months long, with a stabilization/run in period for 2 to 4 weeks and a 3 month treatment period. Endpoints included fasting plasma glucose (FPG), HbA1c, weight, and the incidence of edema.

As indicated below, the various experimental and placebo groups in the first study had similar demographics and base line characteristics.

|  | Pbo (n = 75) | 200 mg (n = 73) | 400 mg (n = 69) | Total (n = 217) | p-value |
|---|---|---|---|---|---|
| Age ± SD | 54.3 ± 10.9 | 53.1 ± 10.1 | 53.1 ± 10.4 | 53.5 ± 10.5 | 0.720 |
| Female (%) | 74.7 | 56.2 | 69.6 | 66.8 | 0.048 |
| Weight (kg ± SD) | 81.6 ± 18.0 | 80.0 ± 17.6 | 79.6 ± 19.8 | 80.4 ± 18.4 | 0.791 |
| BMI (kg/m2 ± SD) | 31.6 ± 4.6 | 30.3 ± 5.2 | 30.2 ± 5.5 | 30.7 ± 5.1 | 0.189 |

-continued

| | Pbo (n = 75) | 200 mg (n = 73) | 400 mg (n = 69) | Total (n = 217) | p-value |
|---|---|---|---|---|---|
| HbA1c (% ± SD) | 9.1 ± 1.03 | 9.0 ± 0.92 | 9.1 ± 1.05 | 9.1 ± 1.00 | 0.539 |
| % HbA1c >9% | 58.7 | 56.2 | 59.4 | 58.1 | NS |
| FPG (mg/dL ± SD) | 170.0 ± 50.2 | 173.3 ± 48.9 | 184.0 ± 58.1 | 174.1 ± 52.4 | NS |
| Duration of T2DM (yrs) | 13.9 ± 7.8 | 14.2 ± 7.6 | 13.2 ± 6.5 | 13.8 ± 7.3 | 0.695 |

As indicated below, the experimental and placebo groups in the second study also had similar demographics and base line characteristics.

| | | | | |
|---|---|---|---|---|
| Age ± SD | 53.1 ± 10.8 | 53.7 ± 10.6 | 53.4 ± 10.6 | 0.799 |
| Female (%) | 71.7 | 68.1 | 70.0 | 0.694 |
| Weight (kg ± SD) | 75.9 ± 16.7 | 79.2 ± 17.7 | 77.5 ± 17.2 | 0.330 |
| BMI (kg/m2 ± SD) | 29.9 ± 4.4 | 30.7 ± 4.9 | 30.3 ± 4.6 | 0.411 |
| HbA1c (% ± SD) | 9.6 ± 1.12 | 9.4 ± 1.14 | 9.5 ± 1.13 | 0.520 |
| % HbA1c >9% | 73.6 | 74.5 | 74.0 | NS |
| FPG (mg/dL ± SD) | 171.8 ± 58.3 | 160.3 ± 50.7 | 166.5 ± 54.9 | NS |
| Duration of T2DM (yrs) | 13.9 ± 8.1 | 13.6 ± 6.9 | 13.7 ± 7.5 | 0.851 |

As shown below, the experimental and placebo groups in the first study had similar dispositions over the course of the study.

| | Pbo | 200 mg | 400 mg | Total |
|---|---|---|---|---|
| Started Treatment | 75 | 74 | 69 | 217 |
| Discontinued Study Drug | 4 (5.3%) | 5 (6.8%) | 8 (11.6%) | 17 (7.8%) |
| Completed ≧67 Days | 71 (94.7%) | 68 (91.9%) | 61 (88.4%) | 200 (92.2%) |
| Discontinued due to AE | 2 (2.7%) | 3 (4.1%) | 3 (4.3%) | 8 (3.7%) |
| Discontinued for Other Reasons | 2 (2.7%) | 2 (2.7%) | 5 (7.2%) | 9 (4.1%) |

As shown below, the experimental and placebo groups in the second study also had similar dispositions over the course of the study.

| | | | |
|---|---|---|---|
| Started Treatment | 53 | 47 | 100 |
| Discontinued Study Drug | 4 (7.3%) | 1 (2.0%) | 5 (4.7%) |
| Completed ≧63 Days | 49 (89.1%) | 46 (90.2%) | 95 (89.6%) |
| Discontinued due to AE | 0 (0%) | 0 (0%) | 0 (0%) |
| Discontinued for Other Reasons | 4 (7.3%) | 1 (2.0%) | 5 (4.7%) |

Figure 7:
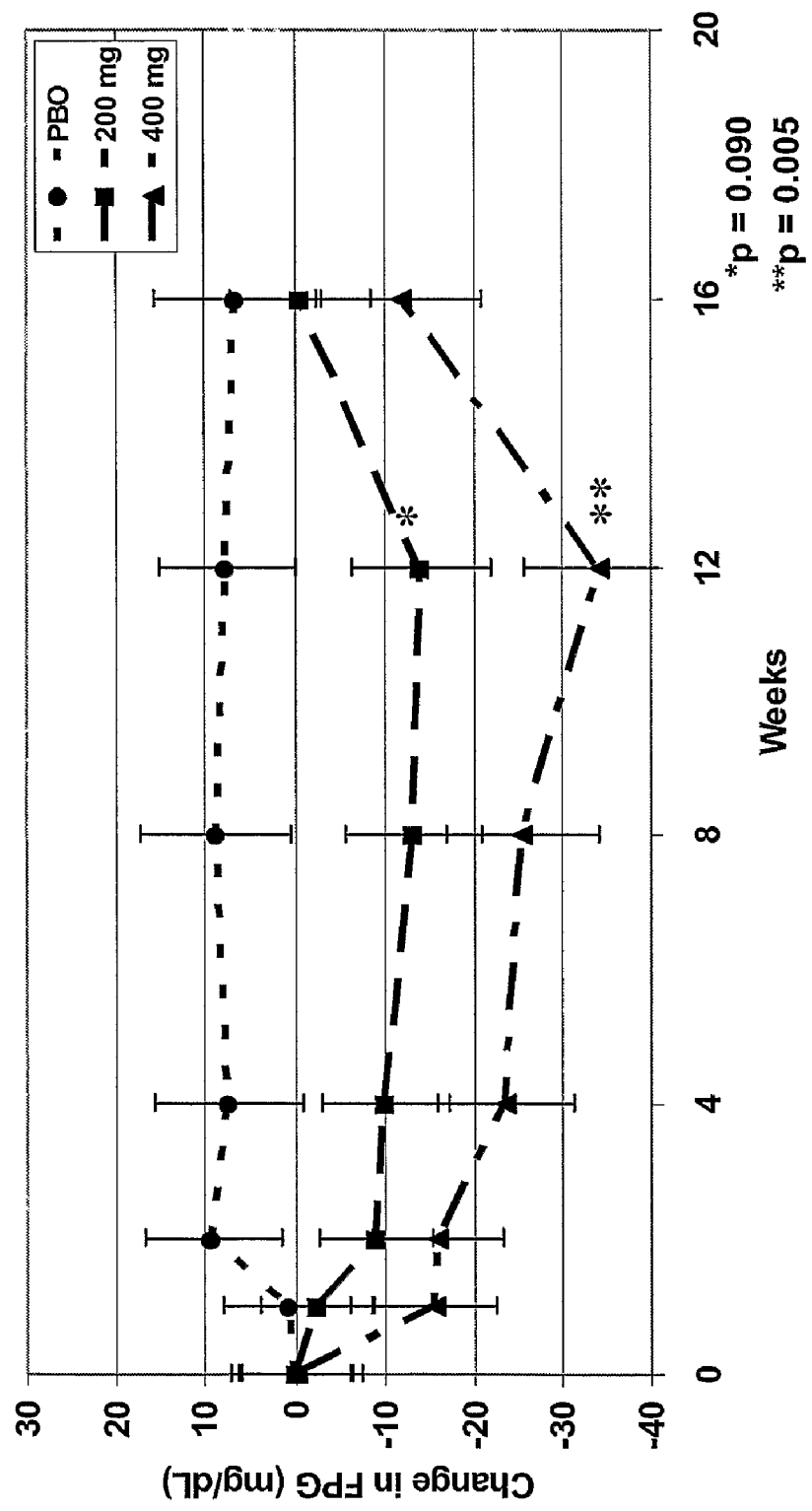
FIG. 7 shows the tested compound at doses of 200- and 400 mg lowered fasting plasma glucose levels in the experimental groups as compared to the placebo group.

FIG. 7 shows the tested compound at doses of 200- and 400 mg lowered fasting plasma glucose levels in the experimental groups as compared to the placebo group.

Figure 8:
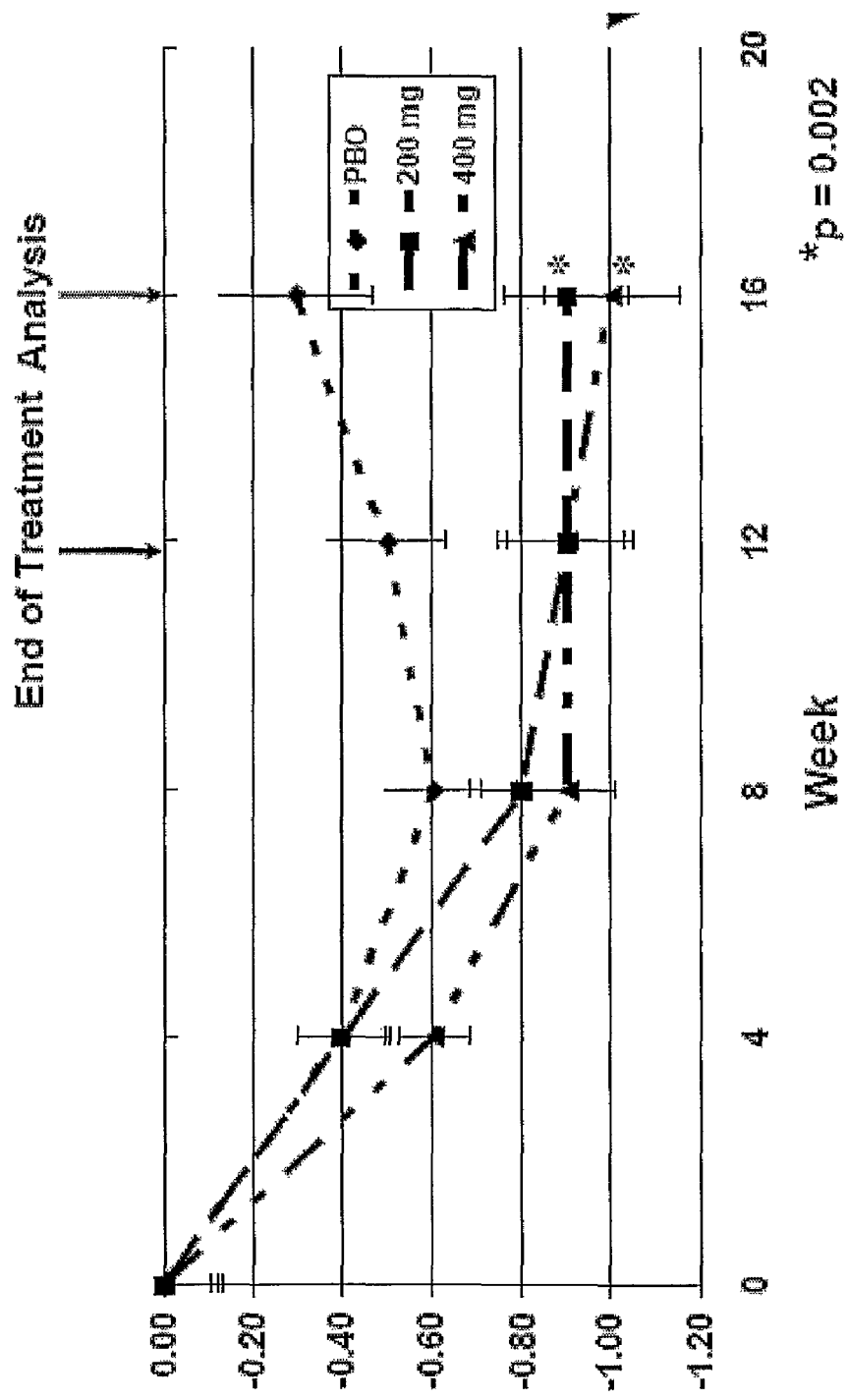
FIG. 8 shows the tested compound at doses of 200- and 400 mg lowered plasma glucose levels as judged by HbA1c levels in the experimental groups as compared to the placebo group.

FIG. 8 shows the tested compound at doses of 200- and 400 mg lowered plasma glucose levels as judged by HbA1c levels in the experimental groups as compared to the placebo group.

Figure 9:
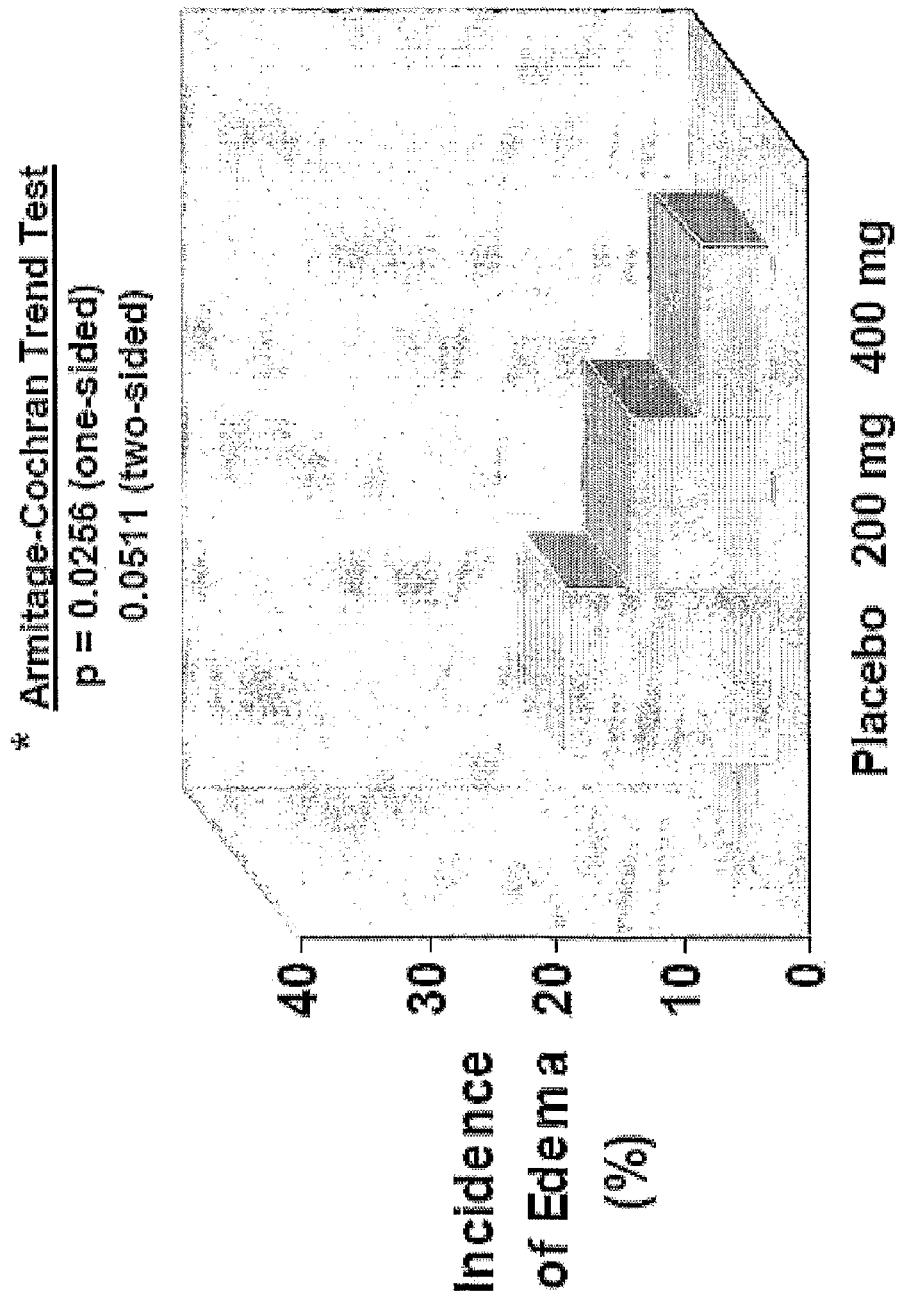
FIG. 9 shows that the test compound at doses of 200 and 400 mg prevented edema formation in the experimental group as compared to the placebo groups.

FIG. 9 shows that the test compound at doses of 200- and 400 mg prevented edema formation in the experimental group as compared to the placebo groups.

Figure 10:
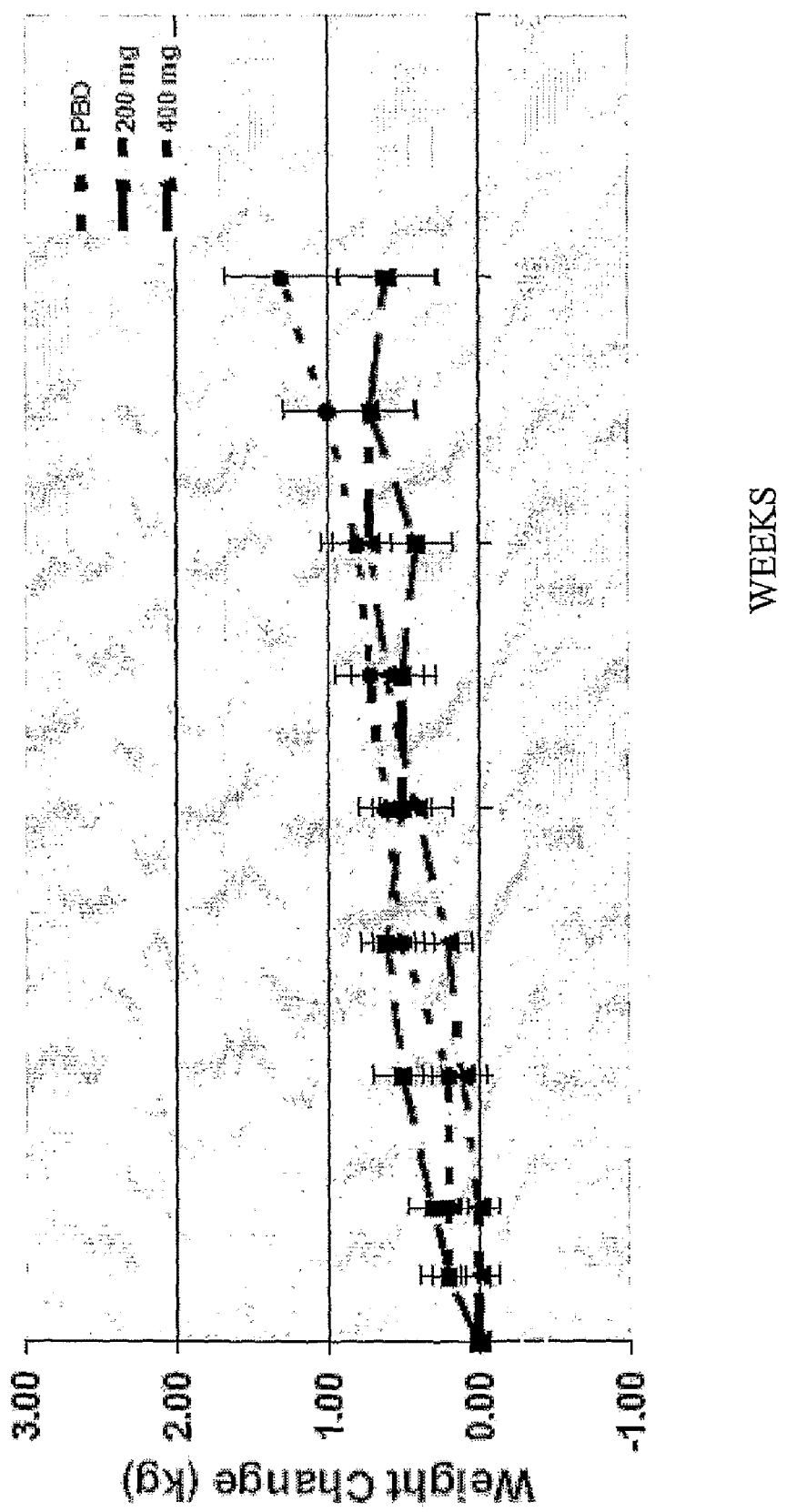
FIG. 10 shows that the test compound at doses of 200 and 400 mg did not induce weight gain in the experimental group as compared to the placebo group.

FIG. 10 shows that the test compound at doses of 200- and 400 mg did not induce weight gain in the experimental group as compared to the placebo group.

Figure 11:
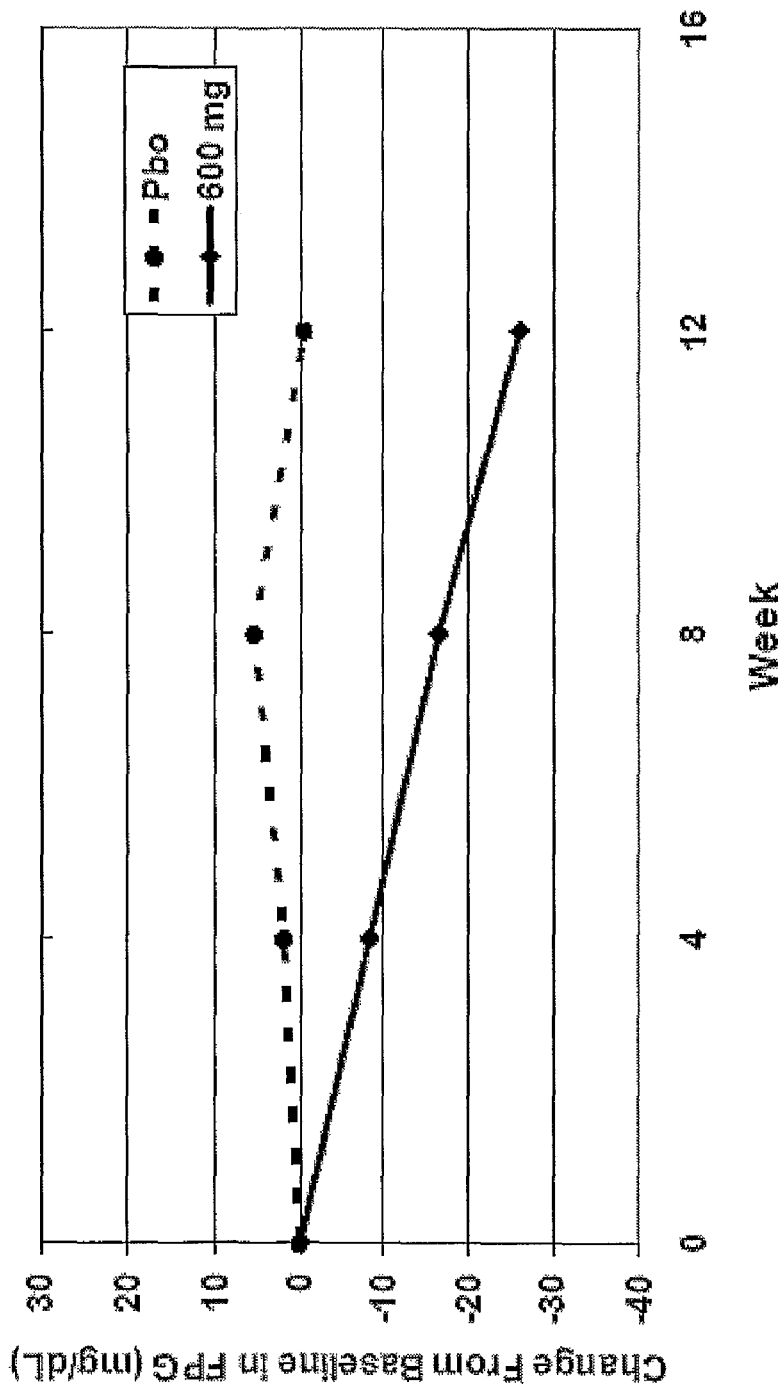
FIG. 11 shows the tested compound at a dose of 600 mg lowered fasting plasma glucose levels in the experimental group as compared to the placebo group.

FIG. 11 shows the tested compound at a dose of 600 mg lowered fasting plasma glucose levels in the experimental group as compared to the placebo group.

Figure 12:
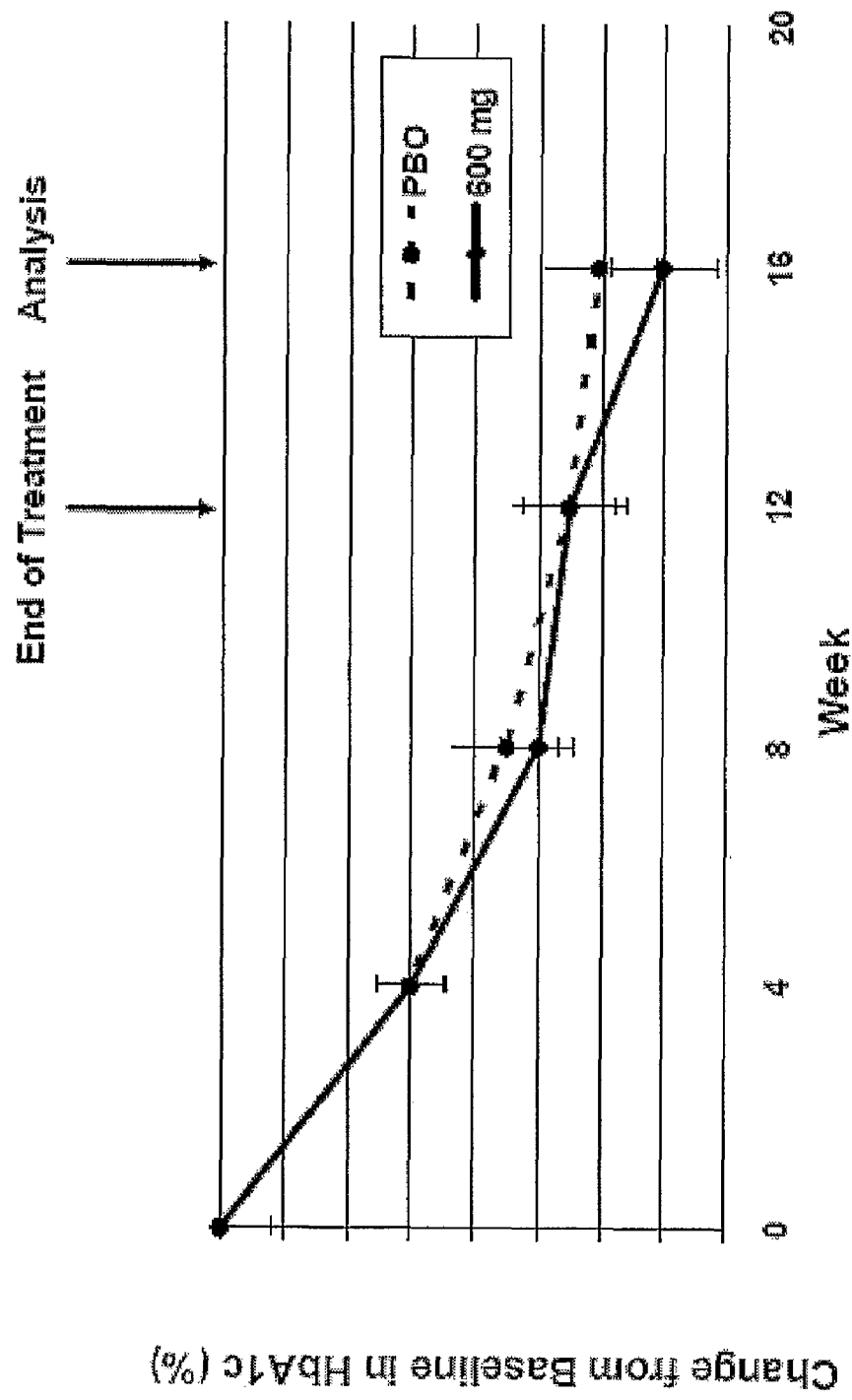
FIG. 12 shows the tested compound at a dose of 600 mg lowered plasma glucose levels as judged by HbA1c levels in the experimental group substantially from baseline, but that the placebo group demonstrated a comparable response. It was determined that two of the 10 clinical sites in this study (sites 60 & 70), who enrolled 43% of the patients, had substantially violated the protocol by placing all of their patients on a sliding scale of short-acting insulin in addition to their baseline doses of intermediate-acting insulin. This explains why HbA1c declined in the placebo group but FPG did not. The most statistically rigorous and conservative approach was to remove both of these violating sites from the analysis, which resulted in improved separation between treatment groups for both HbA1c and FPG, as shown below.

FIG. 12 shows the tested compound at a dose of 600 mg lowered plasma glucose levels as judged by HbA1c levels in the experimental group substantially from baseline, but that the placebo group demonstrated a comparable response. It was determined that two of the 10 clinical sites in this study (sites 60 & 70), who enrolled 43% of the patients, had substantially violated the protocol by placing all of their patients on a sliding scale of short-acting insulin in addition to their baseline doses of intermediate-acting insulin. This explains why HbA1c declined in the placebo group but FPG did not. The most statistically rigorous and conservative approach was to remove both of these violating sites from the analysis, which resulted in improved separation between treatment groups for both HbA1c and FPG, as shown below. Hence, these analyses address the impact of sites 60 and 70 on data presented in the priority provisional application.

Figure 13:
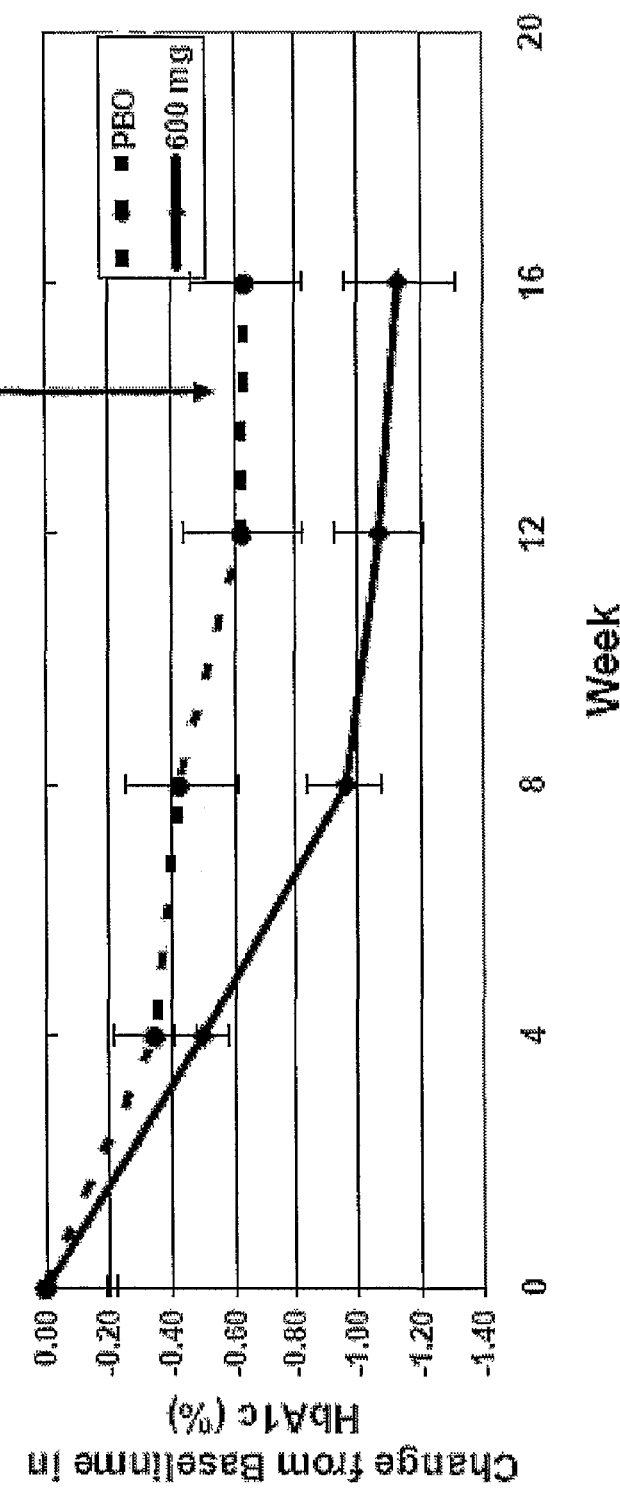
FIG. 13 shows the tested compound at a dose of 600 mg lowered plasma glucose levels as judged by HbA1c levels in the experimental group as compared to the placebo group in the analysis removing sites 60 and 70.

FIG. 13 shows the tested compound at a dose of 600 mg lowered plasma glucose levels as judged by HbA1c levels in the experimental group as compared to the placebo group in the analysis removing sites 60 and 70. Hence, these analyses address the impact of sites 60 and 70 on data presented in the priority provisional application.

Figure 14:
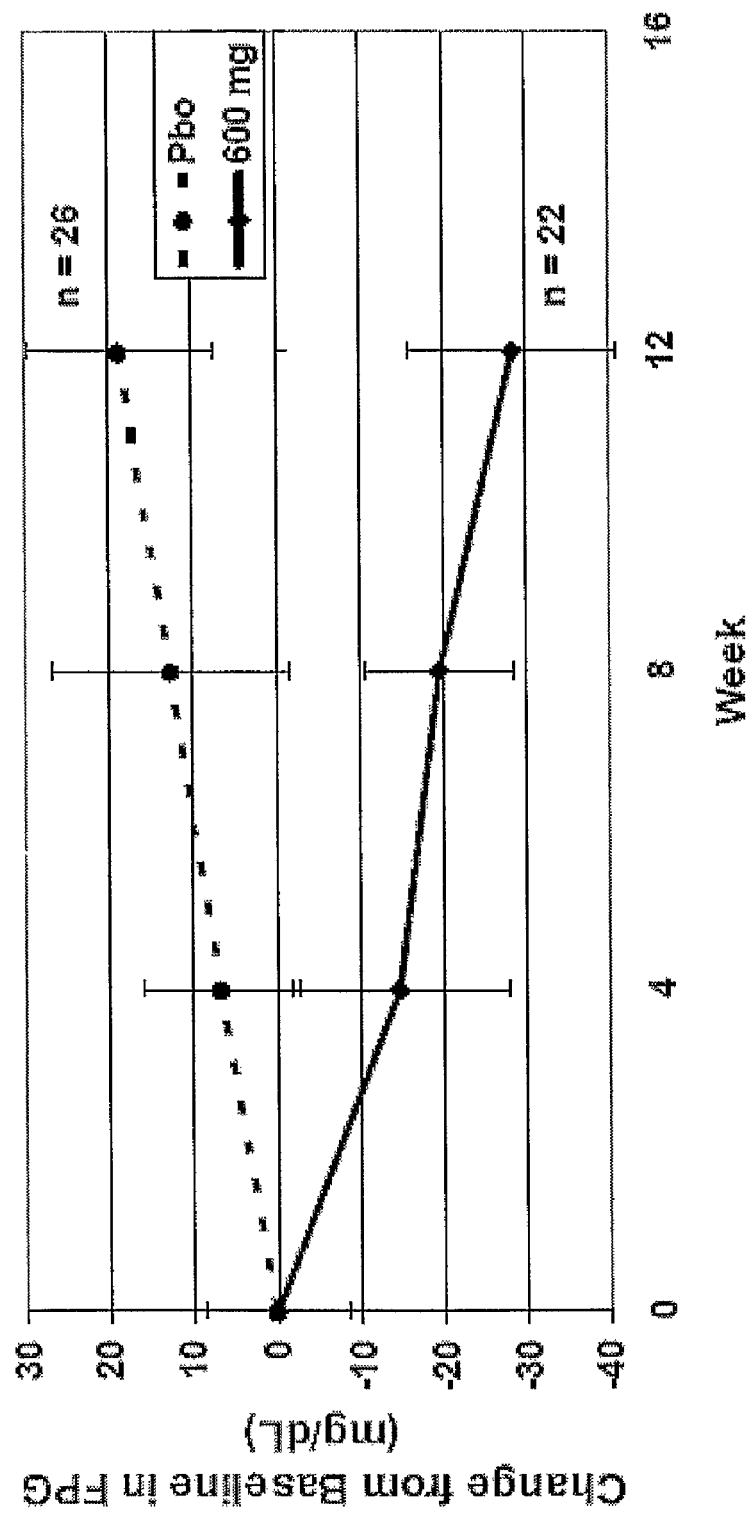
FIG. 14 shows that when sites 60 and 70 were removed, the tested compound at a dose of 600 mg lowered fasting plasma glucose levels in the experimental group as compared to the placebo group to an even greater extent than the 400 mg dose in the first study.

FIG. 14 shows that when sites 60 and 70 were removed, the tested compound at a dose of 600 mg lowered fasting plasma glucose levels in the experimental group as compared to the placebo group to an even greater extent than the 400 mg dose in the first study. Hence, these analyses address the impact of sites 60 and 70 on data presented in the priority provisional application.

Figure 15:
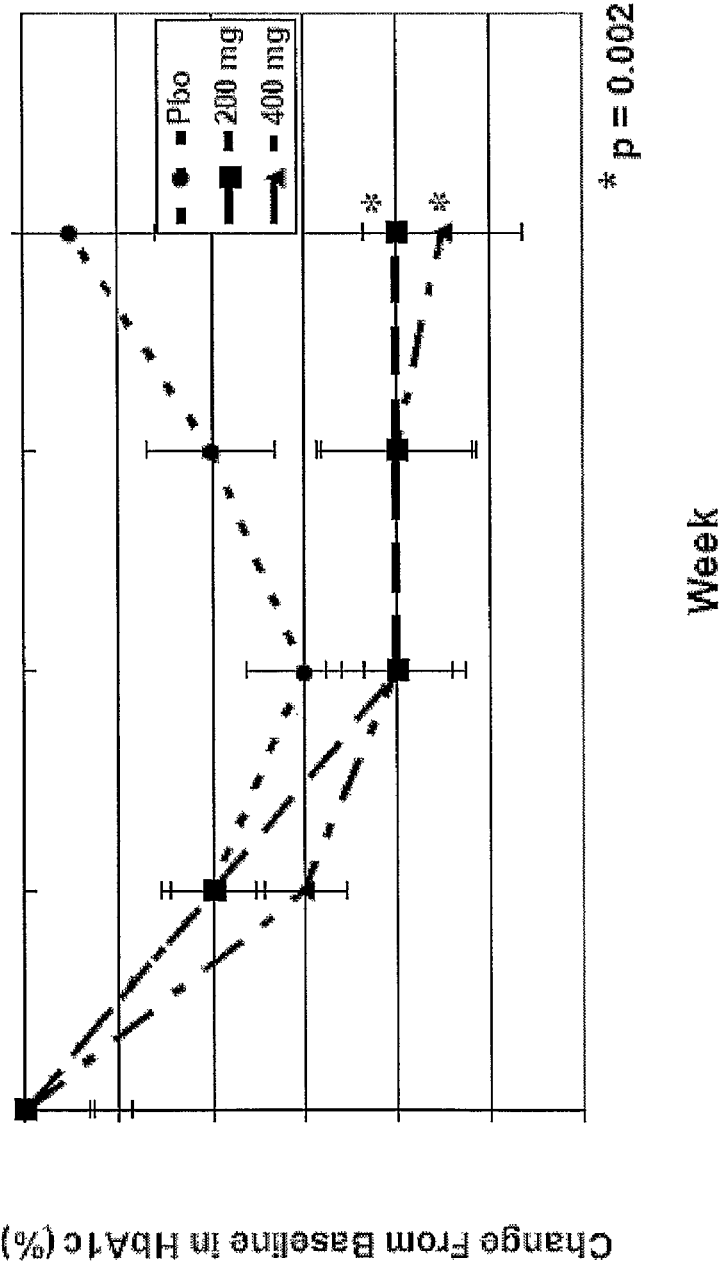
FIG. 15 shows that when sites 60 and 70 were removed from the analysis of the first study, the placebo response is attenuated and the tested compound at doses of 200- and 400 mg lowered plasma glucose levels as judged by HbA1c levels in the experimental groups as compared to the placebo group to an even greater extent than in the original analysis (FIG. 8).

FIG. 15 shows that when sites 60 and 70 were removed from the analysis of the first study, the placebo response is attenuated and the tested compound at doses of 200- and 400 mg lowered plasma glucose levels as judged by HbA1c levels in the experimental groups as compared to the placebo group to an even greater extent than in the original analysis (FIG. 8).

Figure 16:
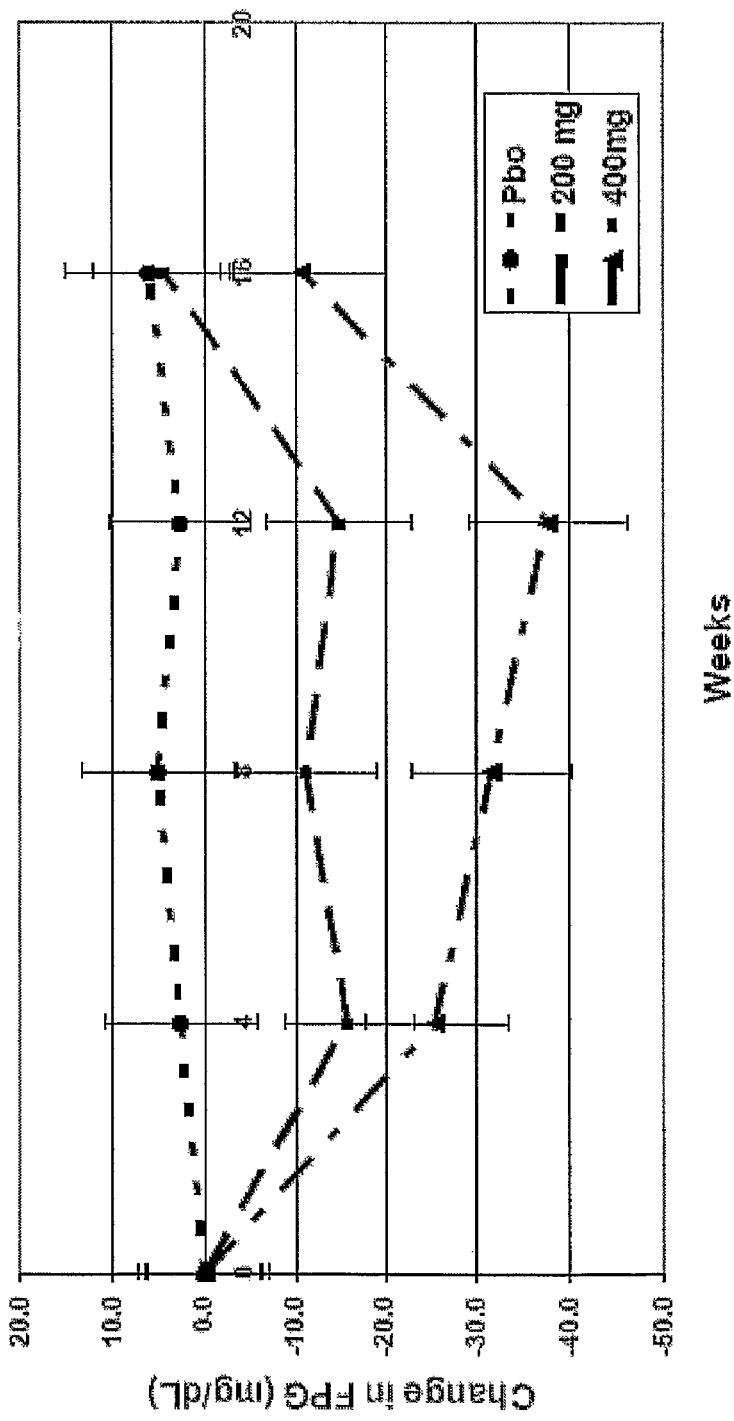
FIG. 16 shows that when sites 60 and 70 were removed from the analysis of the first study, the placebo response is attenuated and the tested compound at doses of 200- and 400 mg lowered fasting plasma glucose levels in the experimental groups as compared to the placebo group to an even greater extent than in the original analysis (FIG. 7).

FIG. 16 shows that when sites 60 and 70 were removed from the analysis of the first study, the placebo response is attenuated and the tested compound at doses of 200- and 400 mg lowered fasting plasma glucose levels in the experimental groups as compared to the placebo group to an even greater extent than in the original analysis (FIG. 7).

Figure 17:
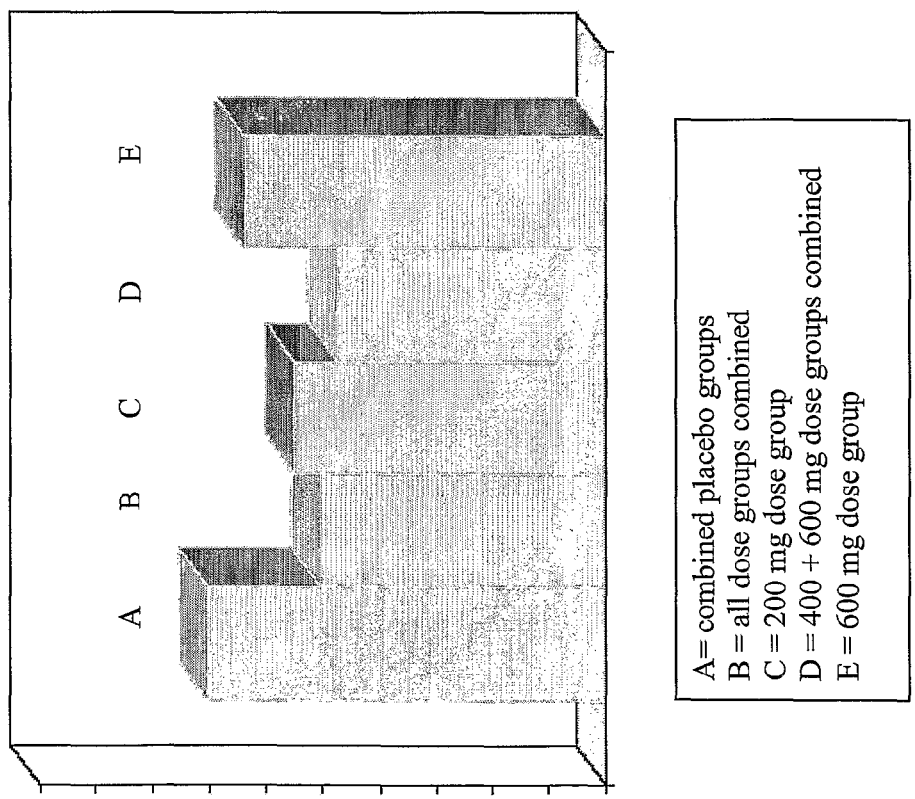
FIG. 17 shows that the test compound did not increase the incidence of edema formation across the dose range of 200 to 600 mg in the experimental groups as compared to the combined placebo groups from both studies. These results were not changed when sites 60 and 70 were removed.

FIG. 17 shows that the test compound did not increase the incidence of edema formation across the dose range of 200- to 600 mg in the experimental groups as compared to the combined placebo groups from both studies. These results were not changed when sites 60 and 70 were removed.

Figure 18:
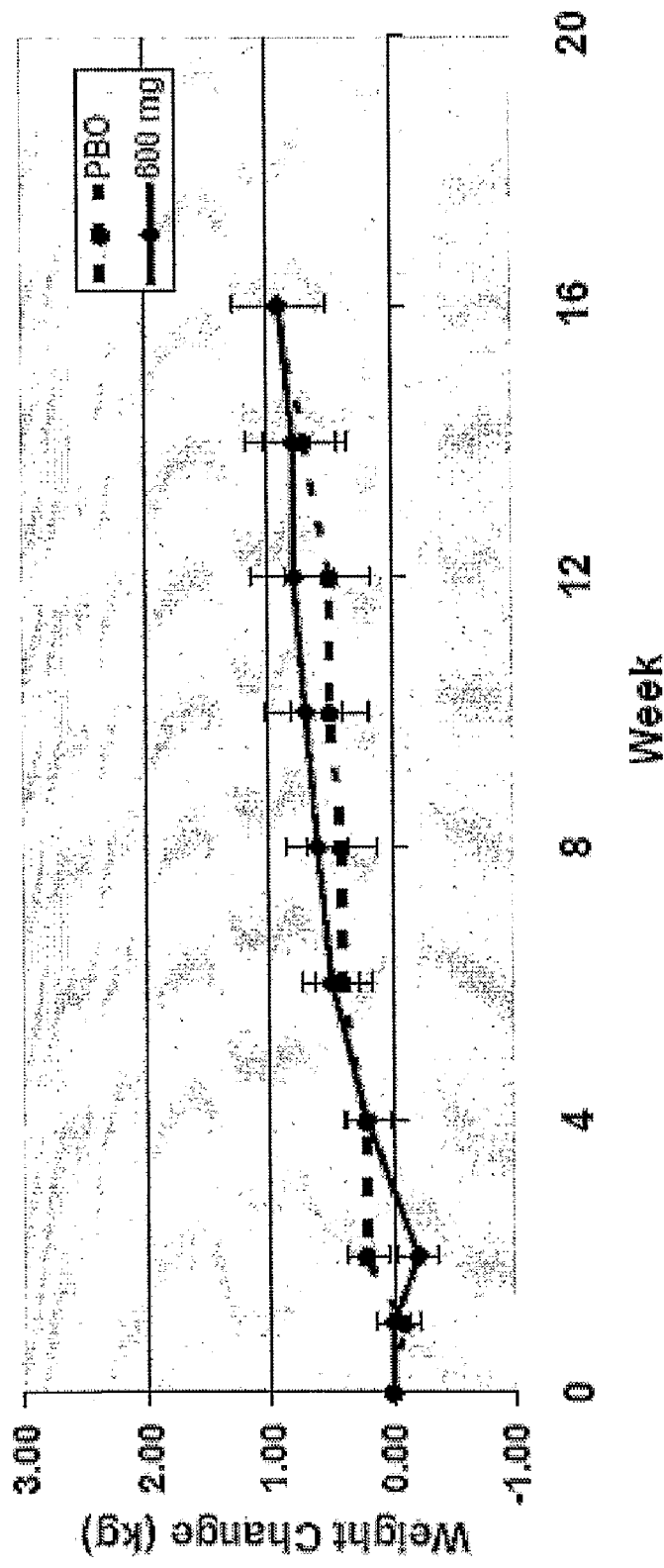
FIG. 18 shows that the test compound at a dose of 600 mg did not induce weight gain in the experimental group as compared to the placebo group. This result was not changed when sites 60 and 70 were removed.

FIG. 18 shows that the test compound at a dose of 600 mg did not induce weight gain in the experimental group as compared to the placebo group. This result was not changed when sites 60 and 70 were removed.

Additional analyses indicated that metaglisasen had a neutral effect on the HDL/cholesterol profile and was not associated with an excess of adverse effects on selected parameters with respect to the upper GI tract, the liver, the blood, or kidney (data not shown).

Figure 19:
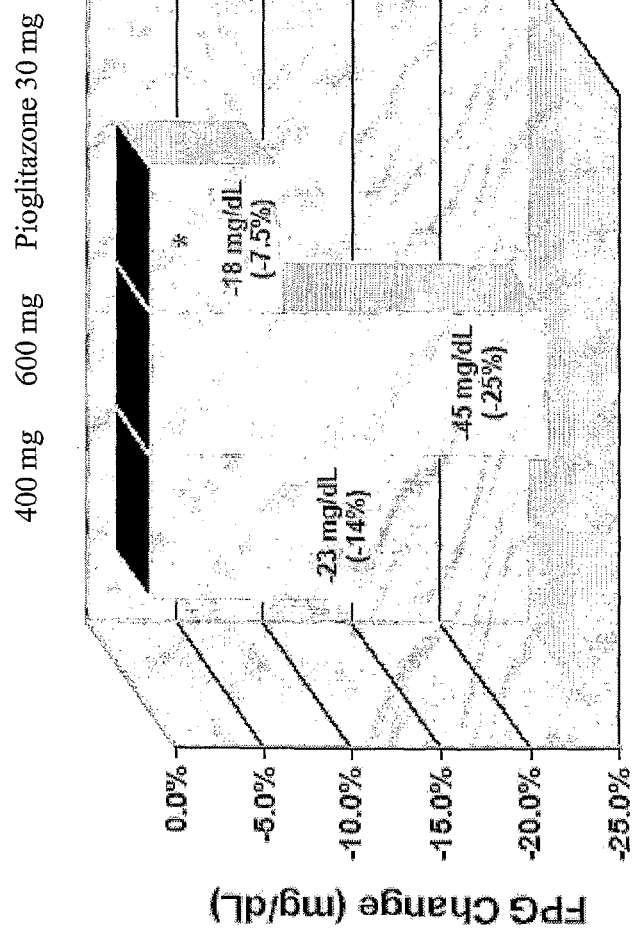
FIG. 19 shows the effect of the test compound Metaglidasen (a composition of (–) halofenate which is substantially free of the (+) isomer) after 14 days of treatment on fasting plasma glucose levels in human subjects also receiving glyburide. The results are contrasted to the work of others for pioglitazone (Actos) at 30 mg after 14 days of treatment.
Figure 20:
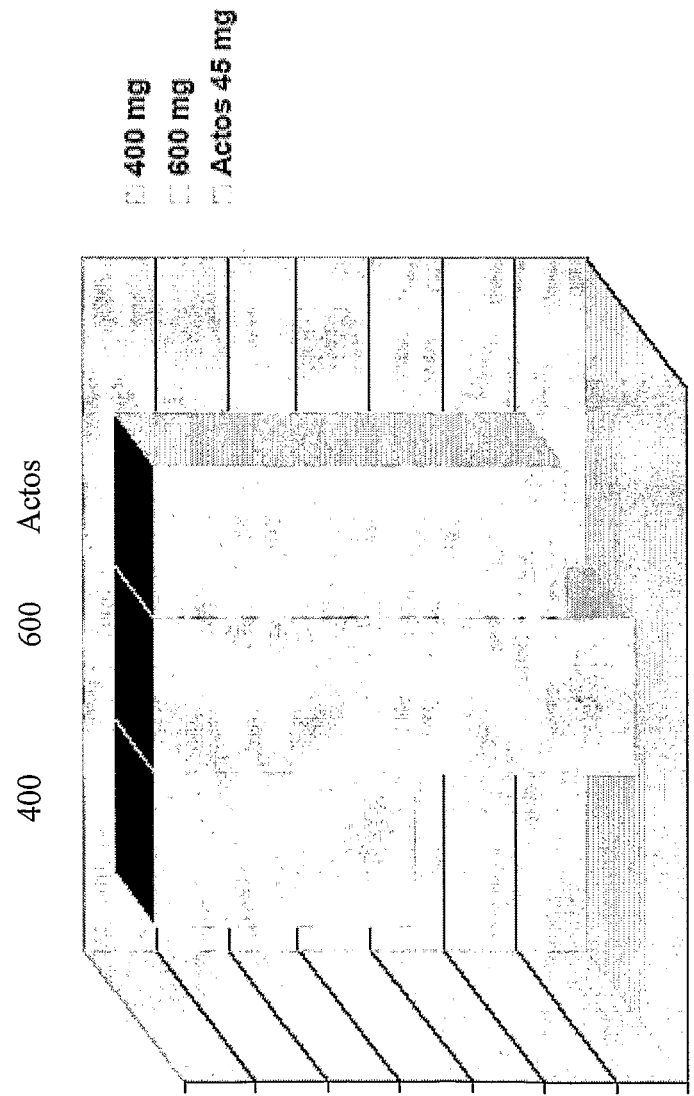
FIG. 20 shows the dose dependent effect of Metaglidasen on hsCRP in human patients after 14 days of treatment. The data for pioglitazone (Actos) is taken from Goldberg R B et al., *Diabetes Care* 28(7):1547-54 (2005), which is incorporated herein by reference.

Other analyses indicated that metaglidasen could substantially lower blood glucose levels in patients also receiving glyburide (see FIG. 19). In addition, metaglidasen could also lower hsCRP levels (see FIG. 20). Additional results showed that metaglidasen lowered serum triglycerides substantially (data not shown).

The results of separate animal studies (e.g., monkeys and rats) has found that metaglidasen did not cause increases at therapeutically relevant doses in heart weight or fluid accumulation (data not shown).

EXAMPLE 10

This Example provides structures of additional prodrug compounds, along with characterization data and reference to the methods employed for preparation the source of starting materials. Methods of making such compounds are known to one of ordinary skill in the art by methods s set forth in PCT Patent Application Publication No.: WO/2002/044113.

| Illustrative compounds, source of reagents and coupling methods | | |
|---|---|---|
| Compound and number | Reagent and Source Reference: | Structural elucidation |
| 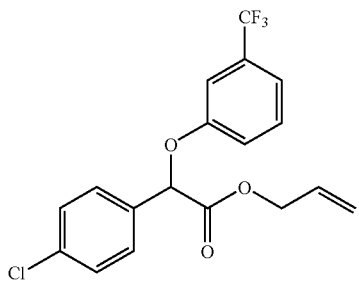<br>19.1 | 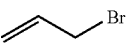<br>Aldrich | $[\alpha]^{24}$D- 55.03 (c 5.23, CHCl$_3$)<br>$^1$HNMR (400 MHz, CHCl$_3$): δ7.0-7.5 (8H, m), 5.8 (1H, m), 5.6 (1H, s), 5.2 (2H, dd), 4.6 (2H, m).<br>LCMS, 369, 99%<br>98% ee |
| 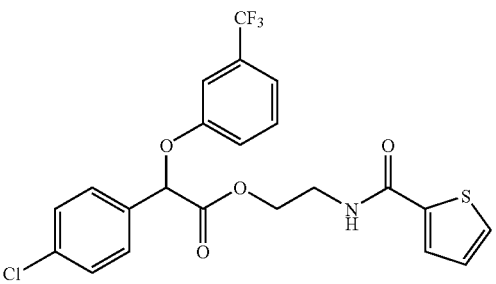<br>19.2 | 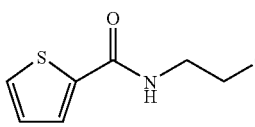<br>U.S. Pat. No. 5,506,224 | $[\alpha]^{24}$D- 27.16 (c 6.99, CHCl$_3$)<br>$^1$HNMR (400 MHz, CHCl$_3$): δ7.0-7.5 (11H, m), 5.9 (1H, m), 4.3 (2H, m), 3.6 (2H, m).<br>LCMS, 482, 99%<br>98% ee |
| 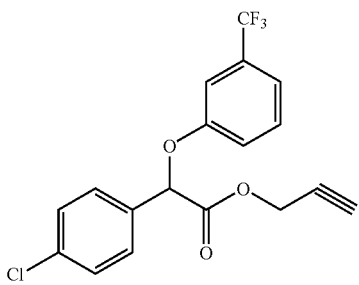<br>19.3 | 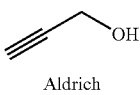<br>Aldrich | $[\alpha]^{24}$D- 44.46 (c 5.90, CHCl$_3$)<br>$^1$HNMR (400 MHz, CHCl$_3$): δ7.0-7.5 (13H, m), 5.6 (1H, s), 4.7 (2H, dd), 2.4 (1H, s).<br>LCMS, 368, 99%<br>98% ee |

-continued

Illustrative compounds, source of reagents and coupling methods

| Compound and number | Reagent and Source Reference: | Structural elucidation |
|---|---|---|
| 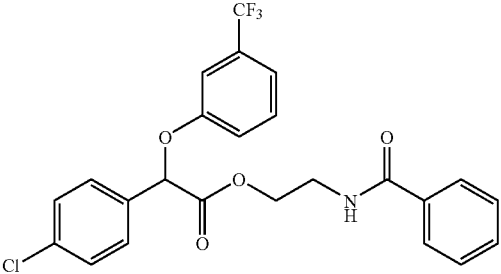 19.4 | 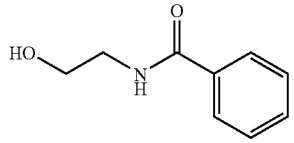 Aldrich | $[\alpha]^{24}$D- 35.40 (c 12.6, CHCl$_3$)<br>$^1$HNMR (400 MHz, CHCl$_3$): δ7.0-7.5 (13H, m), 6.0 (1H, m), 5.6 (1H, s), 4.3 (2H, m), 3.6 (2H, m).<br>LCMS, 477, 99%<br>97.4% ee |
| 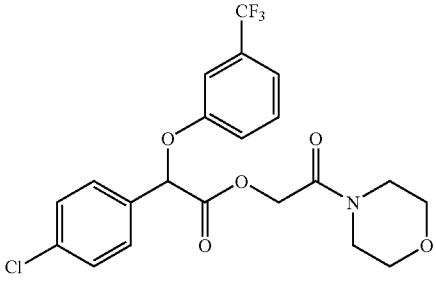 19.5 | 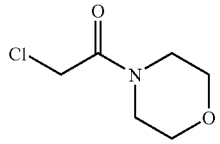 Maybridge | $[\alpha]^{24}$D- 57.39 (c 10.3, CHCl$_3$)<br>$^1$HNMR (400 MHz, CHCl$_3$): δ7.1-7.5 (8H, m), 5.7 (1H, s), 4.9 (1H, d), 4.6 (1H, d), 3.6 (8H, m).<br>LCMS, 457, 99%<br>97.4% ee |
| 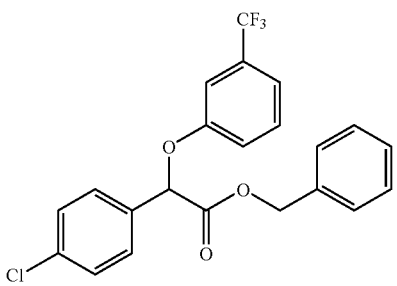 19.6 | 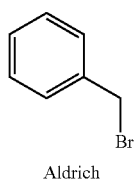 Aldrich | $[\alpha]^{24}$D- 35.38 (c 7.36, CHCl$_3$)<br>$^1$HNMR (400 MHz, CHCl$_3$): δ7.0-7.5 (13H, m), 5.6 (1H, s), 5.1 (2H, dd).<br>LCMS, 421, 99%<br>98% ee |
| 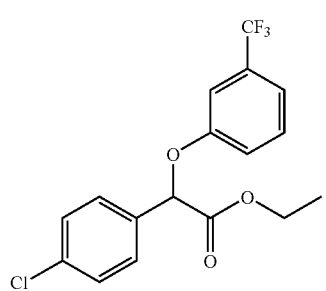 19.7 | 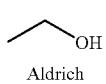 Aldrich | $[\alpha]^{24}$D- 56.34 (c 5.32, CHCl$_3$)<br>$^1$HNMR (400 MHz, CHCl$_3$): δ7.0-7.5 (8H, m), 5.6 (1H, s), 4.2 (2H, m), 1.1 (3H, t).<br>LCMS, 358, 98%<br>98% ee |

-continued

Illustrative compounds, source of reagents and coupling methods

| Compound and number | Reagent and Source Reference: | Structural elucidation |
|---|---|---|
| 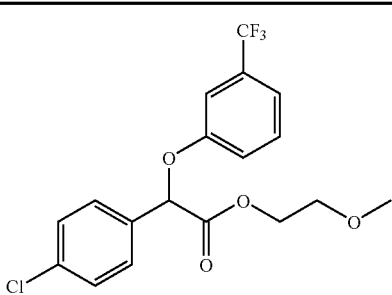<br>19.8 | 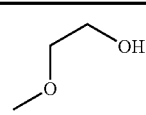<br>Aldrich | $[\alpha]^{24}$D- 54.13 (c 8.40, CHCl$_3$)<br>$^1$HNMR (400 MHz, CHCl$_3$): δ7.0-7.5 (8H, m), 5.6 (1H, s), 4.4 (1H, m), 4.2 (1H, m), 3.5 (2H, m), 3.3 (3H, s).<br>LCMS, 445, 97%<br>97.7% ee |
| 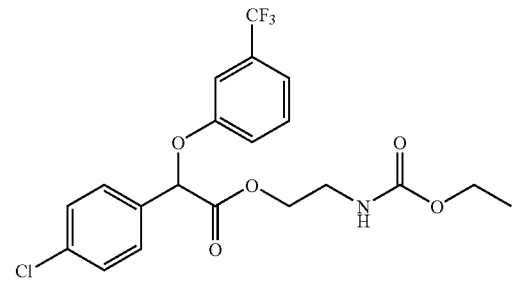<br>19.9 | 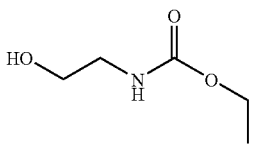<br>U.S. Pat. No. 5,506,224 | $[\alpha]^{24}$D- 43.30 (c 6.61, CHCl$_3$)<br>$^1$HNMR (400 MHz, CHCl$_3$): δ7.0-7.5 (8H, m), 5.6 (1H, s), 4.5 (1H, m), 4.2 (2H, m), 4.0 (2H, m), 3.3 (2H, m), 1.1 (3H, m).<br>LCMS, 445, 97%<br>96.8% ee |
| 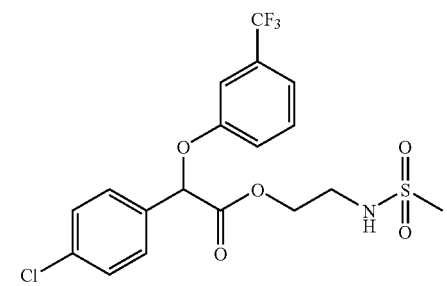<br>19.10 | 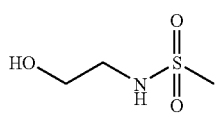<br>U.S. Pat. No. 5,506,224 | $[\alpha]^{24}$D- 42.33 (c 7.30, CHCl$_3$)<br>$^1$HNMR (400 MHz, CHCl$_3$): δ7.0-7.5 (8H, m), 5.6 (1H, s), 4.3 (2H, m), 4.1 (1H, m), 3.3 (2H, m), 2.8 (3H, s).<br>LCMS, 451, 97%<br>96.5% ee |
| 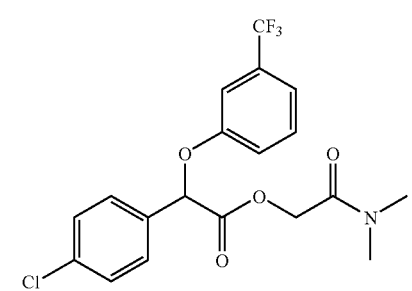<br>19.11 | 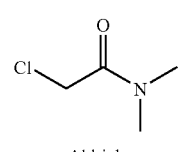<br>Aldrich | $[\alpha]^{24}$D- 57.87 (c 2.57, CHCl$_3$)<br>$^1$HNMR (400 MHz, CHCl$_3$): δ7.0-7.5 (8H, m), 5.6 (1H, s), 4.9 (1H, d), 4.6 (1H, d), 2.9 (3H, s), 2.8 (3H, s).<br>LCMS, 415, 98%<br>97.1% ee |

-continued

Illustrative compounds, source of reagents and coupling methods

| Compound and number | Reagent and Source Reference: | Structural elucidation |
|---|---|---|
| 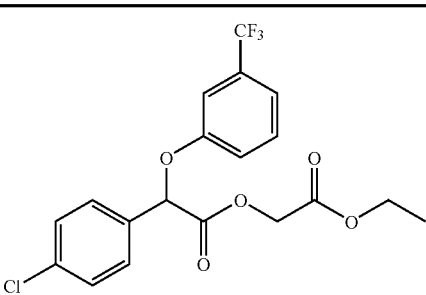<br>19.12 | 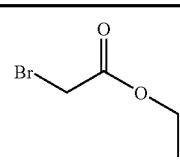<br>Aldrich | $[\alpha]^{24}$D- 62.27 (c 5.35, CHCl$_3$)<br>$^1$HNMR (400 MHz, CHCl$_3$): δ7.0-7.5 (8H, m), 5.6 (1H, s), 4.2 (2H, m), 1.1 (3H, t).<br>LCMS, 416, 99%<br>98% ee |
| 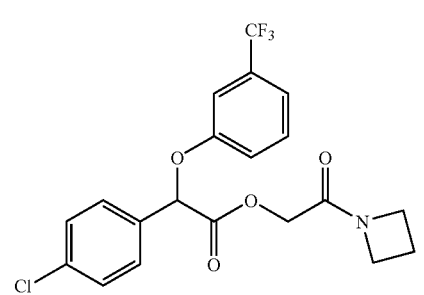<br>19.13 | 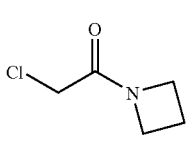<br>U.S. Pat. No. 3,998,808 | $[\alpha]^{24}$D- 49.85 (c 11.3, CHCl$_3$)<br>$^1$HNMR (400 MHz, CHCl$_3$): δ7.0-7.5 (8H, m), 5.7 (1H, s), 4.6 (2H, d), 4.4 (2H, d), 4.0 (4H, m), 2.3 (2H, m).<br>LCMS, 427, 96%<br>96.1% ee |
| 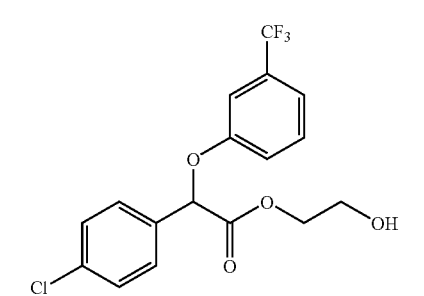<br>19.14 | 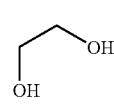<br>Aldrich | $[\alpha]^{24}$D- 51.17 (c 6.76, CHCl$_3$)<br>$^1$HNMR (400 MHz, CHCl$_3$): δ7.0-7.5 (8H, m), 5.6 (1H, s), 5.3 (1H, s), 4.3 (2H, m), 3.7 (2H, m).<br>LCMS, 374, 98%<br>95.9% ee |
| 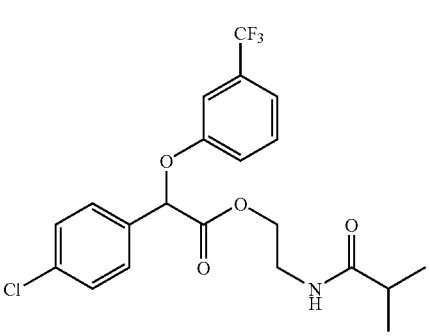<br>19.15 | 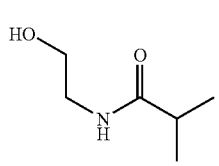<br>U.S. Pat. No. 5,506,224 | $[\alpha]^{24}$D- 40.97 (c 8.18, CHCl$_3$)<br>$^1$HNMR (400 MHz, CHCl$_3$): δ7.0-7.5 (8H, m), 5.6 (1H, s), 5.3 (1H, s), 4.1 (2H, m), 3.4 (2H, m), 2.1 (1H, m), 1.0 (3H, d)<br>LCMS, 443, 99%<br>97.1% ee |

-continued

Illustrative compounds, source of reagents and coupling methods

| Compound and number | Reagent and Source Reference: | Structural elucidation |
|---|---|---|
| 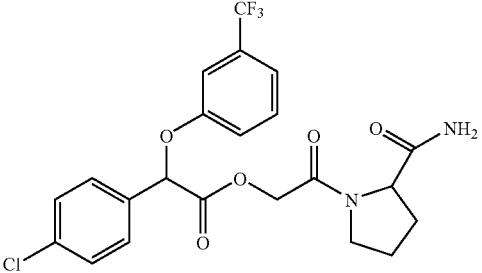<br>19.16 | 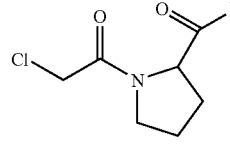<br>Synthesis (1991) 571 | $[\alpha]^{24}$D- 111.2 (c 10.8, CHCl$_3$)<br>$^1$HNMR (400 MHz, CHCl$_3$): $\delta$7.0-7.5 (8H, m), 6.7 (1H, m) 5.6 (1H, s), 5.3 (1H, m), 4.9 (1H, d), 4.4 (1H, m), 4.4 (1H, d), 3.4 (1H, m), 3.3 (1H, m), 2.4 (1H, m), 2.2 (1H, m), 2.0 (1H, m), 1.8 (1H, m).<br>LCMS, 484, 99%<br>96% ee |
| 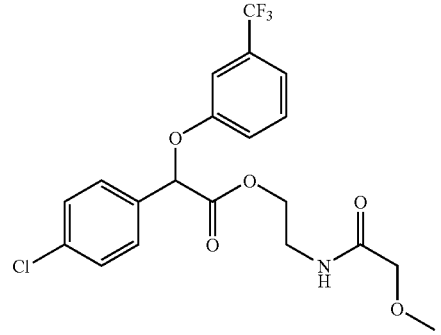<br>19.17 | 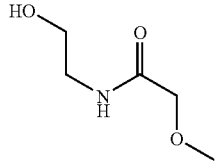<br>US Pat 5,506,224 | $[\alpha]^{24}$D- 36.72 (c 8.90, CHCl$_3$)<br>$^1$HNMR (400 MHz, CHCl$_3$): $\delta$6.8-7.5 (8H, m), 6.5 (1H, m), 5.6 (1H, s), 4.3 (2H, m), 3.8 (2H, s), 3.5 (2H, m), 3.4 (3H, s).<br>LCMS, 445, 99%<br>98% ee |
| 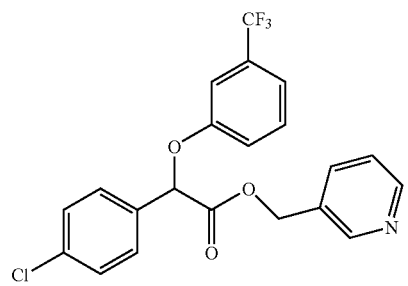<br>19.18 | 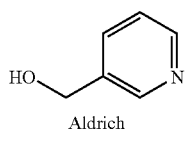<br>Aldrich | $[\alpha]^{24}$D-21.23 (c 13.2, CHCl$_3$)<br>$^1$HNMR (400 MHz, CHCl$_3$):<br>$\delta$ 8.6 (1H, σ), 7.8 (1H, δ), 7.0-7.6 (10H, m), 5.6 (1H, s), 5.2 (2H, s).<br>LCMS, 421, 99%<br>97% ee |
| 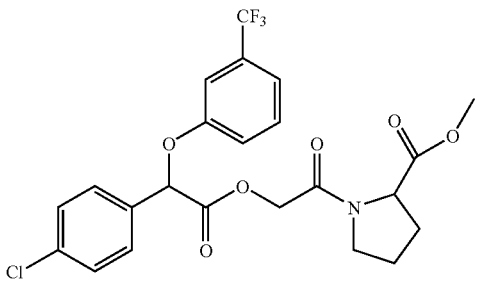<br>19.19 | 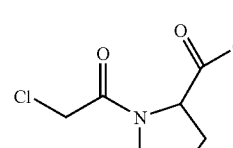<br>J. Med. Chem (1997) 3594 | $[\alpha]^{24}$D- 108.3 (c 9.36, CHCl$_3$)<br>$^1$HNMR (400 MHz, CHCl$_3$): $\delta$7.0-7.5 (8H, m), 5.8 (1H, s), 5.0 (2H, d), 4.5 (1H, m), 4.5 (2H, d), 3.7 (3H, s), 3.4-3.7 (2H, m), 1.8-2.3 (4H, m).<br>LCMS, 499, 99%<br>98.3% ee |

-continued

Illustrative compounds, source of reagents and coupling methods

| Compound and number | Reagent and Source Reference: | Structural elucidation |
|---|---|---|
| 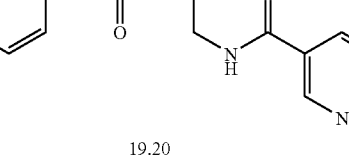<br>19.20 | <br>U.S. Pat. No. 5,506,224 | $[\alpha]^{24}D$- 32.05 (c 6.00, CHCl$_3$)<br>$^1$HNMR (400 MHz, CHCl$_3$):<br>δ 9.4 (1H, br. s), 8.7 (1H, br. s), 8.4 (1H, br. s), 7.7 (1H, br.s), 7.0-7.5 (8H, m), 5.8 (1H, s), 4.4 (2H, m), 3.7 (2H, m).<br>LCMS, 479, 99%<br>97.6% ee |
| 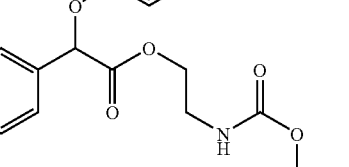<br>19.21 | 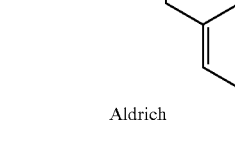<br>Aldrich | $[\alpha]^{24}D$- 28.19 (c 14.3, CHCl$_3$)<br>$^1$HNMR (400 MHz, CHCl$_3$): δ7.0-7.5 (13H, m), 5.6 (1H, s), 5.1 (2H, s), 4.6 (1H, m), 4.2 (2H, m), 3.4 (2H, m).<br>LCMS, 507, 99%<br>98% ee |
| 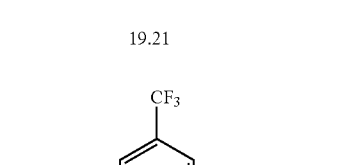<br>19.22 | 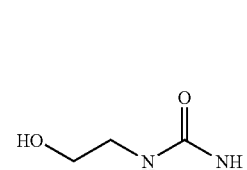<br>Chem. Soc. Rev (1975) 231 | $[\alpha]^{24}D$- 39.80 (c 5.90, CHCl$_3$)<br>$^1$HNMR (400 MHz, CHCl$_3$): δ7.0-7.5 (8H, m), 5.6 (1H, s), 4.2 (2H, m), 4.0 (1H, m), 3.4 (2H, m), 3.0 (2H, m), 1.0 (3H, t).<br>LCMS, 444, 99%<br>98% ee |
| 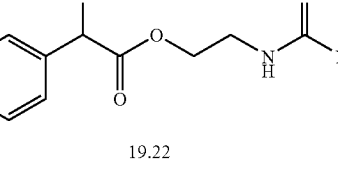<br>19.23 | 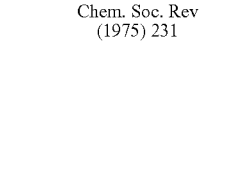<br>Aldrich | $[\alpha]^{24}D$- 44.75 (c 7.60, CHCl$_3$)<br>$^1$HNMR (400 MHz, CHCl$_3$): δ7.0-7.5 (8H, m), 5.6 (1H, s), 4.1-4.4 (4H, m), 1.9 (3H, s).<br>LCMS, 416, 99%<br>98.36% ee |

-continued

Illustrative compounds, source of reagents and coupling methods

| Compound and number | Reagent and Source Reference: | Structural elucidation |
|---|---|---|
| 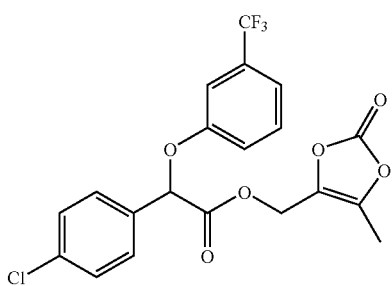<br>19.24 | 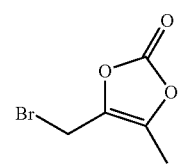<br>U.S. Pat. No. 5,466,811 | [α]$^{24}$D- 35.63 (c 5.30, CHCl$_3$)<br>$^1$HNMR (400 MHz, CHCl$_3$): δ7.0-7.5 (8H, m), 5.6 (1H, s), 4.9 (2H, dd), 2.1 (3H, s).<br>LCMS, 442, 99%<br>98.3% ee |
| 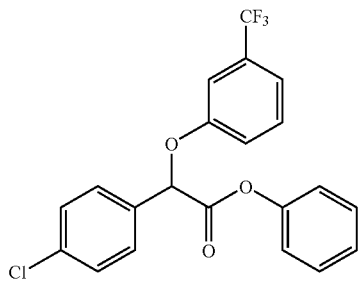<br>19.25 | 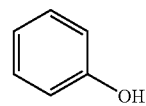<br>Aldrich | [α]$^{24}$D- 38.42 (c 8.78, CHCl$_3$)<br>$^1$HNMR (400 MHz, CHCl$_3$): δ6.9-7.7 (13H, m), 5.8 (1H, s).<br>LCMS, 406, 99%<br>99% ee |
| 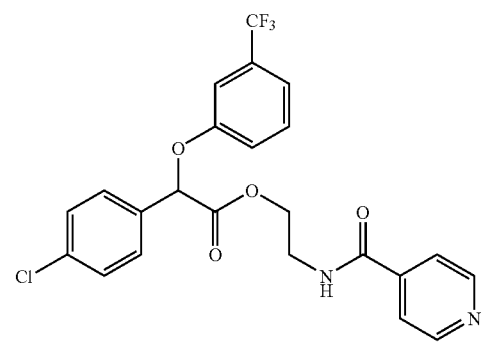<br>19.26 | 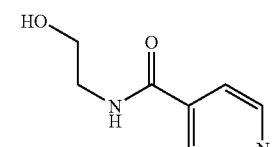<br>Aldrich | [α]$^{24}$D- 28.50 (c 8.40, CHCl$_3$)<br>$^1$HNMR (400 MHz, CHCl$_3$):<br>δ 8.8 (2H, d), 7.5 (2H, d), 7.0-7.4 (8H, m), 6.3 (1H, s), 5.6 (1H, s), 4.4 (2H, br. s), 3.8 (2H, br. s).<br>LCMS, 478, 99%<br>97% ee |
| 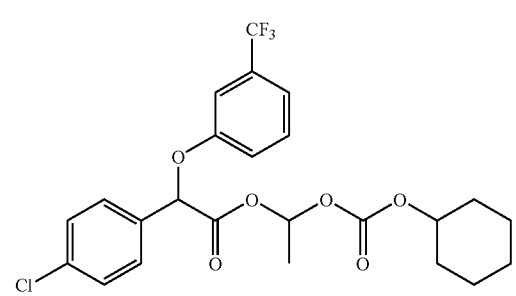<br>19.27 | 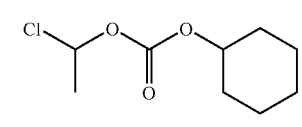<br>Syn. (1986) 627 | [α]$^{24}$D- 31.48 (c 5.00, CHCl$_3$)<br>$^1$HNMR (400 MHz, CHCl$_3$): δ7.0-7.5 (8H, m), 6.8 (1H, m), 5.6 (1H, s), 4.5 (1H, m), 1.2-2.0 (13H, m).<br>LCMS, 500, 99%<br>99% ee |

| Compound and number | Reagent and Source Reference: | Structural elucidation |
|---|---|---|
| 19.28 | Sigma (glycine) | $[\alpha]^{24}$D- 29.52 (c 2.04, CHCl$_3$)<br>$^1$HNMR (400 MHz, CHCl$_3$): δ7.0-7.5 (8H, m), 5.6 (1H, s), 4.2-4.5 (4H, m), 3.7 (2H, m).<br>LCMS, 431, 99%<br>96.4% ee |
| 19.29 | Sigma (N-Boc prolinol) | $[\alpha]^{24}$D- 20.83 (c 5.42, CHCl$_3$)<br>$^1$HNMR (400 MHz, CHCl$_3$): δ7.0-7.5 (8H, m), 5.6 (1H, s), 4.4 (1H, m), 3.2-4.0 (2H, m), 1.6-2.2 (4H, m).<br>LCMS, 413, 98%<br>75% ee |

EXAMPLE 11

This example illustrates methodology and conditions for the chiral analysis of prodrug esters of (−)-CPTA.

Since the chiral center of the prodrug esters is adjacent to the carbonyl of the acid, the esters were analyzed to confirm that the optical center had not racemized during the coupling. Both MBX102 and the MBX102 acid have been resolved on a normal phase chiral column, but confirmation of the relative retentions of the enantiomeric esters on such a column would require standards of both enantiomers for all the compounds involved. Alternatively, the esters could be hydrolyzed to the known acids and the ratio of the enantiomeric acids could be analyzed, but some degree of racemization is likely under these conditions. Reverse phase chiral columns offer the ability to be interfaced with an LC-MS system, so that the enantiomers could be positively identified without separate standards. Under negative ion, selected ion monitoring (SIM) conditions, an LC-MS would be expected to be an order of magnitude more sensitive than UV detection as well as being much more specific. The application of chiral-column-LC-MS has proven to be an excellent method for characterizing the optical purity of this series of compounds. The quantitation limit has been shown to be well below the 2.5% limit set for the alternate optical isomer, and the extremely low level of detection gives more flexibility in the separation of the series, as well as establishing the relative retentions of the enantiomeric pairs in most cases without the need to produce racemized material.

The enantiomers of the prodrug esters synthesized were well separated using one of the columns and solvent systems listed below. Most of the enantiomers were separated using the reverse phase ES-OVM column with the mass spectrometer as a detector. Since this gives the added confirmation of the molecular species and isotope ratio, this was the preferred technique. For enantiomeric pairs which were not separated on the reverse phase column, a normal phase system was used and some of the sample was partly racemized to establish the retention time of the enantiomers.

Description of Analytical Conditions

Reversed Phase separation:
Column: Shinwa Chemicals Ultron ES-OVM 4.6×150 mm with matching pre column (part #712111630). Available from Mac Mod Analytical.
Solvents: "A" Acetonitrile, Ethanol or Methanol. "B" Water containing 20 milli molar NH4 OCOCH3 (Ammonium Acetate) adjusted to pH 4.6 with acetic acid.
Solvent Flow: 1 milliliter per minute Isocratic as indicated.
Detector: UV for method development at 220 or 270 nm or as specified. LC-MS using negative ion electrospray, monitoring two ions, M-H$^-$ and the chlorine 37 isotope (M+1$^-$)
Mass Spectrometer Waters/Micromass ZMD Bench top LC-MS with Electrospray source.
HPLC: Agilent 1050 or Shimadzu LC-10 as indicated.
Software: HP 3396 integrator for method development and Micromass MassLynx V3.4 for quantitation.

Methods Development:

Most prodrug esters separated using between 10 and 40% acetonitrile in water with an ammonium acetate buffer at pH 4.6. The free acid was a contaminant in the crude or racemized samples. The retention times of the acids were pH dependant, but the chromatography of the esters was in general not sensitive to pH. Retention and peak shape were affected by the concentration and injection solvent, and the samples were injected using a minimum concentration and the column solvent mixture for best results. The desired enantiomer was retained less and with a retention time of approximately 5 minutes, the second enantiomer eluted from 1 to 3 minutes later with complete separation in most cases. There was some peak tailing from the main enantiomer in some cases. The amount of acetonitrile was adjusted to give a retention time of about 5 minutes for the main component or best peak separation with maximum peak sharpness. Peaks retained more than 10 minutes tended to be too broad to accurately quantify the second enantiomer at levels under 2%.

Detection Limit:

Sample 1061-18-05 (the benzyl ester, MW 420) was mixed with racemized material to give an expected concentration of 2.47% of the unwanted enantiomer. The sample was analyzed repeatedly by LC-MS (monitoring ions at 419 and 421) giving an average of 2.6% recovery of the second enantiomer with a 10.9% RSD. See FIG. 18.

Normal Phase Separation:
Column: Analytical Column: Regis (S,S) WHELK-O 4.6× 250 mm with Peek Scientific Cyano pre column (part #DC5-CN). Preparative Column Regis (S,S) WHELK-O 20×250 mm with Cyano pre column.
Solvents:
"A" 10% of Solvent B in Hexane.
"B" Isopropanol (IPA), Ethanol or Ethyl Acetate buffered with ammonium acetate or triethylamine when indicated.
Solvent Flow: 1.2, 1.5 or 25 milliliter per minute Isocratic as indicated.
Detector: UV for method development at 270 nm or as specified.
HPLC: Agilent 1050, Gilson 321 or Shimadzu LC-10 as indicated.
Software: Gilson Unipoint, HP 3396 Integrator or Micromass MassLynx V 3.4 as indicated.
Methods Development:

Most prodrug esters separated using between 10 and 40% alcohol in Hexane without a modifier. The desired enantiomer was retained less. With a retention time of approximately 5 minutes for the first enantiomer, the second enantiomer eluted from 1 to 3 minutes later with complete separation. The compounds with a basic amine group required ammonium acetate (0.2%) as a modifier to sharpen the peak shape. Triethyl amine was tried but was not effective as a modifier. IPA was normally the first solvent tried, if the separations were not complete, ethanol or ethylacetate were used. The enantiomeric excess for each compound was measured using reverse phase chromatography when possible, but in several cases, separation was only possible using normal phase. In these cases, the data were collected and integrated using the MicroMass MassLynx software to be consistent with the other analyses (FIG. 19).

EXAMPLE 12

This example illustrates the plasma hydrolysis of various prodrug esters of the (S)-enantiomer of CPTA at physiological conditions. Hydrolysis was monitored and analyzed by HPLC. The hydrolytic product was identified by comparison to authentic (−) CPTA and the hydrolytic rates were calculated.

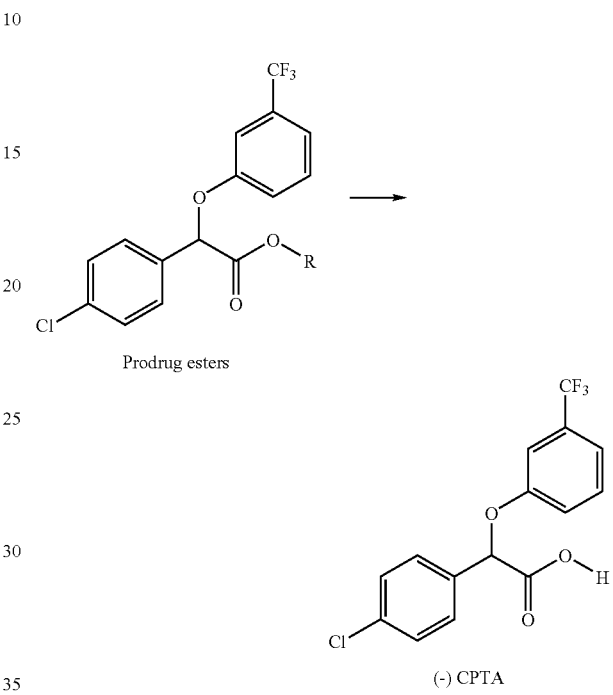

Prodrug esters (-) CPTA

Human plasma (heparinized, pooled) was obtained from Golden West Biololgicals Inc., USA; Plasma incubation was carried out in a Water Bath Shaker (New Brunswick Scientific, Inc.); Sample analyses were carried out on Agilent HPLC 1100 system.

General Hydrolytic Procedure:

Prepare 31.25 or 62.5 mM prodrug stock solutions in 100% DMSO. Add 4 μL of 31.25 or 62.5 mM prodrug stock solutions to 1.0 mL of plasma in a microcentrifuge tube to make plasma concentration at 125 or 250 μM, mix gently. Aliquots of 50 μL are transferred to 15 microcentrifuge vials. Three samples are immediately removed to a freezer at about −80° C. (0 time point), the remaining samples are incubated in a bath shaker at 37° C. Three samples are removed at 30 min, 2, 7 and 24 hr, and stored at −80° C. until analysis. The relative concentrations of MBX-compounds are determined by HPLC methods. If there are enough data points, the hydrolytic rate can be calculated using WinNonlin software. Table 10 provides a summary of plasma half-lives of some pro-drug esters and FIGS. 20A-20G illustrate the hydrolytic curves of those prodrug esters.

HPLC: Agilent 1100 HPLC System
Column:
Phenomenex Luna C18(2) 5u 150×2 mm lot #105554-2
Phenomenex Luna C18(2) 5u 250×4.6 mm lot #103992-8
Solvent Flow Rate: 0.25 or 1 ml/minute
Injection Volume: 20 or 40 μl
Run Time: 7 to 15 min Solvent Composition: 45 to 76% ACN/0.1% TFA in Water (V/V)
Detection: Diode Array UV-Visible Detector at 220 nm

TABLE 10

Plasma Half-Life of (−) CPTA Prodrugs

| Compound number | Plasma $T_{1/2}$ (hours) |
|---|---|
| 19.1 | 5.5 |
| 19.2 | <1 |
| 19.3 | <1 |
| 19.4 | <1 |
| 19.5 | <0.5 |
| 19.6 | 6.3 |
| 19.7 | <7 |
| 19.8 | <2 |
| 19.9 | <1 |
| 19.10 | <1 |
| 19.11 | <0.5 |
| 19.12 | <0.5 |
| 19.13 | <0.5 |
| 19.14 | <2 |
| 19.15 | <1 |
| 19.16 | <0.5 |
| 19.17 | <1 |
| 19.18 | <1 |
| 19.19 | <0.5 |
| 19.20 | <0.5 |
| 19.21 | <2 |
| 19.22 | <1 |
| 19.23 | <1 |
| 19.24 | <0.5 |
| 19.25 | <0.5 |
| 19.26 | <1 |
| 19.27 | <1 |
| 19.28 | <0.5 |

EXAMPLE 13

This example sets forth exemplary benzooxazole analogs for use according to their invention and their activity in vivo.

TABLE 1

2-Benzooxazole analogs

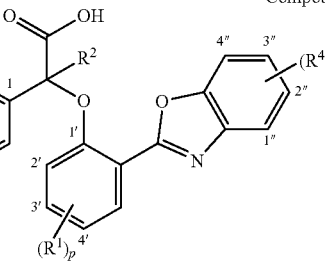

Compound I-X and Ia-X

| Compound | $R^2$ | $(R^3)_m$ | $(R^1)_p$ | $(R^4)_s$ | Configuration |
|---|---|---|---|---|---|
| I-1 | H | 4-Cl | H | H | R/S |
| I-3 | H | 3-$CF_3$ | H | H | R/S |
| I-89 | H | 3-$CF_3$ | 4'-$CF_3$ | H | R/S |
| I-92 | H | H | 4'-$CF_3$ | H | R/S |
| I-190 | H | 4-Cl | 4'-Cl | H | R/S |
| I-191 | H | 3-$CF_3$ | 4'-Cl | H | R/S |
| I-193 | H | 4-OMe | 4'-Cl | H | R/S |
| I-194 | H | 3-Cl | 4'-Cl | H | R/S |
| I-369 | H | H | 4'-$CF_3$ | H | S |
| I-372 | H | 4-Cl | 4'-$CF_3$ | H | (+) |
| Ia-365 | Me | H | 4'-$CF_3$ | H | S |
| Ia-366 | Me | H | 4'-$CF_3$ | H | R |

In Vivo Activities

The anti-diabetic activities of the compounds were evaluated in the C57BL/6j ob/ob Mice model.

Male, 7-9 weeks old, C57BL/6J ob/ob mice were purchased from The Jackson Laboratory (Bar Harbor, Me., USA). Animals were housed (4-5 mice/cage) under standard laboratory conditions at 22±3° C. temperature and 50±20% relative humidity, and were maintained on a diet of Purina rodent chow and water ad libitum. Prior to treatment, blood was collected from the tail vein of each animal. Mice that had non-fasting plasma glucose levels between 250 and 500 mg/dl were used. Each treatment group consisted of 8-10 mice that were distributed so that the mean glucose levels were equivalent in each group at the start of the study. Mice were dosed orally by gavage once a day for 1-4 days with vehicle and one or more dose of test compound at a dose ranging from 5 to 125 mg/kg. compounds were delivered in a liquid formulation containing 5% (v/v) dimethyl sulfoxide (DMSO), 1% (v/v) Tween 80 (and 0.9% (w/v) methylcellulose. The gavage volume was 10 ml/kg. Blood samples were taken at 6 hours after the each dose and analyzed for plasma glucose. Food intake and body weight were measured daily. Plasma glucose concentrations were determined calorimetrically using a commercial glucose oxidase method (Sigma Chemical Co, St. Louis, Mo., USA). Significant difference between groups (comparing drug-treated to vehicle-treated) was evaluated using the Student unpaired t-test.

The following table summarizes the anti-diabetic effects of selected compounds of the present invention and provides their relative potency. compounds that are effective for glucose lowering at the dose of ≧125 mg/kg are assigned a potency of +; compounds that are effective for glucose lowering at a dose of >25 mg/kg but <125 mg/kg are assigned a potency of ++; compounds that are effective for glucose lowering at a dose of ≦25 mg/kg are assigned a potency of +++. For example, a compound at 25 mg/kg that lowered the animal glucose level from 400 mg/dL (vehicle group value) to 250 mg/dL, is assigned the potency of +++.

Potency of Selected compounds

| Number | Compound # | Potency | Insulin Level compared with vehicle |
|---|---|---|---|
| 1 | I-1 | ++ | Lower |
| 2 | I-3 | + | Lower |
| 3 | I-89 | +++ | Lower |
| 4 | I-92 | +++ | Lower |
| 5 | I-190 | +++ | Lower |
| 6 | I-191 | +++ | Lower |
| 7 | I-193 | +++ | Lower |
| 8 | I-194 | +++ | Lower |
| 9 | I-369 | +++ | Lower |
| 10 | I-372 | +++ | Lower |
| 11 | Ia-365 | +++ | Lower |
| 12 | Ia-366 | +++ | Lower |

EXAMPLE 14

This example relates to the glucose lowering activity of (±) halofenate analogs and (−) halofenate analogs.

Male, 8-9 weeks old, C57BL/6J ob/ob mice were purchased from The Jackson Laboratory (Bar Harbor, Me., USA). Animals were housed (4-5 mice/cage) under standard laboratory conditions at 22±3° C. temperature and 50±20% relative humidity, and were maintained on a diet of Purina rodent chow and water ad libitum. Prior to treatment, blood was collected from the tail vein of each animal. Mice that had non-fasting plasma glucose levels between 250 and 500 mg/dl were used. Each treatment group consisted of 8-10 mice that were distributed so that the mean glucose levels were equivalent in each group at the start of the study. Mice were dosed orally by gavage once a day for 1-3 days with either vehicle, (−) halofenic acid, (±) analog 14, 29, 33, 34, 35, 36, 37, or 38 at 125 mg/kg or (−) analog 29, 36, 37 or 38 at 150 mg/kg. compounds were delivered in a liquid formulation containing 5% (v/v) dimethyl sulfoxide (DMSO), 1% (v/v) tween 80 and 0.9% (w/v) methylcellulose. The gavage volume was 10 ml/kg. Blood samples were taken at 6 hours after the each dose and analyzed for plasma glucose. Food intake and body weight were measured daily. Plasma glucose concentrations were determined calorimetrically using glucose oxidase method (Sigma Chemical Co, St. Louis, Mo., USA). Significant difference between groups (comparing drug-treated to vehicle-treated) was evaluated using the Student unpaired t-test.

As illustrated in the following table, compounds were evaluated in 5 different experiments. Single dose (−) halofenic acid significantly reduced plasma glucose concentrations at 6 hours. Analog 14 significantly lowered glucose concentrations at 6, 30 and 54 hours. Analog 33 significantly lowered glucose concentrations at 6 and 54 hours. Analog 29 and 38 significantly lowered plasma glucose concentrations at 6, 30 and 54 hours. Analog 35 and 36 significantly lowered plasma glucose concentrations at 30 and 54 hours. Analog 37 significantly lowered plasma glucose concentrations at 54 hours. Single dose (−) analogs 29, 36, 37 and 38 significantly reduced plasma glucose concentrations at 6 hours. compound treatments did not affect the animal's food intake and body weight.

TABLE 1

(±) and (−) Halofenate analogs. compounds described in reference to Formula II.

Formula II

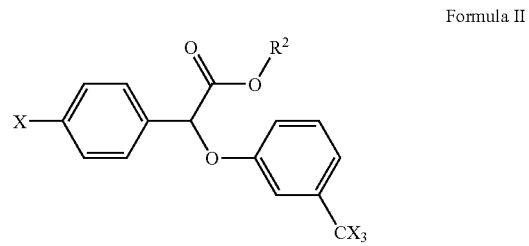

| Cmpd No. | X | $CX_3$ | $R^2$ |
|---|---|---|---|
| halofenic acid | Cl | $CF_3$ | H |
| 14 | F | $CF_3$ | $(CH_2)_2NHAc$ |
| 29 | Br | $CF_3$ | $(CH_2)_2NHAc$ |
| 33 | Cl | $CF_3$ | $(CH_2)_3CH_3$ |
| 35 | Cl | $CF_3$ | $(CH_2)_2N(CH_3)_2$ |
| 36 | Cl | $CF_3$ | $(CH_2)_2NHCOPh$ |
| 37 | Cl | $CF_3$ | $CH_2CONH_2$ |
| 38 | Cl | $CF_3$ | $CH_2CON(CH_3)_2$ |

TABLE 2

| | | 6 hours | | 30 hours | | 54 hours | |
|---|---|---|---|---|---|---|---|
| | Predose Glucose (mg/dl) | Glucose (mg/dl) | P VALUE vs. veh | Glucose (mg/dl) | P VALUE vs. veh | Glucose (mg/dl) | P VALUE vs. veh |
| Vehicle | 313 ± 18 | 303 ± 19.8 | | NA | | NA | |
| (−)halofenic acid | 312.9 ± 17.7 | 163.8 ± 11.8 | 0.0011 | NA | | NA | |
| Vehicle | 360.2 ± 27.8 | 405.8 ± 25.8 | | 356.0 ± 27.6 | | 386.1 ± 20.6 | |
| (±)Analog 14 | 361.0 ± 17.1 | 328.9 ± 34.1 | 0.0444 | 267.0 ± 21.3 | 0.0099 | 293.0 ± 29.4 | 0.0092 |
| Vehicle | 291.6 ± 18.5 | 363.0 ± 25.1 | | 340.8 ± 30.0 | | 351.5 ± 23.8 | |
| (±)Analog 33 | 292.0 ± 19.1 | 227.5 ± 13.2 | 0.0001 | 298.0 ± 15.3 | 0.1119 | 286.6 ± 9.9 | 0.0125 |
| Vehicle | 387.1 ± 14.3 | 371.5 ± 24.2 | | 326.2 ± 22.5 | | 374.0 ± 37.9 | |
| (±)Analog 29 | 387.1 ± 16.0 | 299.7 ± 24.5 | 0.0259 | 237.4 ± 14.9 | 0.0020 | 293.3 ± 9.7 | 0.0268 |
| (±)Analog 35 | 387.0 ± 18.0 | 319.6 ± 26.7 | 0.0834 | 276.8 ± 17.6 | 0.0504 | 286.2 ± 31.5 | 0.0458 |
| (±)Analog 37 | 387.4 ± 18.8 | 345.4 ± 19.7 | NS | 312.5 ± 21.7 | NS | 285.1 ± 14.7 | 0.0210 |
| Vehicle | 329.6 ± 16.1 | 361.8 ± 23.2 | | 346.5 ± 24.6 | | 379.2 ± 24.4 | |
| (±)Analog 36 | 329.7 ± 17.6 | 300.5 ± 27.3 | 0.0522 | 249.7 ± 8.6 | 0.0008 | 272.2 ± 18.4 | 0.0013 |
| (±)Analog 38 | 329.4 ± 18.9 | 303.2 ± 18.2 | 0.0312 | 245.6 ± 15.6 | 0.0014 | 243.1 ± 10.6 | 0.0000 |
| Vehicle | 373.0 ± 13.6 | 405.8 ± 33.7 | | NA | | NA | |
| (−)Analog 36 | 373.2 ± 15.5 | 281.1 ± 18.2 | 0.0019 | NA | | NA | |
| (−)Analog 37 | 373.4 ± 16.1 | 271.7 ± 22.5 | 0.0018 | NA | | NA | |
| (−)Analog 38 | 373.4 ± 16.1 | 251.2 ± 23.6 | 0.0007 | NA | | NA | |
| (−)Analog 29 | 372.2 ± 17.1 | 333.5 ± 16.1 | 0.0353 | NA | | NA | |

Glucose-lowering Activities of (±)Halofenate and (−)Halofenate Analogs

EXAMPLE 15

Preparation of 2-(4-trifluoromethyl-phenoxy)-2-(3-trifluoromethyl-phenyl)propionic acid

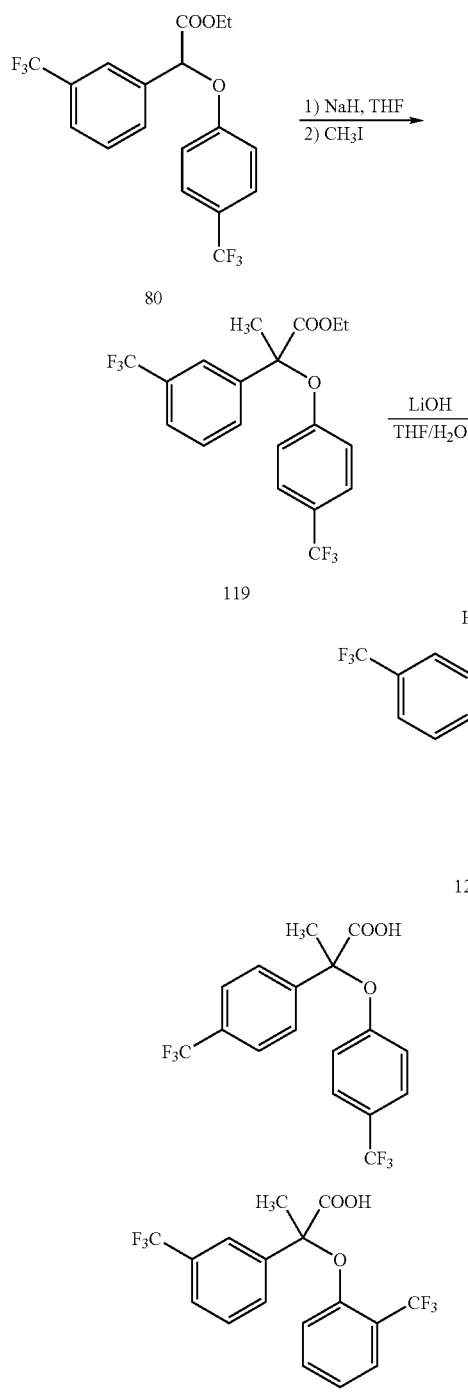

To a solution of ester 80 (3.01 g, 7.69 μmmol) in anhyrous THF (30 mL) was added NaH (60% in oil, 0.80 g, 0.020 mol). After the resulting solution was stirred at rt for 2 h, iodomethane (2.5 mL, 0.040 mol) was added. The resulting mixture was stirred at rt overnight. The reaction was quenched with sat. NH$_4$Cl, diluted with EtOAc, washed with diluted aqueous HCl and brine, dried over Na$_2$SO$_4$, concentrated in vacuo, and purified by flash chromatography on silica gel (5:95 EtOAc/hexanes) to afford ester 119 (3.18 g, 87%) as a colorless liquid. $^1$H NMR (400 MHz, DMSO-d$_6$): δ 7.91 (1H, s), 7.88 (1H, d), 7.7 (1H, d), 7.69 (1H, d), 7.65 (2H, d), 7.02 (1H, d), 4.16 (2H, q), 2.48 (3H, s), 1.03 (3H, t) ppm. To a solution of ester 119 (1.03 g, 2.17 mmol) in THF/H$_2$O (15 mL/5 mL) at rt was added lithium hydroxide monohydrate (0.95 g, 0.022 mol). The resulting solution was refluxed at rt for 1 h, cooled to rt, quenched with 1N aqueous HCl and extracted with EtOAc. The organic layer was washed with brine, dried over Na$_2$SO$_4$ and concentrated in vacuo to afford acid 120 (0.93 g, 96%) as a pale-yellow liquid.

Using the above procedures, but substituting the appropriate α-phenoxy phenyl acetic esters for 80, there were obtained the following compounds: 2-(4-Trifluoromethyl-phenoxy)-2-(4-trifluoromethyl-phenyl)-propionic acid, 121; 2-(2-Trifluoromethyl-phenoxy)-2-(3-trifluoromethyl-phenyl)-propionic acid, 122, $^1$HNMR (d-DMSO, 400 MHz) δ 13.85 (s, 1H), 8.04 (s, 1H), 7.86 (d, 1H), 7.74 (d, 1H), 7.70-7.66 (m, 3H), 7.56 (m, 1H), 7.15 (m, 1H), 6.89 (d, 1H), 1.89 (s, 3H).

EXAMPLE 16

Preparation of (4-trifluoromethyl-phenoxy)-(3-trifluoromethyl-phenyl)-acetic acid 2-acetylamino-ethyl ester, 136

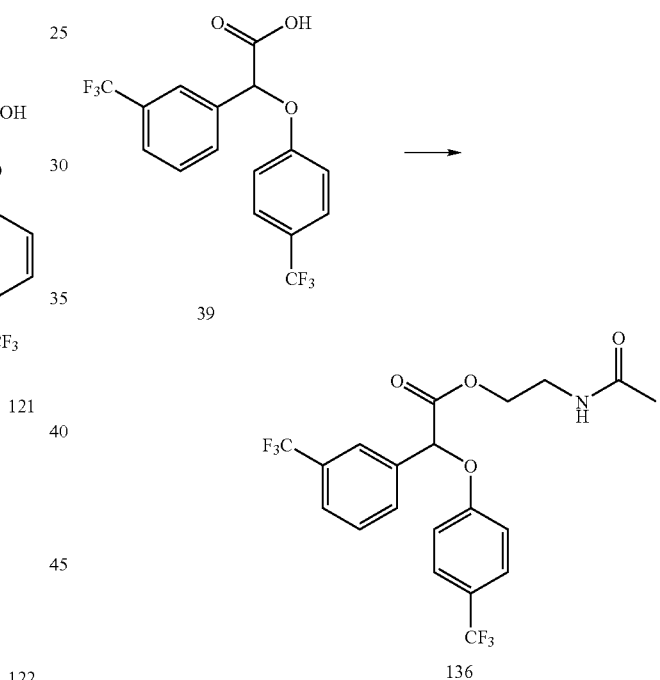

To a slurry of acid 39 (25.8 g, 0.071 mol) in anhydrous 1,2-dichloroethane (380 mL) was added thionyl chloride (16.0 mL, 0.21 mol), and then the resulting mixture was refluxed for 2 h. The mixture was cooled to rt, diluted with dry THF (150 mL) until the cloudy mixture turned clear, and then N-acetylethanolamine (39.12 g, 0.38 mol) was added. The resulting solution was stirred at rt overnight. The reaction was quenched with sat. NaHCO$_3$ carefully, diluted with EtOAc, and washed with water. The organic layer was washed with brine, dried over Na$_2$SO$_4$, concentrated in vacuo, and the residue was recrystallized from iPrOH/hexanes (11 mL/31.5 mL) to afford pure product 136 (22.78 g, 71%) as a off-white solid. $^1$H NMR (400 MHz, CDCl$_3$): δ 7.89 (1H, s), 7.80 (1H, d), 7.69 (1H, d), 7.57-7.61 (3H, t), 7.06 (2H, t), 5.78 (1H, s), 5.27 (1H, br), 4.24 (2H, m), 3.45 (2H, dd), 1.81 (3H, s) ppm.

Using the above procedure, but employing different carboxylic acids and/or different alcohols, the corresponding esters analogous to 136 are obtained.

EXAMPLE 17

Preparation of (3-trifluoromethyl-phenyl)-(6-trifluoromethyl-pyridin-3-yloxy)-acetic acid 2-morpholin-4-yl-ethyl ester, 137

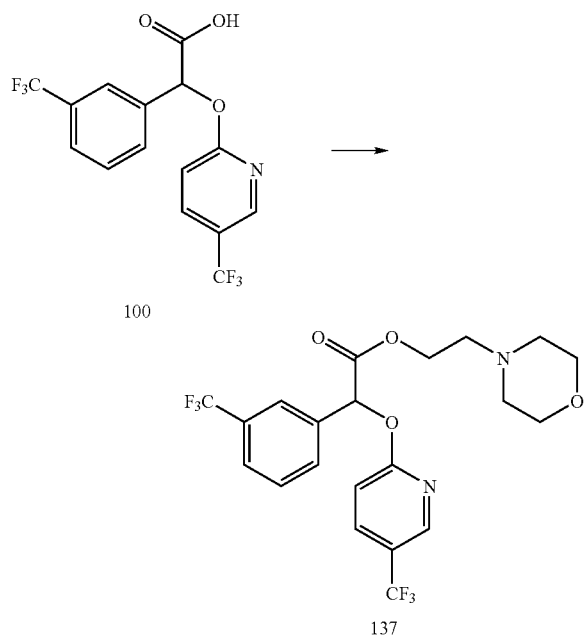

(3-Trifluoromethyl-phenyl)-(5-trifluoromethyl-pyridin-2-yloxy)-acetic acid, 100, prepared as described in Example 4, (0.05 mol) was converted into the acid chloride, using the procedure of Example 6. The acid chloride (0.01 mol) was dissolved in tetrahydrofuran (25 mL) and N,N-dimethylaniline (2 mL) and morpholinoethanol (2 mL) were added. The progress of the reaction was monitored by TLC. When the reaction was complete, water and ether were added. The organic phase was washed with dilute hydrochloric acid, dried and concentrated. The residue was chromatographed to afford the title compound 137.

Using the above procedure, but employing different carboxylic acids and/or different alcohols, the corresponding esters analogous to 137 can be obtained.

EXAMPLE 18

Preparation of Enantiomers of (4-trifluoromethyl-phenoxy)-(3-trifluoromethyl-phenyl)acetic acid, 39

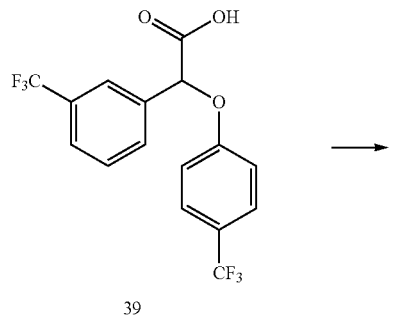

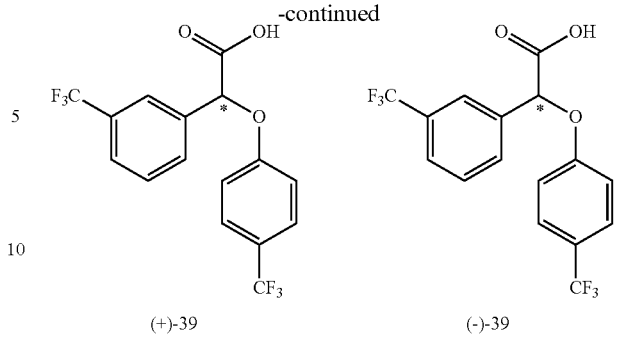

Optically pure (−)-39 salt was obtained via classical resolution by serial recrystallization of the salt of the racemic acid 39 with (1R,2R)-(−)-2-amino-1-(4-nitrophenyl)-1,3-propandiol (0.55 eq.) in EtOAc/hexanes at 75° C. to rt. The first crystal collected afforded (−)-39 salt. Serial recrystallization of the remaining mother liquid afforded another optically pure (+)-39 salt. After acidification of both salts with 1N HCl in EtOAc, optically pure (−)-39 and (+)-39 were obtained as white solids respectively. (+)-39, $[\alpha]^{25}\lambda=+74.6$ (c=0.55, $CH_3OH$), and (−)-39 $[\alpha]^{25}\lambda=-74.8$ (c=0.89, $CH_3OH$). Chiral HPLC analysis of enantiomers was carried out at λ=220 nm by injecting 10 µL of an approximately a 0.5 mg/mL solution of the sample dissolved in mobile phase onto a 25 cm×4.6 mm Regis Technologies (R,R) Whelk-O1 5 µm column with a 1.5 mL/min flow of (1.5/98.5/0.05) iPrOH/hexanes/TFA. Under these conditions, (+)-enantiomer eluted at 6.6 min, (−) enantiomer at 8.8 min (approximate retention times).

EXAMPLE 19

Preparation of Esterified Compounds

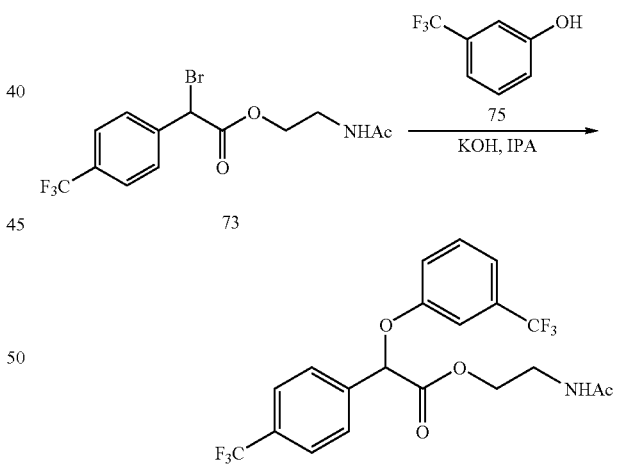

Potassium hydroxide (2.6 g, 0.046 mole) was dissolved in isopropanol (40 mL) under argon by heating to 50-60° C. The solution was the cooled to 0-10° C. in an ice bath. To this was added 3-trifluoromethylphenol (6.5 mL (8.7 g), 0.053 mole), which raised the internal temperature to 10-20° C. (2-Acetamidoethyl)-4-trifluoromethylphenylbromoacetate 73 (16.2 g, 0.044 mole) was dissolved in 12 mL isopropanol and cooled to 0-10° C. The phenoxide solution was then added to the bromoester, which raised the internal temperature to 5-15° C. The resulting mixture was stirred for 4 h in the cold bath. Citric acid (1.6 g, 0.0084 mole) was added in 12 mL water.

The mixture was filtered to remove white potassium bromide and the cake washed with isopropanol (20 mL). The isopropanol was rotary evaporated and the residue dissolved in ethyl acetate (72 mL) and extracted with water (24 mL). The ethyl acetate phase was dried over sodium sulfate and filtered and the filter cake washed with ethyl acetate. After rotary evaporation, crude product were obtained. This was dissolved in ethyl ether:hexane (1:1) and diluted with hexane, whereupon some material oiled out. The mixture was cooled in an ice bath to 2-5° C. a white solid formed at once and was filtered and washed with ethyl ether:hexane (1:1) to afford 142, after drying under vacuum.

Using the above procedures, but substituting the appropriate phenols and bromoesters for 73, the following compounds were obtained: 143-147.

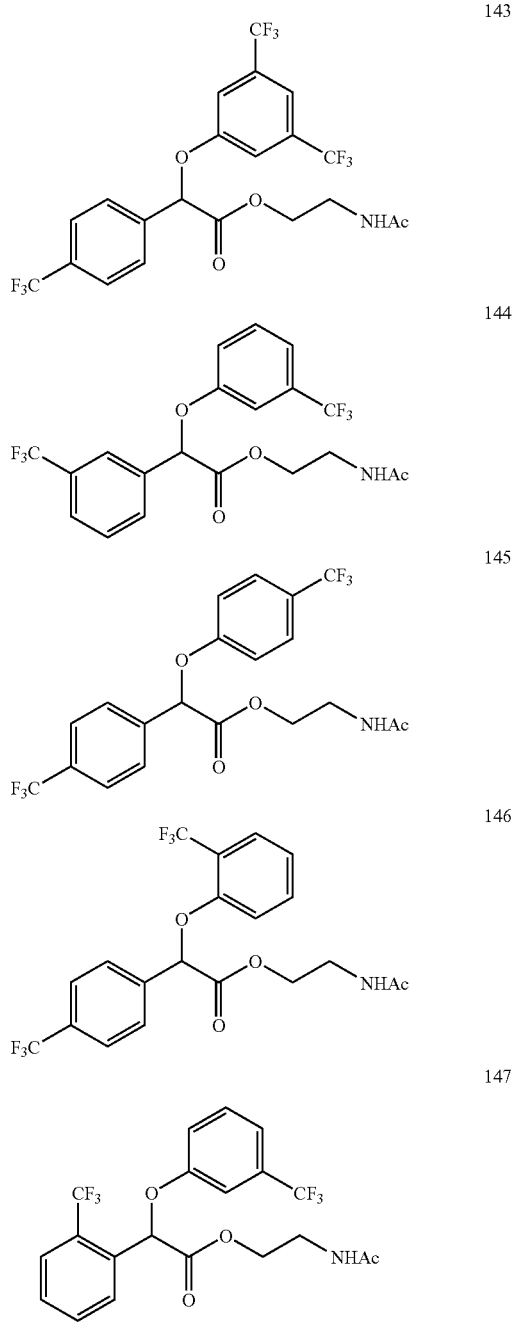

EXAMPLE 20

In Vivo Activities

The anti-diabetic activities of the compounds were evaluated in the C57BL/6j ob/ob Mice model.

A. Materials and Methods

Male, 7-9 weeks old, C57BL/6J ob/ob mice were purchased from The Jackson Laboratory (Bar Harbor, Me., USA). Animals were housed (4-5 mice/cage) under standard laboratory conditions at 22±3° C. temperature and 50±20% relative humidity, and were maintained on a diet of Purina rodent chow and water ad libitum. Prior to treatment, blood was collected from the tail vein of each animal. Mice that had non-fasting plasma glucose levels between 250 and 500 mg/dl were used. Each treatment group consisted of 8-10 mice that were distributed so that the mean glucose levels were equivalent in each group at the start of the study. Mice were dosed orally by gavage once a day for 1-4 days with vehicle and one or more dose of test compound at a dose ranging from 5 to 125 mg/kg. compounds were delivered in a liquid formulation containing 5% (v/v) dimethyl sulfoxide (DMSO), 1% (v/v) Tween 80® and 0.9% (w/v) methylcellulose. The gavage volume was 10 ml/kg. Blood samples were taken at 6 hours after the each dose and analyzed for plasma glucose. Food intake and body weight were measured daily. Plasma glucose concentrations were determined colorimetrically using a commercial glucose oxidase method (Sigma Chemical Co, St. Louis, Mo., USA). Significant difference between groups (comparing drug-treated to vehicle-treated) was evaluated using the Student unpaired t-test.

B. Results

Table 1 provides the relative potency of some selected compounds of the invention. compounds that are effective for glucose lowering at the dose of ≦125 mg/kg are assigned a potency of ++; compounds that are less effective for glucose lowering, typically exhibiting activity at a multiple dose or elevated dose of >125 mg/kg is assigned the potency of +.

TABLE 1

Potency of Invention Compounds

| Number | Compound # | Potency | Insulin Level compared with vehicle |
|---|---|---|---|
| 1 | 39 | ++ | Lower |
| 2 | 81 | ++ | Lower |
| 3 | 83 | ++ | Lower |
| 4 | 85 | ++ | Lower |
| 5 | 86 | ++ | Lower |
| 6 | 89 | ++ | Lower |
| 7 | 100 | ++ | Lower |
| 8 | 120 | ++ | Lower |
| 9 | 121 | ++ | Lower |
| 10 | 128 | ++ | Lower |
| 11 | 136 | ++ | Lower |
| 12 | (−)-39 | ++ | Lower |
| 13 | (+)-39 | ++ | Lower |
| 14 | 142 | ++ | Lower |
| 15 | 143 | ++ | Lower |
| 16 | 144 | ++ | Lower |
| 17 | 145 | ++ | Lower |
| 18 | 146 | + | Lower |
| 19 | 147 | + | Lower |

Each publication, patent application, patent, and other reference cited herein is incorporated by reference in its entirety to the extent that it is not inconsistent with the present disclosure. In particular, all publications cited herein are incorporated herein by reference in their entirety for the purpose of describing and disclosing the methodologies, reagents, and tools reported in the publications that might be used in connection with the invention. Nothing herein is to be construed as an admission that the invention is not entitled to antedate such disclosure by virtue of prior invention.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method of treating edema in a subject with a PPARγ-responsive condition or disease, comprising administering to the subject a therapeutically effective amount of an edema-sparing PPARγ modulator wherein the modulator is a compound of Formula I:

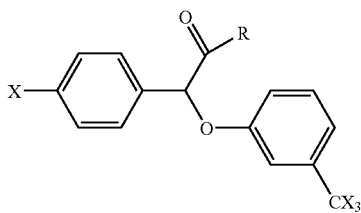

Formula I wherein R is a member selected from the group consisting of a hydroxy, alkoxy, heteroalkoxy, aryloxy, heteroaryloxy, lower aralkoxy, di-lower alkylamino-lower alkoxy, lower alkanamido lower alkoxy, benzamido-lower alkoxy, ureido-lower alkoxy, N'-lower alkyl-ureido-lower alkoxy, carbamoyl-lower alkoxy, halophenoxy substituted lower alkoxy, carbamoyl substituted phenoxy, carbonyl-lower alkylamino, N,N-di-lower alkylamino-lower alkylamino, halo substituted lower alkylamino, hydroxy substituted lower alkylamino, lower alkanolyloxy substituted lower alkylamino, ureido, arylsulfonamido, alkylsulfonamido and lower alkoxycarbonylamino; and each X is independently a halogen; or a pharmaceutically acceptable salt thereof.

2. The method of claim 1, wherein the administering is systemic.

3. The method of claim 1, wherein the administering is local.

4. The method of claim 1, wherein the administering is by the intravenous, oral, or rectal routes.

5. The method of claim 1, wherein the administering is topical.

6. The method of claim 1, wherein the condition is osteoporosis.

7. The method of claim 1, wherein the condition is inflammation or allergy.

8. The method of claim 1, wherein the condition is eczema, acne vulgaris, or psoriasis.

9. The method of claim 1, wherein the condition is cachexia, irritable bowel syndrome, inflammatory bowel disease, including Crohn's disease and ulcerative colitis, pancreatitis, abdominal obesity, neurodegenerative disease, or retinopathy.

10. The method of claim 1, wherein the subject is human.

11. The method of claim 1, wherein the subject is human and the compound is administered as a (−) enantiomer which is substantially free of its (+) enantiomer.

12. The method of claim 11, wherein the compound is halofenate.

13. The method of claim 1, wherein the administering is chronic.

14. The method of claim 10, wherein the subject has heart failure, congestive heart failure, or hypertension.

15. The method of claim 12, wherein the compound is administered in an amount from 100 to 800 mg per day by the oral route.

16. The method of claim 15, wherein the daily dosage is from about 200 mg to about 600 mg.

* * * * *